(12) United States Patent
Lam et al.

(10) Patent No.: US 8,920,436 B2
(45) Date of Patent: Dec. 30, 2014

(54) ENDOSCOPIC TISSUE ANCHOR DEPLOYMENT

(75) Inventors: Cang Lam, Tustin, CA (US); Richard C. Ewers, Fullerton, CA (US); Christopher James Earley, San Clemente, CA (US)

(73) Assignee: USGI Medical, Inc., San Clemente, CA (US)

( * ) Notice: Subject to any disclaimer, the term of this patent is extended or adjusted under 35 U.S.C. 154(b) by 429 days.

(21) Appl. No.: 13/348,201

(22) Filed: Jan. 11, 2012

(65) Prior Publication Data
US 2012/0184972 A1 Jul. 19, 2012

Related U.S. Application Data

(60) Provisional application No. 61/432,537, filed on Jan. 13, 2011.

(51) Int. Cl.
*A61B 17/04* (2006.01)
*A61B 17/29* (2006.01)
*A61B 17/00* (2006.01)
*A61B 17/06* (2006.01)

(52) U.S. Cl.
CPC ......... *A61B 17/0401* (2013.01); *A61B 17/0487* (2013.01); *A61B 17/29* (2013.01); *A61B 2017/00353* (2013.01); *A61B 2017/0409* (2013.01); *A61B 2017/0417* (2013.01); *A61B 2017/0464* (2013.01); *A61B 2017/06052* (2013.01); *A61B 2017/2905* (2013.01); *A61B 2017/2916* (2013.01)
USPC ............ 606/139; 606/144; 606/205; 606/207

(58) Field of Classification Search
CPC ............................ A61B 17/0401; A61B 17/29
USPC ................. 606/139–148, 151, 153, 205–209
See application file for complete search history.

(56) References Cited

U.S. PATENT DOCUMENTS

| | | | |
|---|---|---|---|
| 7,261,728 B2 * | 8/2007 | Long et al. ................... | 606/207 |
| 7,347,863 B2 | 3/2008 | Rothe et al. | |
| 7,361,180 B2 | 4/2008 | Saadat et al. | |
| 7,416,554 B2 | 8/2008 | Lam et al. | |
| 7,618,426 B2 | 11/2009 | Ewers et al. | |
| 7,736,374 B2 | 6/2010 | Vaughan et al. | |
| 2005/0065536 A1 | 3/2005 | Ewers et al. | |
| 2005/0251165 A1 * | 11/2005 | Vaughan et al. ............. | 606/153 |
| 2005/0251202 A1 * | 11/2005 | Ewers et al. .................. | 606/213 |
| 2006/0020274 A1 | 1/2006 | Ewers et al. | |
| 2006/0271074 A1 * | 11/2006 | Ewers et al. .................. | 606/148 |
| 2008/0086155 A1 | 4/2008 | Rothe et al. | |
| 2008/0262539 A1 | 10/2008 | Ewers et al. | |
| 2009/0312603 A1 | 12/2009 | Lam et al. | |

* cited by examiner

*Primary Examiner* — Kathleen Holwerda
(74) *Attorney, Agent, or Firm* — Kenneth H. Ohriner; Perkins Coie LLP

(57) ABSTRACT

An endoscopic tissue anchor deployment device includes a handle, an elongated shaft defining an internal lumen, and an end effector attached to the distal end of the elongated shaft. A tissue anchor catheter is removably inserted through the lumen of the elongated shaft, the catheter having a tissue anchor assembly that is deployable from its distal end. The handle may include a pin and track assembly that define a series of handle actuation steps corresponding to deployment steps for the deployment device end effector and the tissue anchor catheter. In some embodiments, the handle includes a catheter stop member that prevents movement of the tissue anchor catheter under certain circumstances, and a handle stop member that prevents actuation of the handle under certain circumstances.

18 Claims, 56 Drawing Sheets

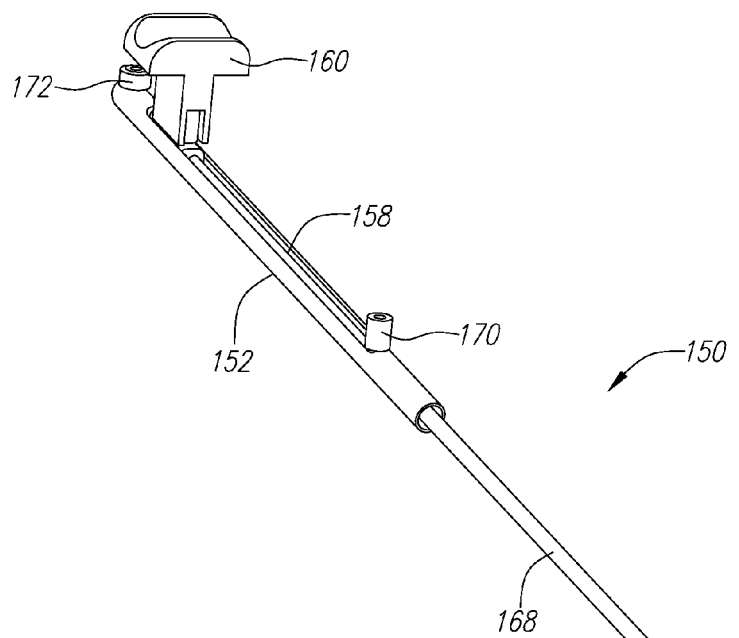
FIG. 15C
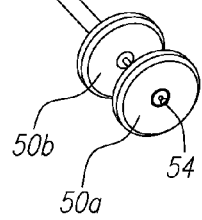

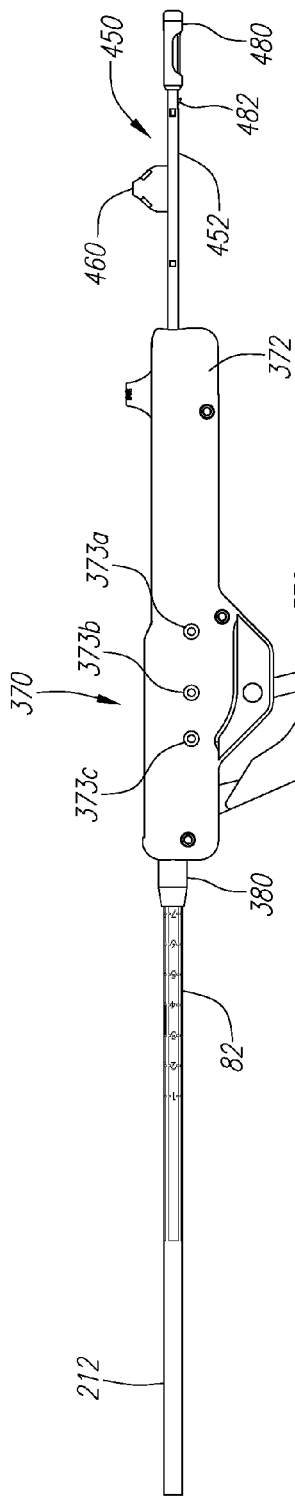
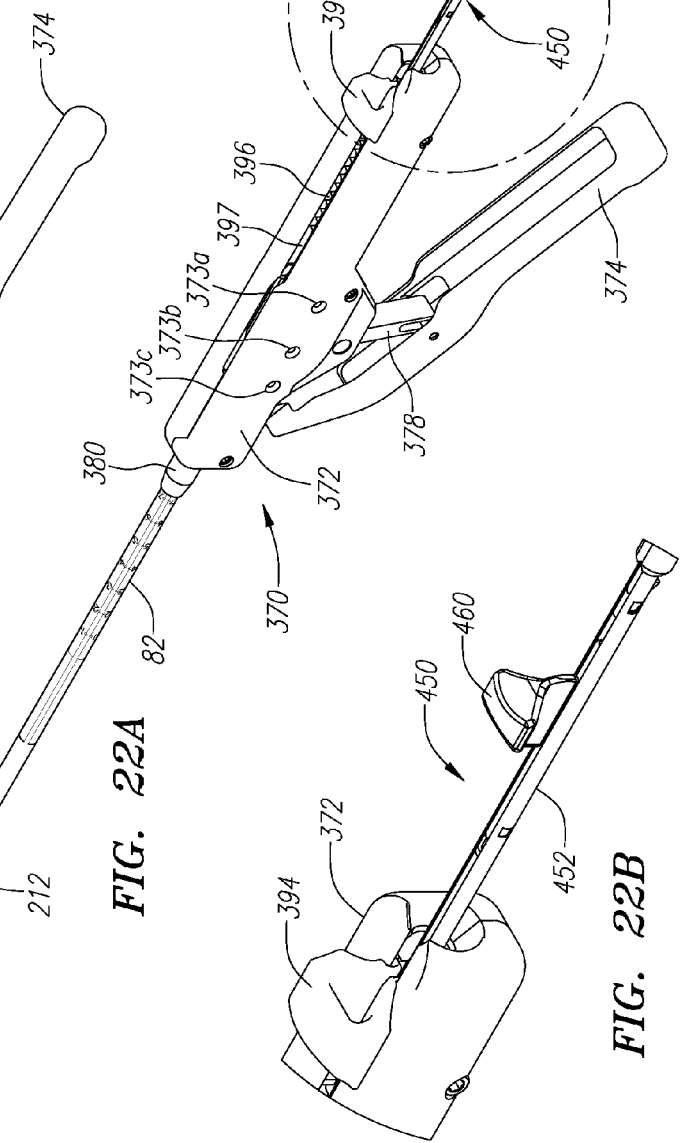
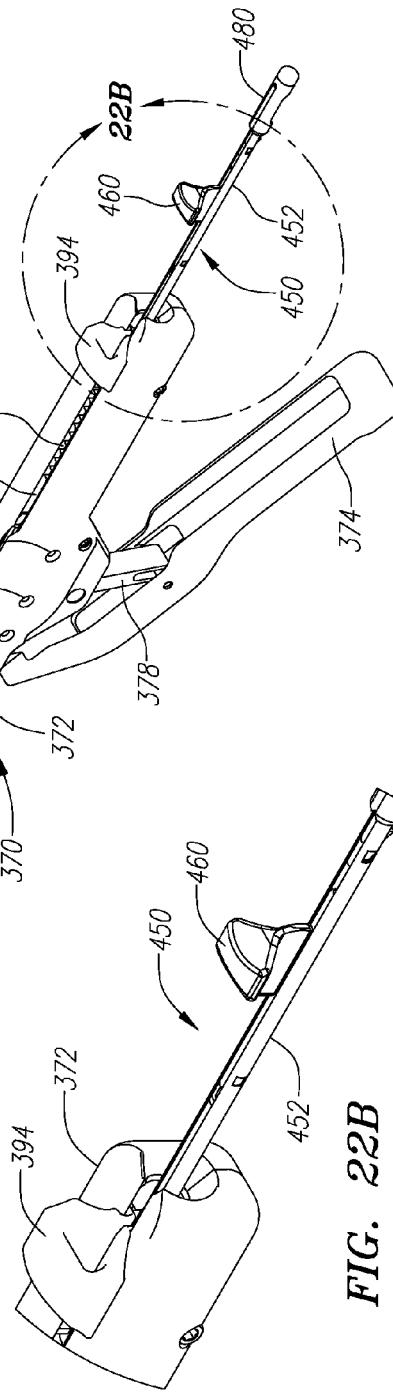
FIG. 21
FIG. 22A
FIG. 22B

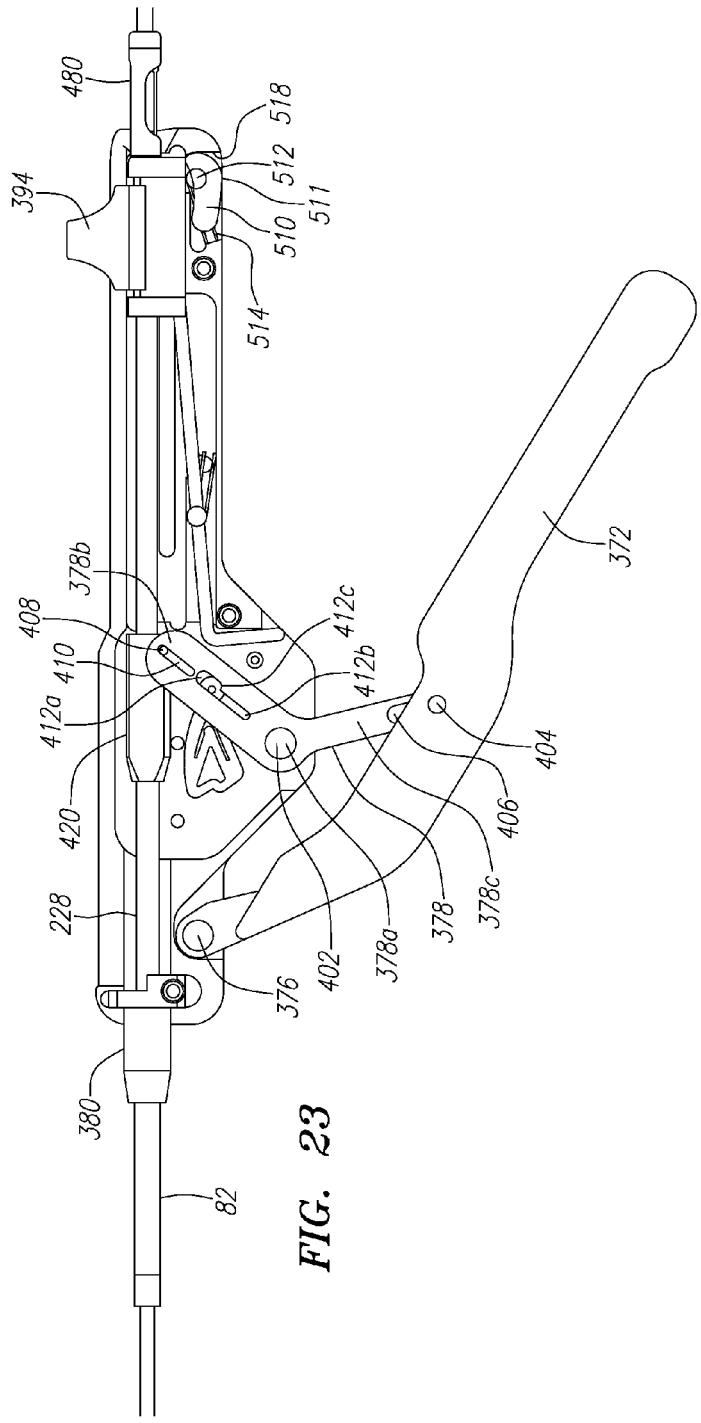
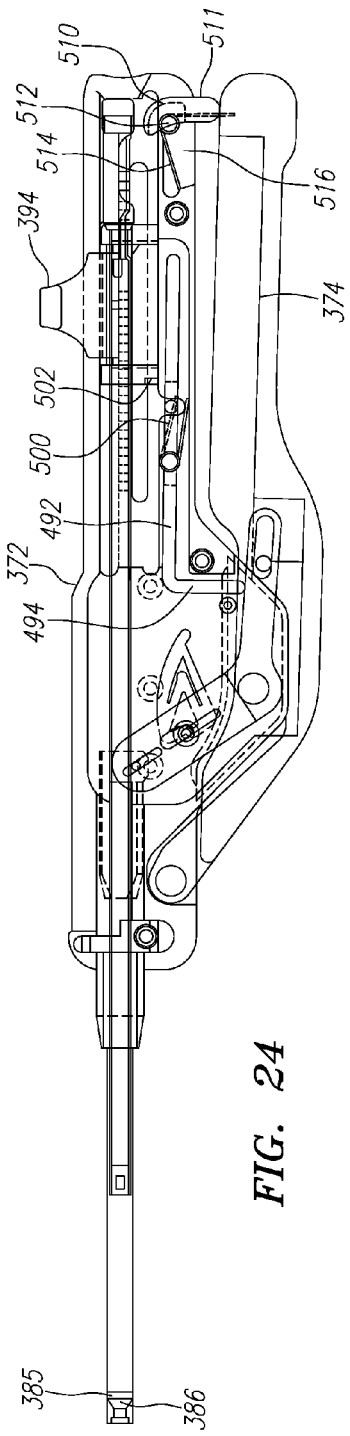
FIG. 23
FIG. 24

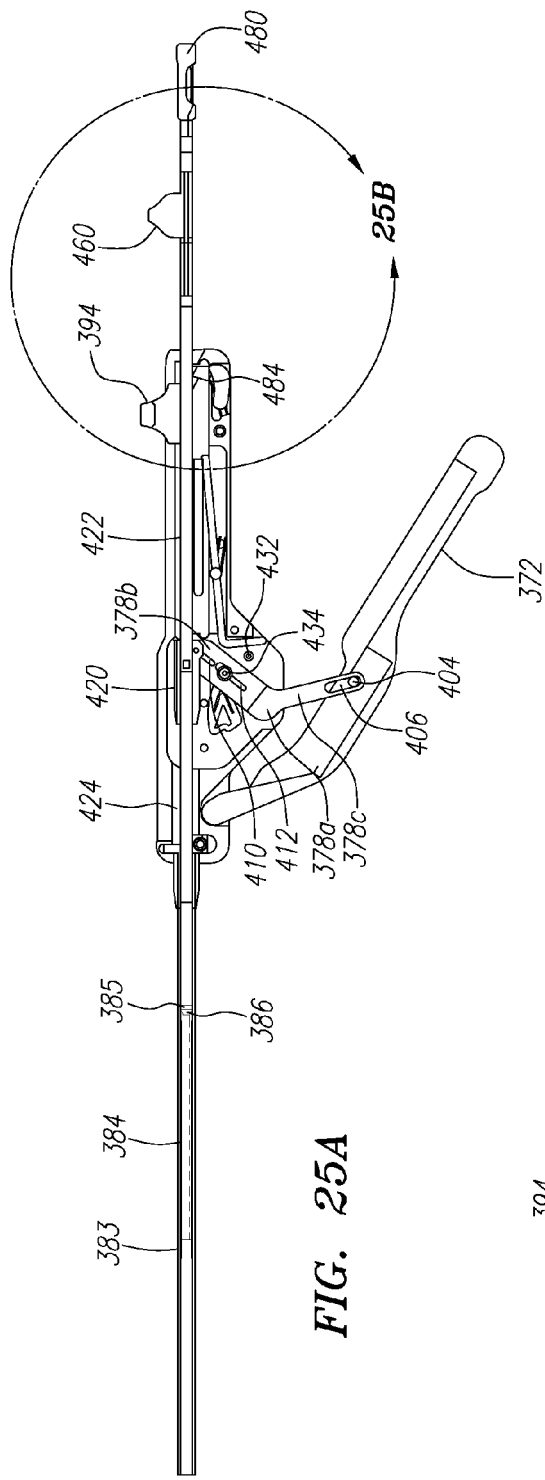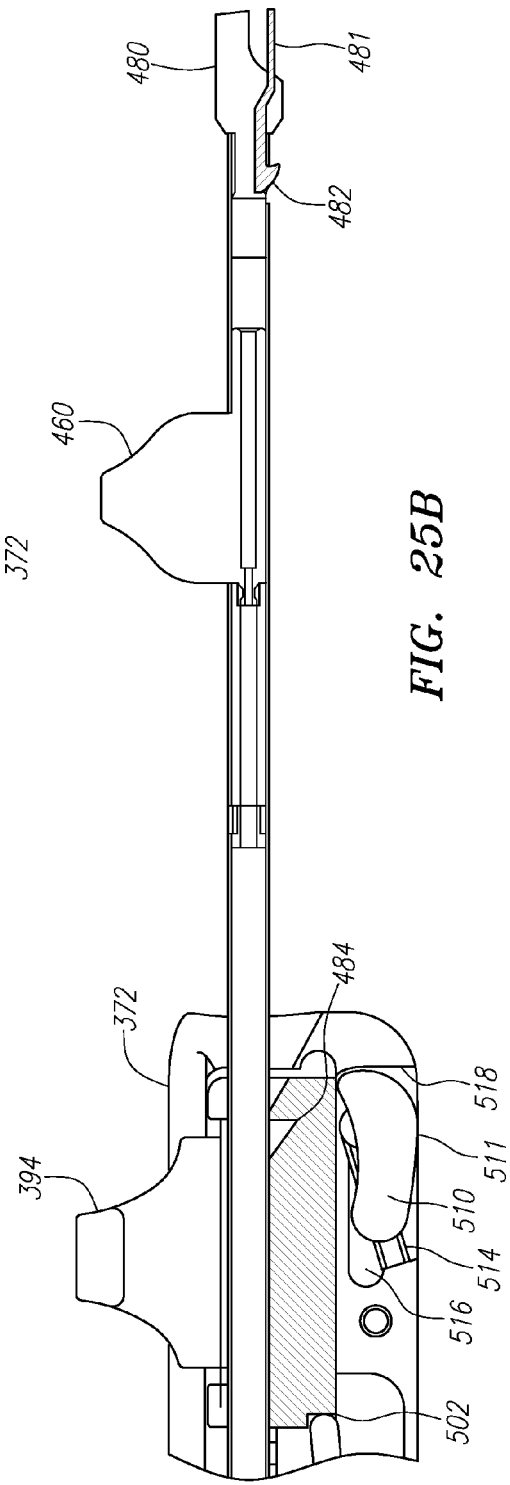

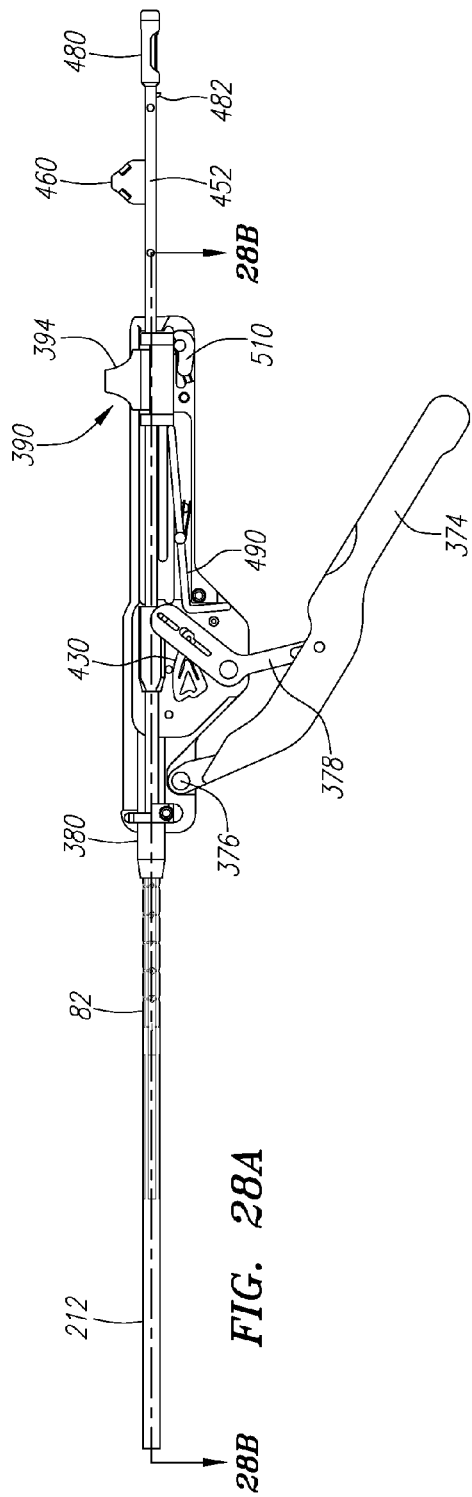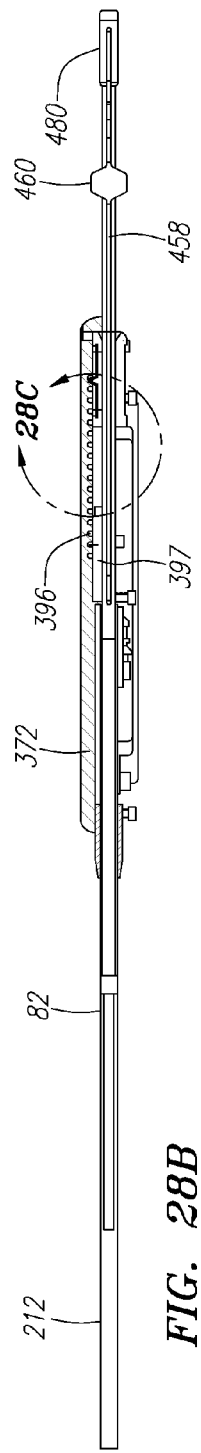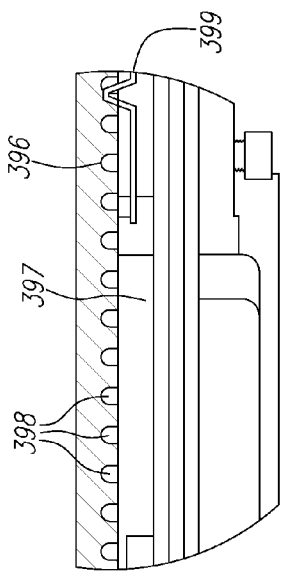
FIG. 28A
FIG. 28B
FIG. 28C

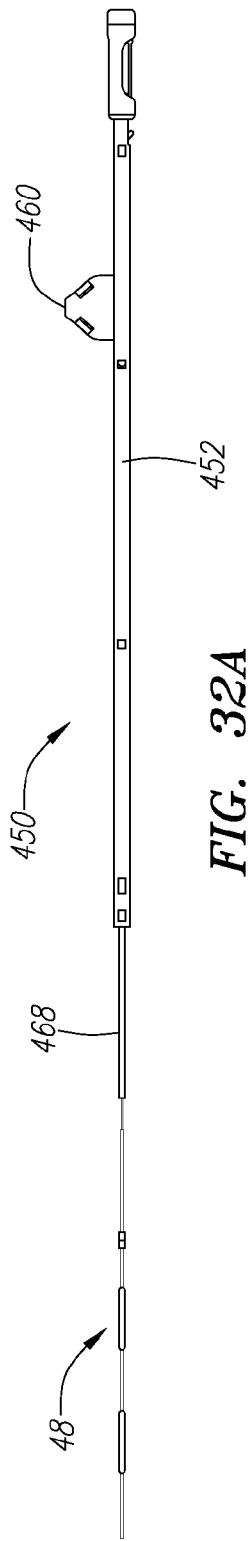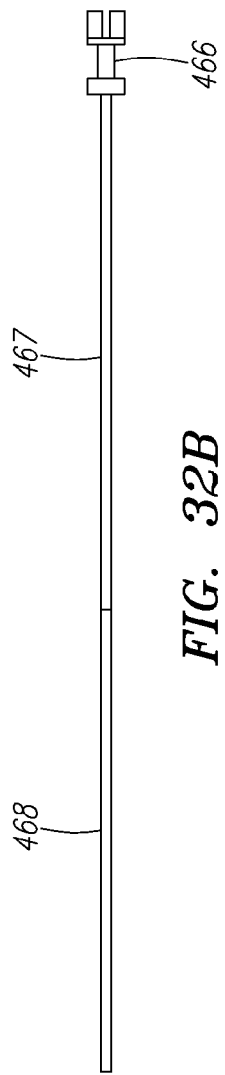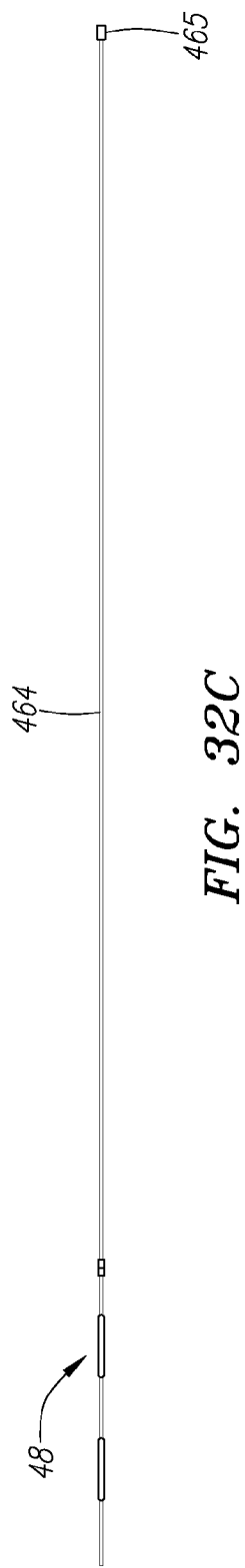

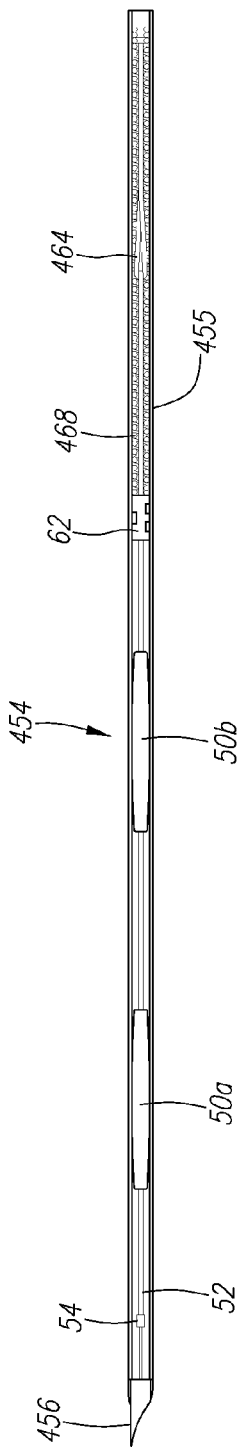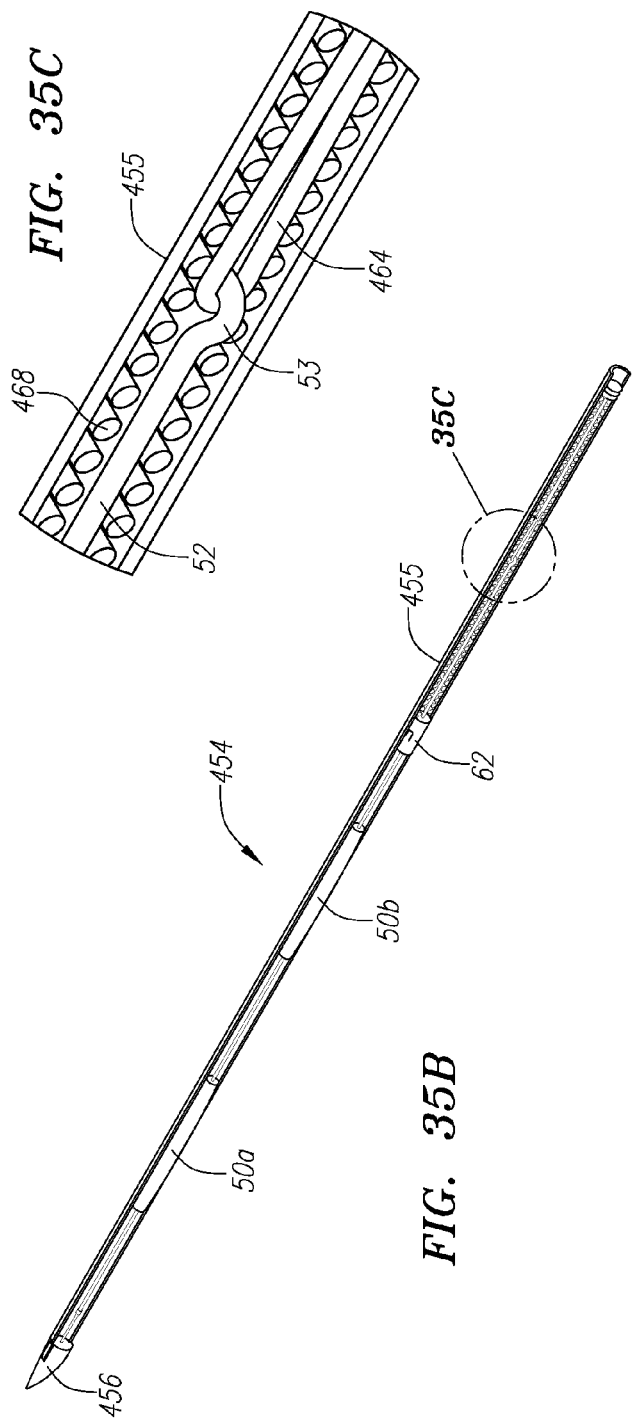

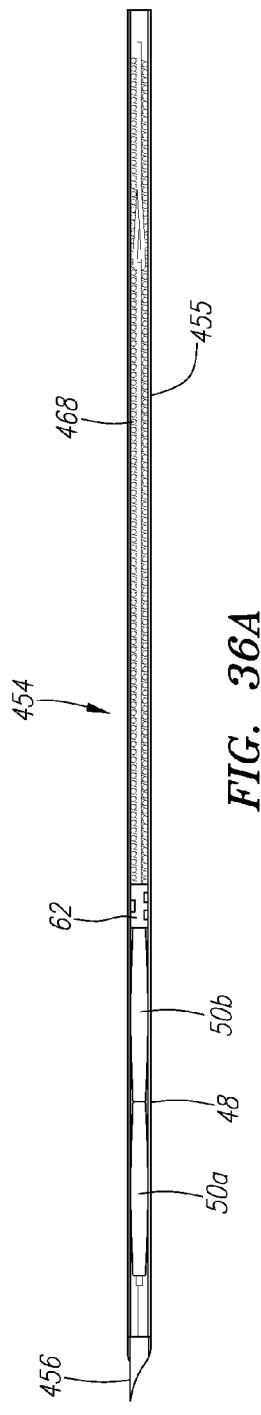
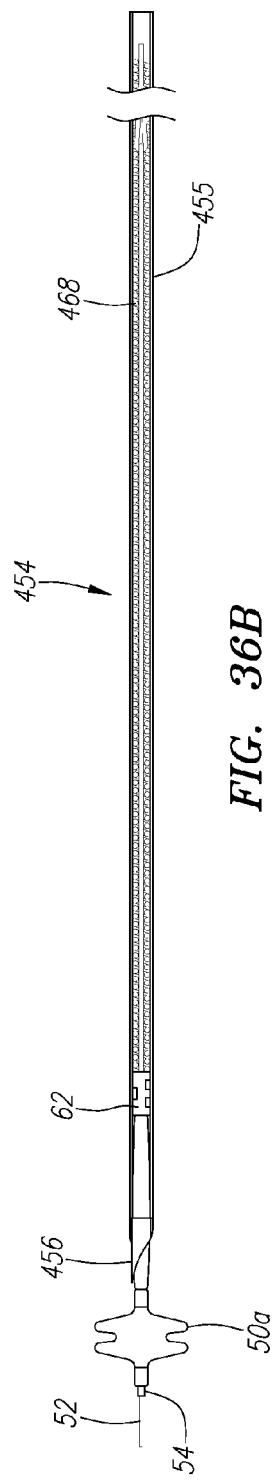
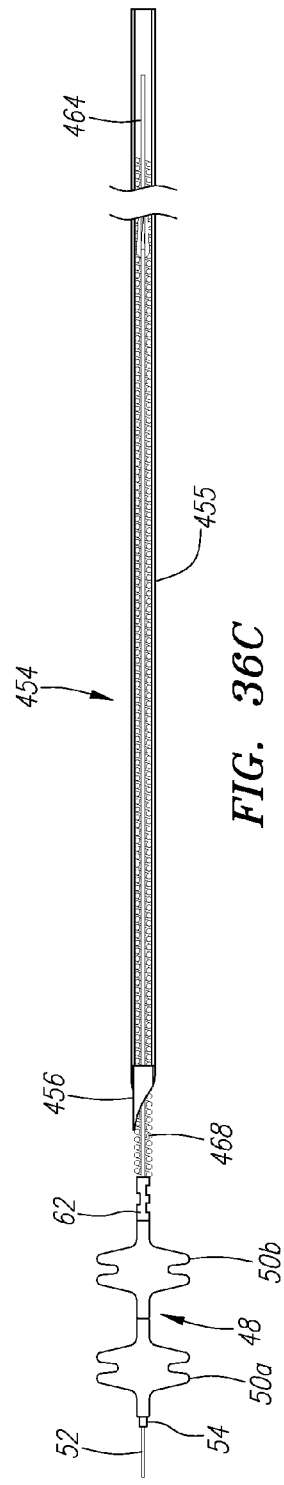

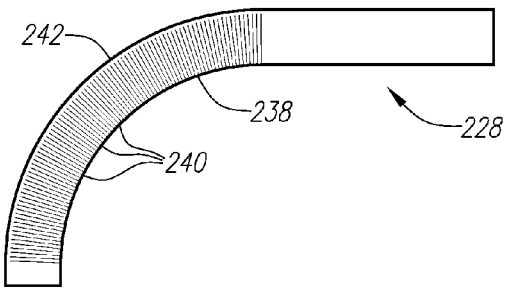
FIG. 37
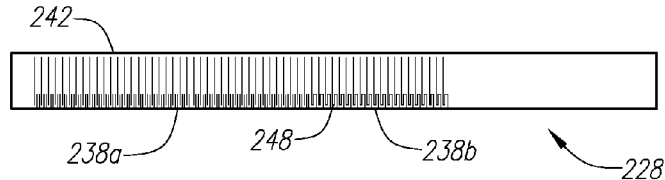
FIG. 38A
FIG. 38B
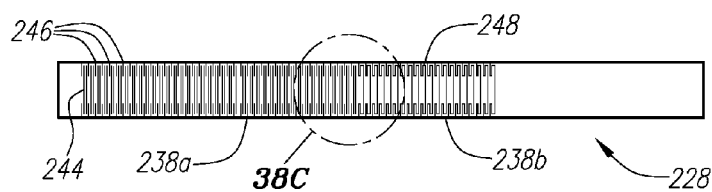
FIG. 38C
FIG. 39A
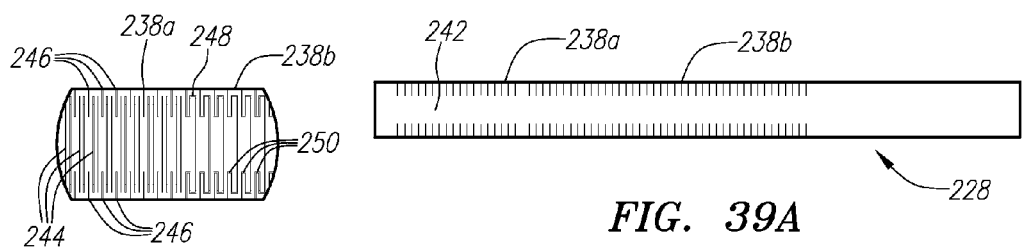
FIG. 39C
FIG. 39B

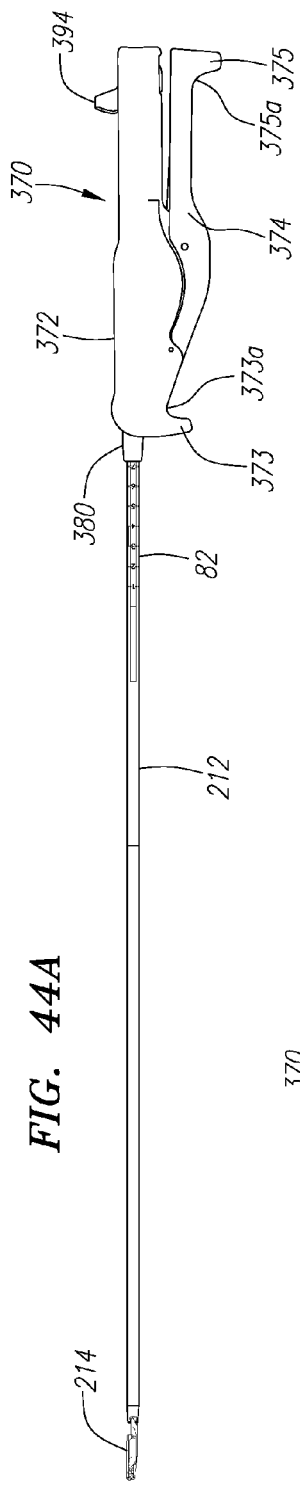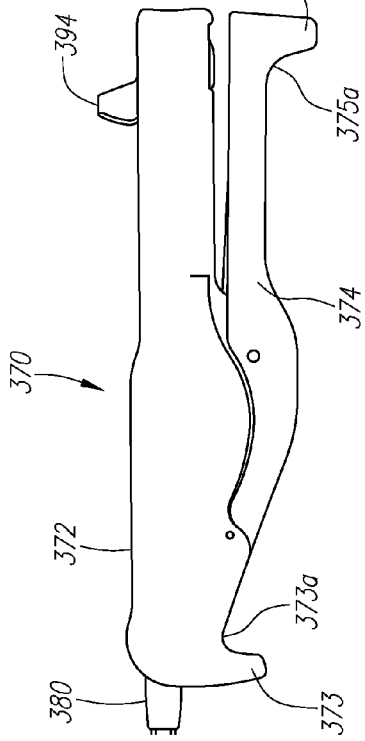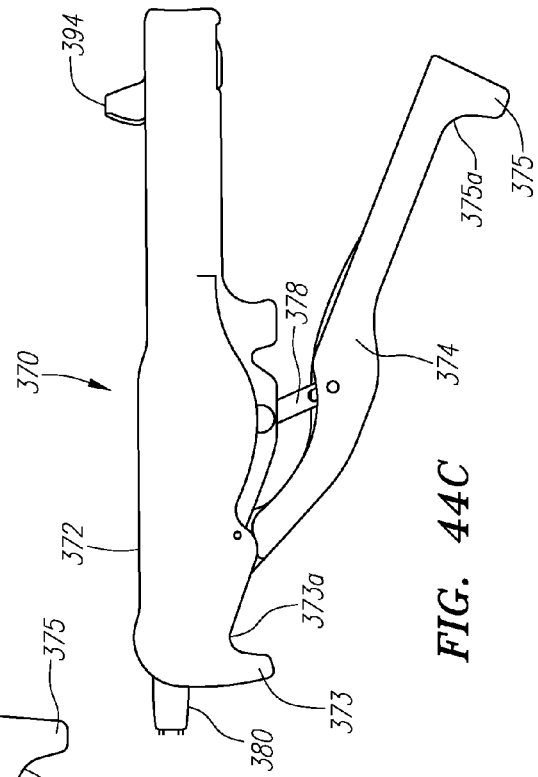
FIG. 44A
FIG. 44B
FIG. 44C

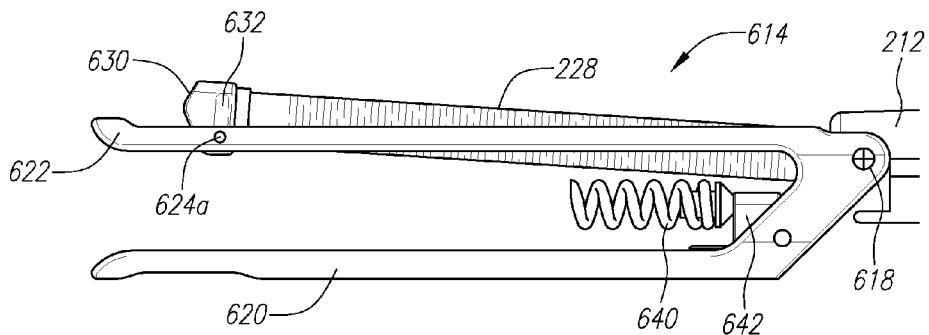
FIG. 45A
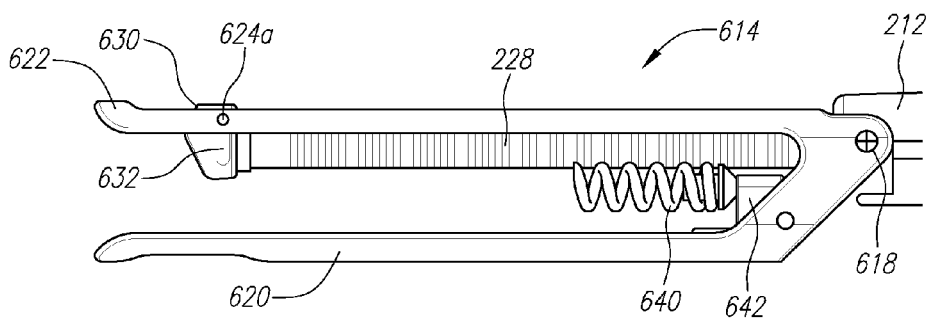
FIG. 45B
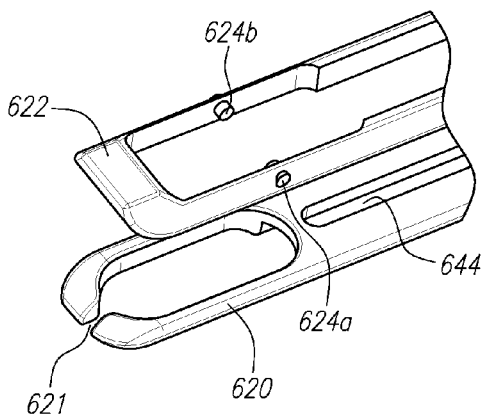
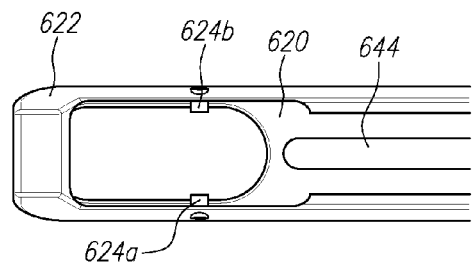
FIG. 46A
FIG. 46B

ENDOSCOPIC TISSUE ANCHOR DEPLOYMENT

RELATED APPLICATION DATA

This application claims priority to U.S. Provisional Patent Application No. 61/432,537 filed on Jan. 13, 2011. Application Nos. 61/432,537; 61/073,296; 61/172,169 and Ser. No. 12/486,578, are incorporated herein by reference.

BACKGROUND

This application relates to methods and apparatus for manipulating and/or securing tissue. More particularly, the present disclosure relates to methods and apparatus for manipulating and/or securing tissue endoscopically and/or endolumenally, for instance, to form tissue folds, to approximate regions of tissue, and/or to deploy tissue anchors.

A number of surgical techniques have been developed to treat various gastrointestinal disorders. One example of a pervasive disorder is morbid obesity. Conventional surgical treatment for morbid obesity typically includes, e.g., bypassing an absorptive surface of the small intestine, or reducing the stomach size. However, many conventional surgical procedures may present numerous life-threatening post-operative complications, and may cause atypical diarrhea, electrolytic imbalance, unpredictable weight loss and reflux of nutritious chyme proximal to the site of the anastomosis.

Furthermore, the sutures or staples that are often used in surgical procedures for gastrointestinal disorders typically require extensive training by the clinician to achieve competent use, and may concentrate significant force over a small surface area of the tissue, thereby potentially causing the suture or staple to tear through the tissue. Many of the surgical procedures require regions of tissue within the body to be approximated towards one another and reliably secured. The gastrointestinal lumen, for instance, includes four tissue layers, where the mucosa layer is the inner-most tissue layer followed by connective tissue, the muscularis layer, and where the serosa layer is the outer-most tissue layer.

One problem with conventional gastrointestinal reduction systems is that the anchors (or staples) should engage at least the muscularis tissue layer in order to provide a proper foundation. In other words, the mucosa and connective tissue layers typically are not strong enough to sustain the tensile loads imposed by normal movement of the stomach wall during ingestion and processing of food. In particular, these layers tend to stretch elastically rather than firmly hold the anchors (or staples) in position, and accordingly, the more rigid muscularis and/or serosa layer should ideally be engaged. This problem of capturing the muscularis or serosa layers becomes particularly acute where it is desired to place an anchor or other apparatus transesophageally rather than intra-operatively, since care must be taken in piercing the tough stomach wall not to inadvertently puncture adjacent tissue or organs.

One conventional method for securing anchors within a body lumen to the tissue is to utilize sewing devices to suture the stomach wall into folds. This procedure typically involves advancing a sewing instrument through the working channel of an endoscope and into the stomach and against the stomach wall tissue. The contacted tissue is then typically drawn into the sewing instrument where one or more sutures or tags are implanted to hold the suctioned tissue in a folded condition known as a plication. Another method involves manually creating sutures for securing the plication.

One of the problems associated with these types of procedures is the time and number of intubations needed to perform the various procedures endoscopically. Another problem is the time required to complete a plication from the surrounding tissue with the body lumen. In the period of time that a patient is anesthetized, procedures such as for the treatment of morbid obesity, revision of obesity procedures, or for GERD must be performed to completion. Accordingly, the placement and securement of the tissue plication should ideally be relatively quick and performed with a high degree of confidence.

Another problem with conventional methods involves ensuring that the staple, knotted suture, or clip is secured tightly against the tissue and that the newly created plication will not relax under any slack which may be created by slipping staples, knots, or clips. Other conventional tissue securement devices such as suture anchors, twist ties, crimps, etc. are also often used to prevent sutures from slipping through tissue. However, many of these types of devices are typically large and unsuitable for low-profile delivery through the body, e.g., transesophageally.

Moreover, when grasping or clamping onto or upon the layers of tissue with conventional anchors, sutures, staples, clips, etc., many of these devices are configured to be placed only after the tissue has been plicated and not during the actual plication procedure.

SUMMARY

In one general aspect, devices according to the present invention include mechanisms for deploying tissue anchors and tissue anchor assemblies into and/or through tissue within a patient. In some embodiments, the devices are introduced endolumenally (e.g., transorally, transanally, etc.) into the patient's body and into or around the gastrointestinal ("GI") tract. Once the instruments are positioned within the stomach or other target site, tissue at the target site is temporarily engaged or grasped and the engaged tissue is manipulated by a surgeon or practitioner from outside the patient's body.

In engaging, manipulating, and/or securing the tissue, various methods and devices may be implemented. For instance, tissue securement devices may be delivered and positioned via an endoscopic apparatus for contacting a tissue wall, creating one or more tissue folds, and deploying one or more tissue anchors through the tissue fold(s). The tissue anchor(s) may be disposed through the muscularis and/or serosa layers of the tissue. An endoscopic access device having an elongate body, a steerable distal portion, and multiple lumens defined therethrough may be advanced into a patient per-orally and through the esophagus. A tissue manipulation assembly positioned at the distal end of a tubular body may be passed through the endoscopic access device for engaging and securing the tissue.

Utilizing one or more of the instruments, the endoscopic access device may be used to pass the flexible body therethrough and into the stomach where it may be used to engage tissue and form folds, invaginations, or other reconfigurations of tissue which are secured via expandable tissue anchors expelled from the tissue manipulation assembly. Any number of tissue folds and/or invaginations, i.e., one or more, may be created.

In an embodiment, a delivery catheter is advanced through a patient's mouth and esophagus and into the patient's stomach or other target site, with the delivery catheter including a flexible tube having a needle at its distal end and with a first tissue anchor assembly being contained within the flexible tube of the delivery catheter. One or more instruments associated with the delivery catheter are used to form a first tissue fold in the tissue at the target site, the tissue fold preferably including a serosa-to-serosa contact of tissue on the peritoneal surface of the tissue. The needle of the delivery catheter is passed through the first tissue fold, and a first tissue anchor assembly is deployed from the delivery catheter through the first tissue fold to thereby secure the first tissue fold. A plurality of additional tissue folds may be also secured in the tissue.

In some embodiments, the devices and systems include an endoscopic access device, a tissue manipulation assembly, and a needle deployment assembly containing a tissue anchor or tissue anchor assembly. The tissue manipulation assembly includes a handle having several optional features and functions, including a handle stop member for preventing actuation of the handle under certain circumstances, a needle stop member for preventing advancement of the needle deployment assembly under certain circumstances, a pin and track mechanism that defines a series of handle actuation steps corresponding to deployment steps for the tissue manipulation assembly and the needle deployment assembly, and others.

BRIEF DESCRIPTION OF THE DRAWINGS

FIGS. 15A-C are perspective views of the needle deployment assembly of FIGS. 13A-B with the flexible catheter body removed for clarification.

FIG. 21 is a side view of another embodiment of an actuator mechanism for a tissue anchor delivery device.

FIGS. 22A-B are perspective views of the actuator mechanism of FIG. 21.

FIG. 23 is a side view of the actuator mechanism of FIG. 21 with a portion of the main housing removed for clarification.

FIG. 24 is a side view of the actuator mechanism of FIG. 21 with a portion of the main housing and handle body removed for clarification, shown in the fully closed position.

FIGS. 25A-B are side views of the actuator mechanism of FIG. 21 (with a portion of the main housing and handle body removed for clarification) including a needle deployment assembly being loaded into the proximal end of the device.

FIGS. 28A-C are side and top views of the actuator mechanism of FIG. 21 (with a portion of the main housing removed for clarification) including a needle deployment assembly being loaded into the proximal end of the device.

FIG. 32A is a side view of the needle deployment assembly of FIGS. 30A-C, with the outer sheath removed for clarification.

FIGS. 32B-C are side views of components of the needle deployment assembly of FIGS. 30A-C.

FIGS. 35A-C are cross-sectional views of a flexible catheter portion of the needle deployment assembly of FIGS. 30A-C.

FIGS. 36A-C are cross-sectional views of a flexible catheter portion of the needle deployment assembly of FIGS. 30A-C, showing the progress of a deployment of an anchor assembly.

FIG. 37 is a side view of an embodiment of a distal portion of a launch tube of the tissue anchor delivery device shown in FIG. 3.

FIGS. 38A-C are a bottom view, side view, and expanded bottom view, respectively, of another embodiment of a distal portion of a launch tube of the tissue anchor delivery device shown in FIG. 3.

FIGS. 39A-C are a top view, side view, and expanded side view, respectively, of another embodiment of a distal portion of a launch tube of the tissue anchor delivery device shown in FIG. 3.

FIG. 44A is a side view of another embodiment of a tissue manipulation assembly.

FIGS. 44B-C are side views of an actuator mechanism of the tissue manipulation assembly of FIG. 44A shown in a closed and an open position, respectively.

FIGS. 45A-B are side views of an alternative embodiment of a distal end effector.

FIGS. 46A-B are a perspective and a top view, respectively, of the upper and lower fixed bails of the distal end effector shown in FIGS. 45A-B.

DETAILED DESCRIPTION

Figure 1A:
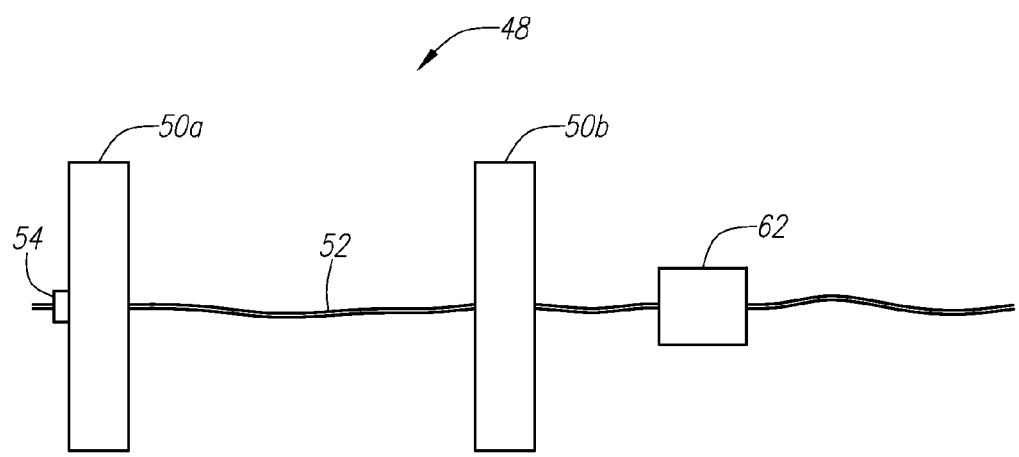
FIG. 1A is a schematic representation of a tissue anchor assembly.

Endoscopic and endolumenal surgical methods and devices are described herein. In several embodiments, the methods entail performing surgery through a patient's mouth or other natural orifices, reducing or eliminating the need for external incisions into the body. Operating through the body's natural orifices offers promise for faster healing times, less scarring and less pain which could lead to reduced hospitalization and quicker recovery.

USGI Medical, Inc. of San Clemente, Calif. has developed several devices and methods that facilitate endoscopic and endolumenal diagnostic and therapeutic procedures. Several endoscopic access devices are described, for example, in the following United States patent applications:

TABLE 1

| U.S. patent application Ser. No. | Filing Date |
| --- | --- |
| 10/346,709 | Jan. 15, 2003 |
| 10/458,060 | Jun. 9, 2003 |
| 10/797,485 | Mar. 9, 2004 |
| 11/129,513 | May 13, 2005 |
| 11/365,088 | Feb. 28, 2006 |
| 11/738,297 | Apr. 20, 2007 |
| 11/750,986 | May 18, 2007 |
| 12/061,591 | Apr. 2, 2008 |

Several tissue manipulation and tissue anchor delivery devices are described in the following United States patent applications:

TABLE 2

| U.S. patent application Ser. No. | Filing Date |
| --- | --- |
| 10/612,109 | Jul. 1, 2003 |
| 10/639,162 | Aug. 11, 2003 |
| 10/672,375 | Sept. 26, 2003 |
| 10/734,547 | Dec. 12, 2003 |
| 10/734,562 | Dec. 12, 2003 |
| 10/735,030 | Dec. 12, 2003 |
| 10/840,950 | May 7, 2004 |
| 10/955,245 | Sept. 29, 2004 |
| 11/070,863 | Mar. 1, 2005 |

Endolumenal tissue grasping devices are described in several of the United States patent applications listed above, and in the following United States patent applications:

TABLE 3

| U.S. patent application Ser. No. | Filing Date |
| --- | --- |
| 11/736,539 | Apr. 17, 2007 |
| 11/736,541 | Apr. 17, 2007 |

Tissue anchors are described in several of the United States patent applications listed above, and in the following United States patent applications:

TABLE 4

| U.S. patent application Ser. No. | Filing Date |
| --- | --- |
| 10/841,411 | May 7, 2004 |
| 11/404,423 | Apr. 14, 2006 |
| 11/773,933 | Jul. 5, 2007 |

Each of the foregoing patent applications is hereby incorporated by reference in its entirety.

Several endoscopic and/or endolumenal therapeutic procedures described in the above patent applications include the steps of grasping tissue to form a tissue fold and deploying or implanting a fold retaining device (e.g., a tissue anchor assembly) that is used to maintain the fold. Other such procedures include the steps of grasping at least two sections of tissue, approximating the at least two sections of tissue, and deploying or implanting a tissue retaining device (e.g., a tissue anchor assembly) that is used to maintain the at least two sections of tissue in their approximated state. For simplicity, the discussion herein will describe tissue anchor assemblies holding tissue folds, with it being understood that other portions or sections of tissue that do not constitute tissue folds are suitably retained by the tissue anchor assemblies. The following sections include descriptions of several embodiments of devices that are suitable for performing these and other endoscopic and/or endolumenal surgical procedures.

A tissue anchor assembly is used to maintain a tissue fold in tissue such as that present in the gastrointestinal lumen. Suitable tissue anchor assemblies include tissue anchors such as those described in several of the United States Patent Applications incorporated by reference above, including Ser. Nos. 10/841,411, 11/404,423, and 11/773,933. A schematic representation of a suitable tissue anchor assembly 48 is shown in FIG. 1A.

Figure 1B:
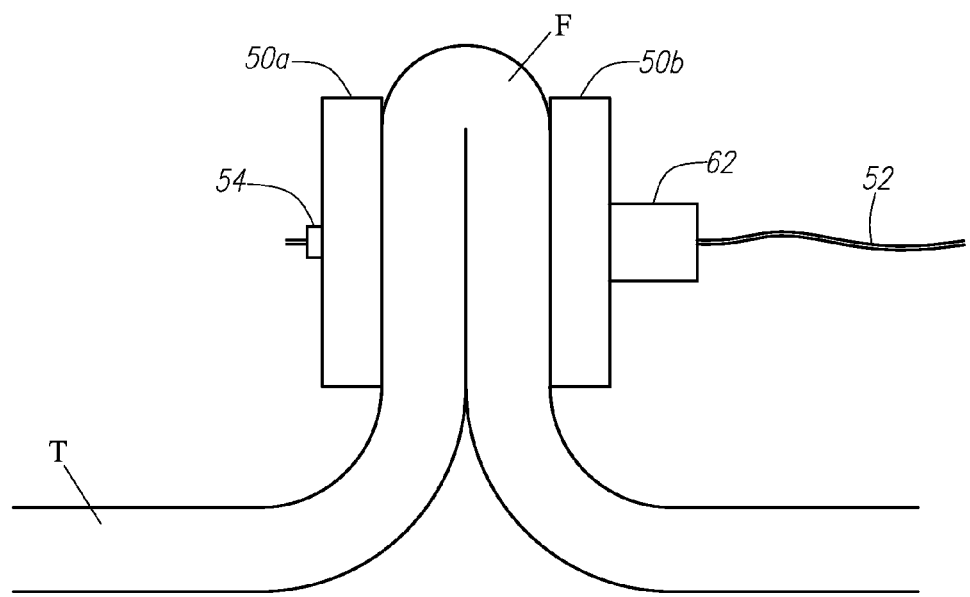
FIG. 1B is a schematic representation of a tissue anchor assembly securing a tissue fold.

Preferably, the tissue anchor assemblies include a pair of tissue anchors 50a, 50b slidably retained by a connecting member, such as a suture 52. A locking mechanism, such as a cinch 62, is also slidably retained on the suture 52. The cinch 62 is configured to provide a cinching force against the anchors 50a, 50b in order to impart a tension force on the suture. Accordingly, the tissue anchor assembly 48 is adapted to hold a fold F of tissue T, as shown in FIG. 1B.

Figure 2A:
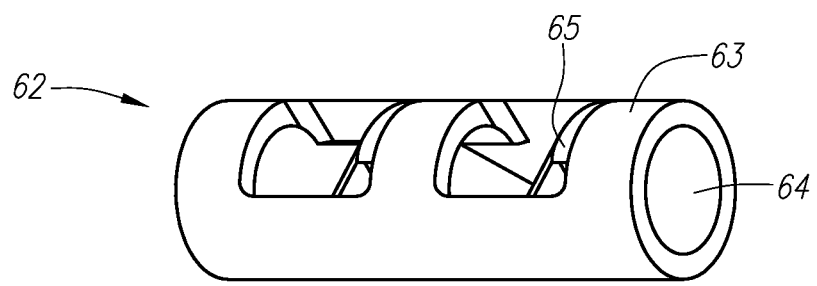
FIG. 2A is a perspective view of a cinch.
Figure 2B:
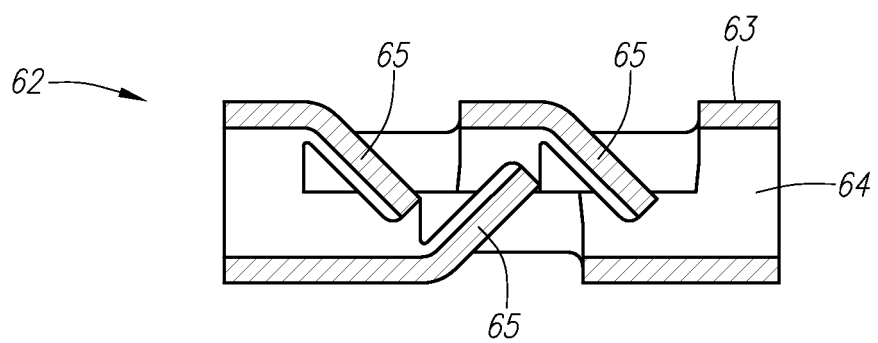
FIG. 2B is a cross-sectional view of the cinch of FIG. 2A.

The cinch 62 functions by providing unidirectional translation over the suture thereby providing the ability to advance the tissue anchor(s) 50 into apposition and to retain the anchor(s) in place. An embodiment of a cinch 62 is shown in FIGS. 2A-B. The cinch includes a generally tubular body 63 defining an internal lumen 64. A plurality of inwardly facing levers 65 are formed integrally with the side wall of the tubular body 63. Three levers 65 are included in the cinch embodiment shown in the figures. In other embodiments, fewer levers (e.g., one or two) or more than three levers are used. In some embodiments, each lever 65 is flexibly biased to spring radially inward into the tubular body 63 or to deflect radially outward upon a suture 52 or other connector member passing therethrough. During translation of the suture 52 in a first direction (i.e., from left to right as viewed in FIG. 2B), the suture 52 is allowed to freely pass through the tubular body and past the plurality of levers due to a slight radially outward pivot of each of the levers. However, when the suture is urged in the second direction (i.e., from right to left as viewed in FIG. 2B), the levers 65 pivot radially inward, cinching down upon the suture against the inner surface of the tubular body 63. The cinching levers 65 are configured to prevent or inhibit the overcinching or cutting of the suture 52.

In other embodiments of the cinch 62, the levers 65 are substantially rigid, and do not pivot or deflect. In those embodiments, the levers 65 create a sufficiently tortuous path for the suture 52 (or other connector) to traverse that the cinch effectively binds the suture from translating in the first direction, while allowing translation in the second direction.

The cinches 62 described herein are formed of biocompatible and/or bioabsorbable materials such as those described above. In several embodiments, the cinch is formed of nickel-titanium alloy (Nitinol). The size and shape of the cinch are primarily dependent upon the size and shape of the other parts of the tissue anchor assembly, such as the diameter and materials forming the suture 52 (or other connector) and/or the size of the passage in the tissue anchors 50. Additional embodiments of cinches and additional cinching mechanisms suitable for use in the tissue anchor assemblies 48 are described and illustrated in U.S. patent application Ser. Nos. 10/612,170; 10/840,950; 10/840,951; 10/841,245; 10/841,411; 10/865,736; 11/036,866; 11/036,946; and 11/404,423, each of which is hereby incorporated by reference in its entirety (including all references cited therein) as if fully set forth herein.

Figure 3:
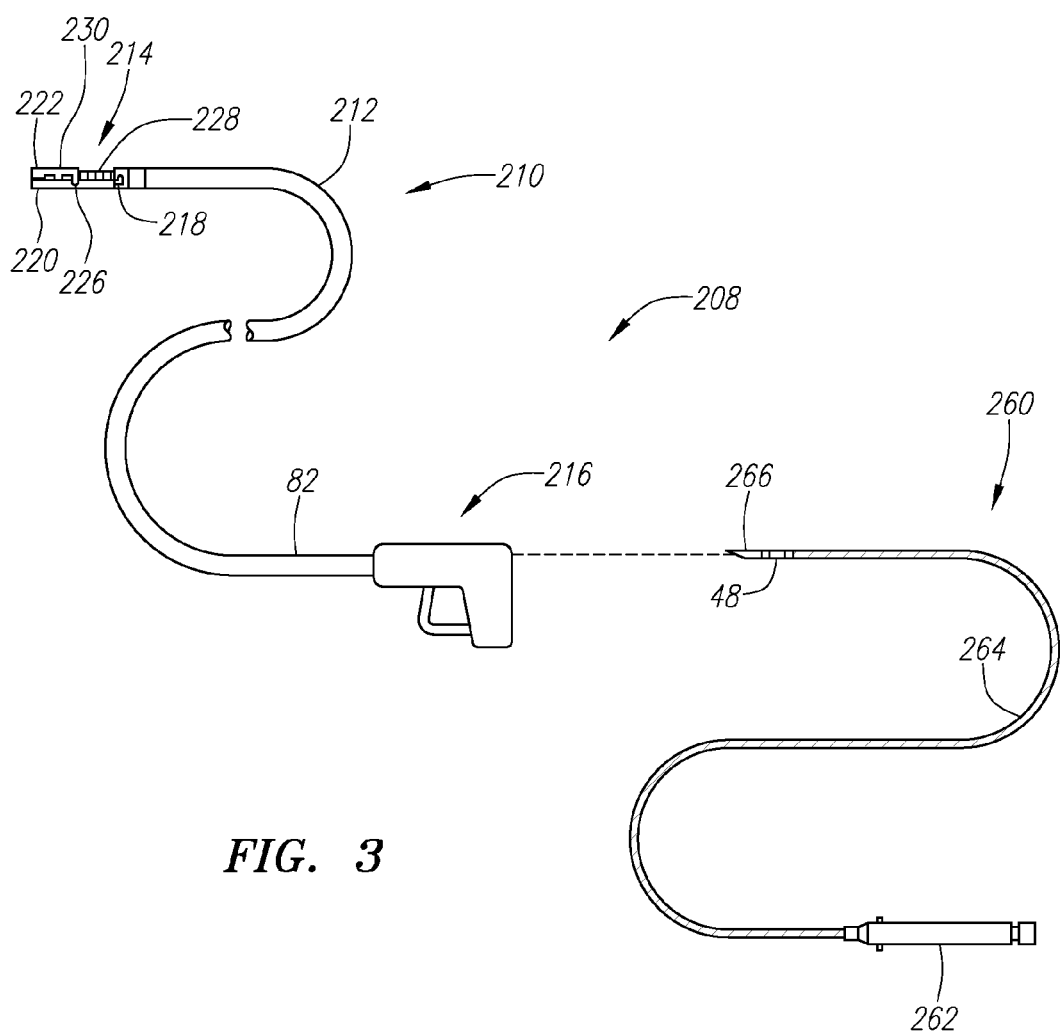
FIG. 3 is a side view of a tissue anchor delivery device, including a tissue manipulation assembly and a needle deployment assembly.

In several embodiments, a delivery device is used to deploy the tissue anchors and tissue anchor assemblies 48 endoscopically or endolumenally. An example of a suitable delivery device is shown in FIG. 3, and is described in more detail in U.S. patent application Ser. No. 11/070,846, which is hereby incorporated by reference in its entirety (including all references cited therein) as if fully set forth herein. The delivery device 208 is described briefly below.

In manipulating tissue or creating tissue folds, a device having a distal end effector may be advanced endoscopically or endolumenally, e.g., transorally, transgastrically, etc., into the patient's body, e.g., the stomach. The tissue may be engaged or grasped and the engaged tissue may be manipulated by a surgeon or practitioner from outside the patient's body. Examples of creating and forming tissue plications are described in further detail in U.S. patent application Ser. No. 10/955,245, filed Sep. 29, 2004, which is incorporated herein by reference, as well as U.S. patent application Ser. No. 10/735,030, filed Dec. 12, 2003, which is also incorporated herein by reference in its entirety.

In engaging, manipulating, and/or securing the tissue, various methods and devices may be implemented. For instance, tissue securement devices may be delivered and positioned via an endoscopic apparatus for contacting a tissue wall of the gastrointestinal lumen, creating one or more tissue folds, and deploying one or more tissue anchors through the tissue fold(s). The tissue anchor(s) may be disposed through the muscularis and/or serosa layers of the gastrointestinal lumen.

Figure 4:
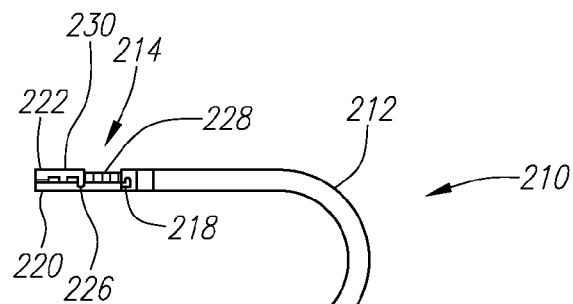
FIG. 4 is a side view of the tissue manipulation assembly of FIG. 3.

The delivery device 208 shown in FIG. 3 generally comprises a tissue manipulation assembly 210 and a needle deployment assembly 260. The tissue manipulation assembly 210 is also shown in FIG. 4. The tissue manipulation assembly 210 includes a flexible catheter or tubular body 212 which is configured to be sufficiently flexible for advancement into a body lumen, e.g., transorally, percutaneously, laparoscopically, etc. The tubular body 212 is configured to be torqueable through various methods, e.g., utilizing a braided tubular construction, such that when a handle 216 is manipulated and/or rotated by a practitioner from outside the patient's body, the longitudinal and/or torquing force is transmitted along the body 212 such that the distal end of the body 212 is advanced, withdrawn, or rotated in a corresponding manner.

For example, in some embodiments, the tubular body 212 has a composite construction that includes a first layer or multiple layers of braided wire or mesh and a second layer or multiple layers of a polymeric material such as polyurethane, nylon, polyester, Pebax (polyether block amide), or the like. An optional inner liner of polytetraflouroethylene (PTFE) may be provided to seal and/or to improve friction characteristics. The physical properties (e.g., hardness, stiffness) of a composite construction tubular body 212 will vary depending upon the materials used, the specific construction, and other factors.

In some embodiments, the tubular body 212 includes a proximal section having a first hardness and/or stiffness, and a distal section having a second hardness and/or stiffness that is lower than the hardness and/or stiffness of the proximal section. In these embodiments, the proximal section corresponds with a portion of the tubular body 212 that traverses a relatively non-tortuous path (e.g., through the relatively straight esophagus), and the distal section corresponds with a portion of the tubular body 212 that traverses a relatively tortuous path (e.g., bending regions of the tubular body or endoscopic access device that are guided or steered to reach portions of the stomach, colon, peritoneum, etc.). In this way, the tubular body 212 provides improved maneuverability during deployment, either as a standalone instrument or as deployed through a channel of an endoscopic access device. In particular, a distal section having a relatively lower hardness and/or stiffness will provide an improved capability to be rotated around its longitudinal axis within the channel of an endoscopic access device in comparison to a distal section having a relatively higher hardness and/or stiffness.

In a preferred embodiment, the proximal and distal sections are each formed as composite tubes including an inner liner of PTFE, a layer of stainless steel wire braid, and a layer of Pebax block copolymer. The proximal section includes a braid wire formed from round wire having a diameter of from about 0.004" to about 0.008" and having from about 30 picks per inch ("ppi") to about 60 ppi, and a layer of Pebax having a Shore D hardness of from about 30 to about 45, and/or a flexural modulus (ASTM D 790) of from about 72 MPa to about 87 MPa. The distal section includes a braid wire formed from round wire having a diameter of from about 0.004" to about 0.008" and having from about 45 ppi to about 75 ppi, and a layer of Pebax having a Shore D hardness of from about 20 to about 35, and/or a flexural modulus (ASTM D 790) of from about 15 MPa to about 28 MPa. Those skilled in the art will recognize that other combinations of materials, material properties, and constructions of the tubular body 212 are possible. Moreover, those skilled in the art will recognize that sections additional to the proximal section and distal section may be added, with each section having different performance characteristics, in order to obtain desired performance.

Figure 5A:
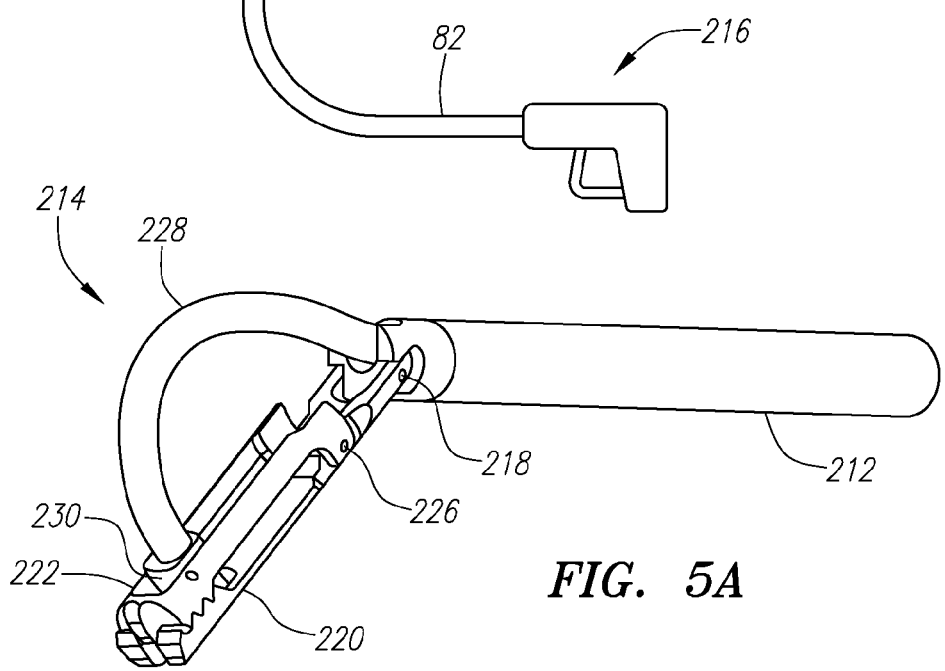
FIGS. 5A and 5B are perspective views of an end effector of the tissue manipulation assembly of FIGS. 3 and 4.
Figure 5B:
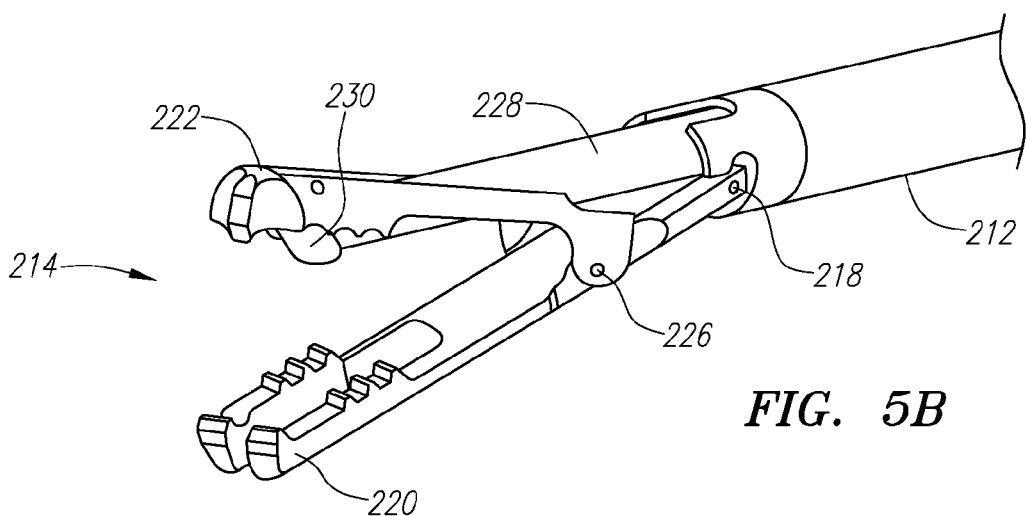

A tissue manipulation end effector 214 is located at the distal end of the tubular body 212 and is generally used to contact and form tissue folds and/or to otherwise bring portions of tissue into apposition. The end effector is also shown in FIGS. 5A and 5B. The tissue manipulation end effector 214 is connected to the distal end of the tubular body 212 via a pivotable coupling 218. A lower jaw member 220 extends distally from the pivotable coupling 218 and an upper jaw member 222, in this example, is pivotably coupled to the lower jaw member 220 via a jaw pivot 226. The location of the jaw pivot 226 may be positioned at various locations along the lower jaw 220 depending upon a number of factors, e.g., the desired size of the "bite" or opening for accepting tissue between the jaw members, the amount of closing force between the jaw members, etc. One or both jaw members 220, 222 may also have a number of protrusions, projections, grasping teeth, textured surfaces, etc. on the surface or surfaces of the jaw members 220, 222 facing one another to facilitate the adherence of tissue between the jaw members 220, 222.

Figure 43A:
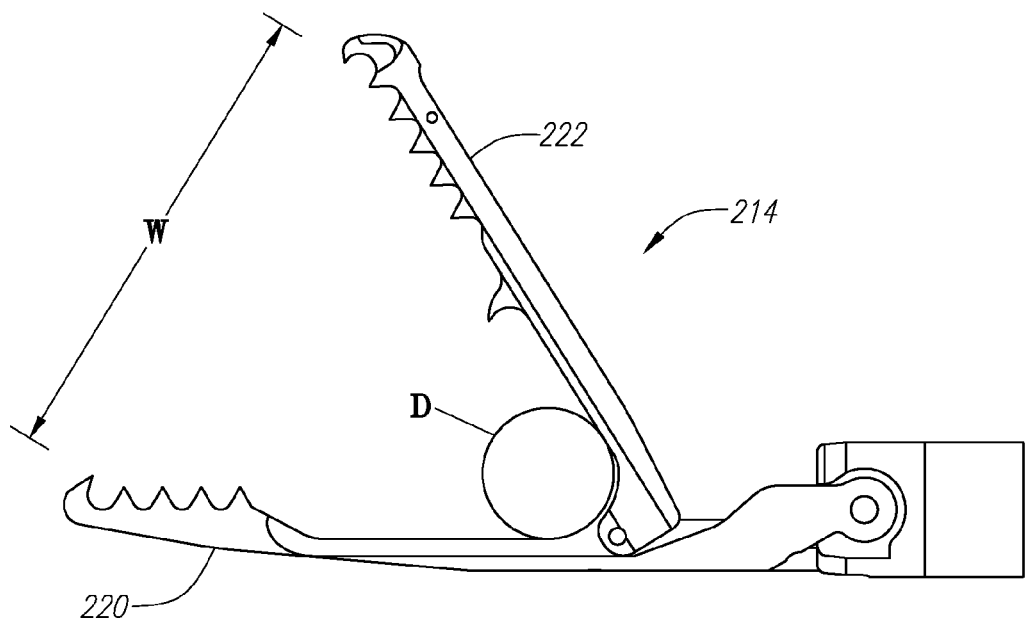
FIGS. 43A-B are side views of the end effectors shown in FIGS. 41A-C and 42A-D, respectively.
Figure 43B:
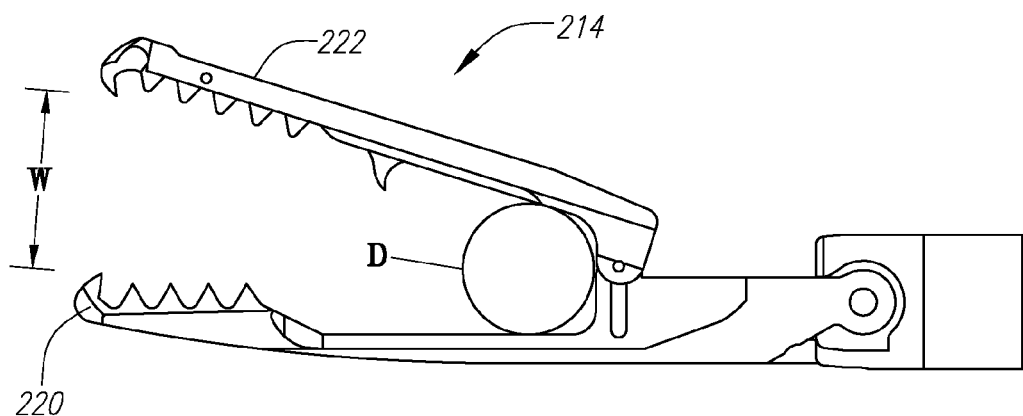
Figure 47A:
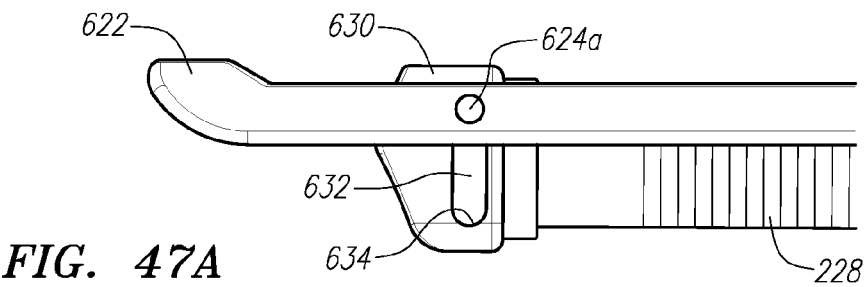
FIGS. 47A-B are side views of the upper fixed bail, launch tube, and pivot of the distal end effector shown in FIGS. 45A-B.
Figure 47B:
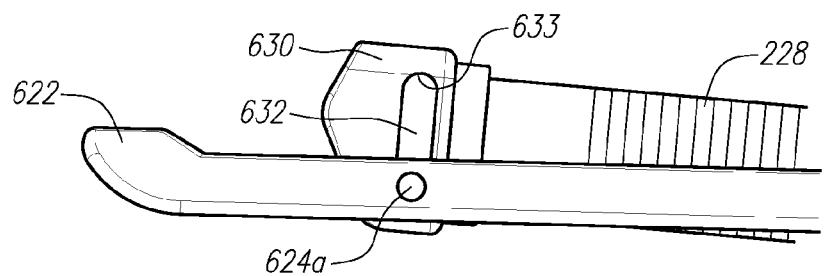

Turning to FIGS. 41A-C and 42A-D, two additional embodiments of the tissue manipulation end effector 214 are shown. For clarity, the tubular body 212 and launch tube 228 are not shown in the drawings. In the embodiment shown in FIGS. 41A-C, the upper jaw 222 is pivotably coupled to the lower jaw 220 via a jaw pivot 226 that is fixedly attached to the lower jaw 220, as described above in relation to FIGS. 5A-B. In the embodiment shown in FIGS. 42A-D, a slotted jaw construction includes a jaw pivot 226 that is able to slide within an upright slot 232 formed in the frame of the lower jaw 220. In an alternative embodiment not shown, the jaw pivot 226 is fixed to the lower jaw 220 and slides within a slot 232 formed on the frame of the upper jaw 222. The capability of the jaw pivot 226 to slide within the upright slot 232 provides the end effector 214 with adjustable jaw geometries to better accommodate tissue folds (or other targets) having a wider range of sizes. For example, as shown by the illustrations in FIGS. 43A-B, the end effector 214 embodiment having the upright slot 232 (shown in FIG. 43B) is able to accommodate a comparably-sized target having a size "D" located at the vertex between the upper jaw 222 and lower jaw 220 without having to be opened as widely "W" as is necessary with the end effector 214 embodiment that does not have the upright slot (shown in FIG. 43A).

Those skilled in the art will recognize that the slotted jaw construction described above and shown in FIGS. 42A-D and 43B is adaptable for use in other endoscopic instruments (or non-endoscopic instruments) having a pair of jaws oriented to grasp, trap, or engage tissue or other materials between the jaws. For example, the slotted jaw construction may be adapted for use with an endoscopic stapling device in order to provide improved orientation between an upper staple cartridge and a lower anvil portion of the device. Other uses of the slotted jaw construction are also possible.

Returning to FIGS. 3-7, a launch tube 228 extends from the handle 216, through the tubular body 212, and distally from the end of the tubular body 212 where a distal end of the launch tube 228 is pivotally connected to the upper jaw member 222 at a launch tube pivot 230. A distal portion of the launch tube 228 may be pivoted into position within a channel or groove defined in upper jaw member 222, to facilitate a low-profile configuration of tissue manipulation end effector 214. When articulated, either via the launch tube 228 or other mechanism, the jaw members 220, 222 may be urged into an open configuration to receive tissue in the opening between the jaw members 220, 222. (See, e.g., FIG. 5B).

The launch tube 228 may be advanced from its proximal end at the handle 216 such that the portion of the launch tube 228 that extends distally from the body 212 is forced to rotate at a hinge or pivot 230 and reconfigure itself such that the exposed portion forms a curved or arcuate shape that positions the launch tube opening perpendicularly relative to the upper jaw member 222. (See, e.g., FIG. 5A). The launch tube 228, or at least the exposed portion of the launch tube 228, may be fabricated from a highly flexible material or it may be fabricated, e.g., from Nitinol tubing material which is adapted to flex, e.g., via circumferential slots, to permit bending.

For example, turning to FIGS. 37, 38A-C, 39A-C, and 40A-B, four embodiments of a flexible distal portion 238 of a launch tube 228 are shown. In the first embodiment, shown in FIG. 37, a plurality of substantially uniformly spaced circumferential slots 240 are formed over the distal portion 238. In the embodiment, each of the circumferential slots 240 is of a substantially uniform length, with each extending radially around greater than 50% of the circumference of the launch tube. In some embodiments, the circumferential slots extend radially around the circumference of the launch tube by up to about 85% of the circumference and, in still other embodiments, the circumferential slots extend around the launch tube by up to about 90% of the circumference. A spine 242—i.e., the unslotted longitudinal section of the distal portion 238 of the launch tube—is defined along the length of the distal portion 238. In some embodiments, the spine has a width of between about 10% to about 15% or more of the circumference of the launch tube. As shown in FIG. 37, the size, shape, pattern, and orientation of the circumferential slots 240 and the spine 242 cause the distal portion 238 to flex and to effectively lock out at a predetermined position when a distally-oriented force is applied to the proximal end of the launch tube 228. The material, diameter, and wall thickness of the distal portion 238 of the launch tube also contribute to the degree of flex and predetermined lock out position. The predetermined lock-out position provides a relatively high degree of planar stability to the distal region 238 of the launch tube when it is in the flexed condition.

The launch tube distal region 238 embodiment shown in FIGS. 38A-C includes two regions 238a, 238b, each having a plurality of circumferential slots 240 formed in a pattern different from the other. In the first region 238a, located near the distal end of the distal portion 238, the circumferential slots include an alternating pattern including adjacent pairs of central semi-circumferential slots 244 centered upon the bending radius of the launch tube distal region 238. Each adjacent pair of central semi-circumferential slots 244 is separated by a pair of outer semi-circumferential slots 246. Each of the central slots 244 and outer slots 246 has a length of slightly less than 50% of the circumference of the distal region 238 of the launch tube. The resulting pattern is substantially in the form of a repetition of two longitudinally-aligned central slots 244 following by two radially aligned outer slots 246 along the length of the first region 238a. In the second region 238b, located just proximally of the first region 238a, the circumferential slots include a right-angle zigzag pattern 248 including nine adjoining segments each defining a right angle with its adjoining sections. The right-angle zigzag pattern 248 defines a plurality of longitudinally aligned keyed segments 250 on each side of the central bending radius of the launch tube distal region 238. The keyed segments 250 serve an additional function of substantially inhibiting over-extension in the reverse direction of the predetermined bending position, which may permanently deform or otherwise damage the distal region 238 of the launch tube.

Turning next to FIGS. 39A-C, the launch tube distal region 238 shown there includes a first region 238a having the identical circumferential slot pattern described above in relation to the first region 238a of the launch tube shown in FIGS. 38A-C, including central slots 244 and outer slots 246. The second region 238b includes slots defining a modified zigzag pattern 252 that includes at least two diagonal segments of the nine slot segments making up the modified zigzag pattern. The modified zigzag pattern 252 defines a plurality of longitudinally aligned keyed segments 254 on each side of the central bending radius of the launch tube distal region 238. The keyed segments 254 serve an additional function of substantially inhibiting over-extension in the reverse direction of the predetermined bending position, which may permanently deform or otherwise damage the distal region 238 of the launch tube.

Figures 40A, 40B:
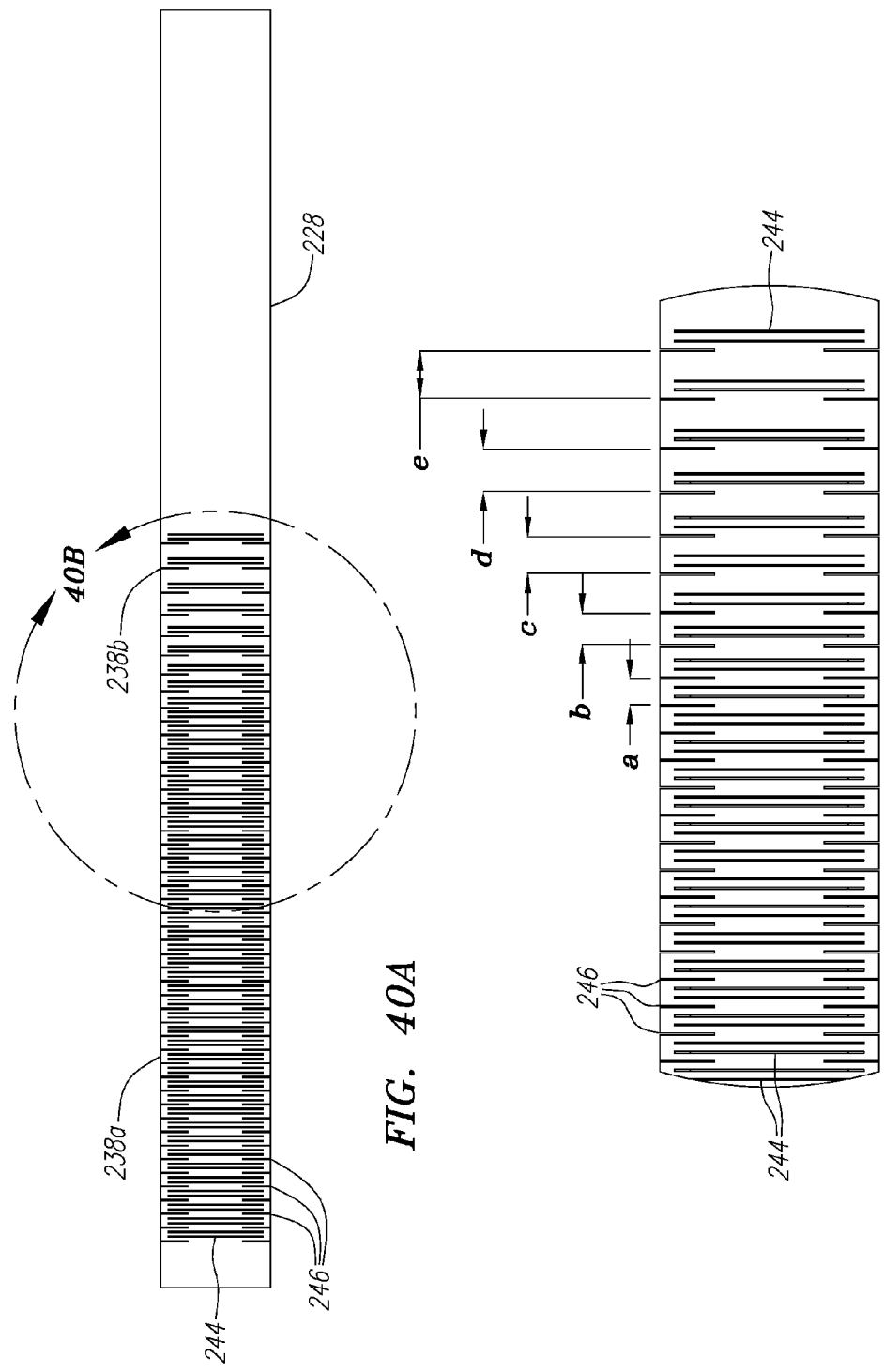
FIGS. 40A-B are a bottom view and expanded bottom view, respectively, of another embodiment of a distal portion of a launch tube of the tissue anchor delivery device shown in FIG. 3.
Figure 41A:
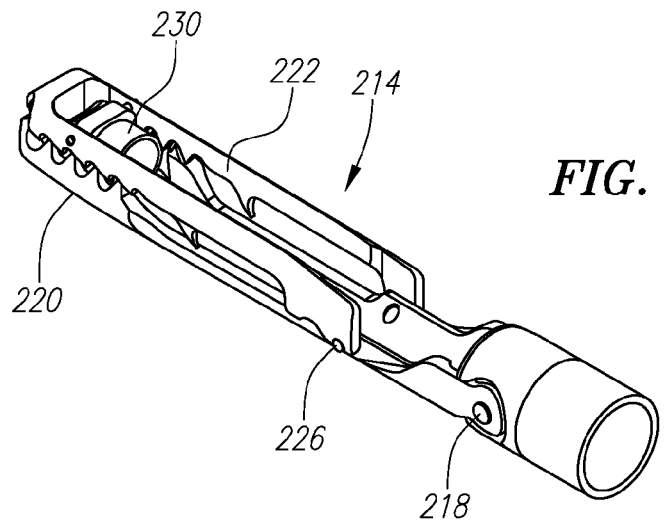
FIGS. 41A-C are a perspective view and two side views, respectively, of an embodiment of an end effector of the tissue anchor delivery device shown in FIG. 3.
Figure 41B:
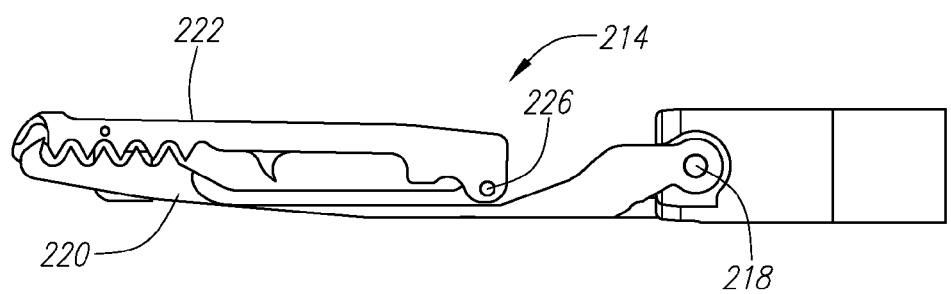
Figure 41C:
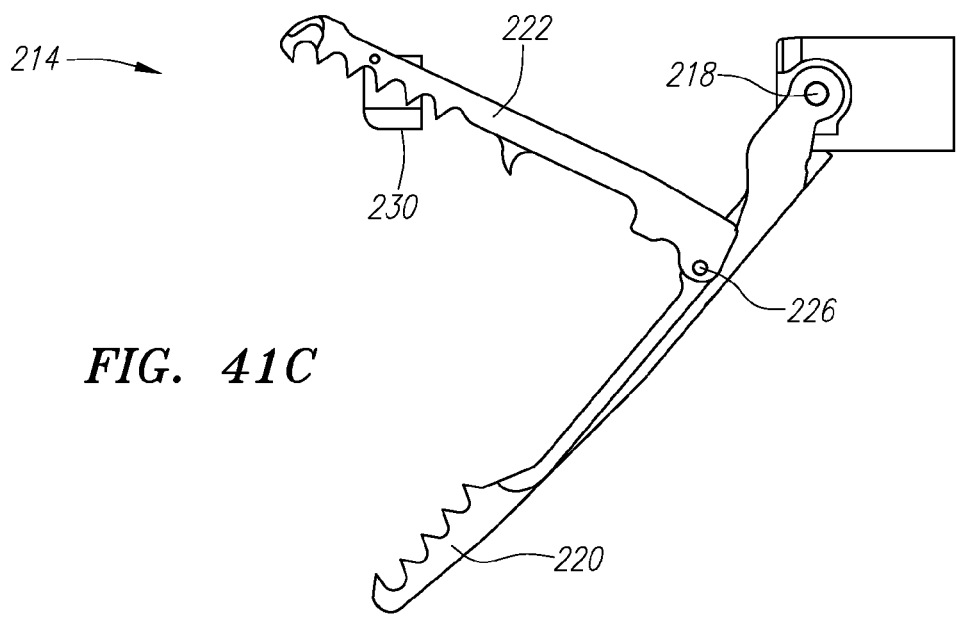
Figure 42A:
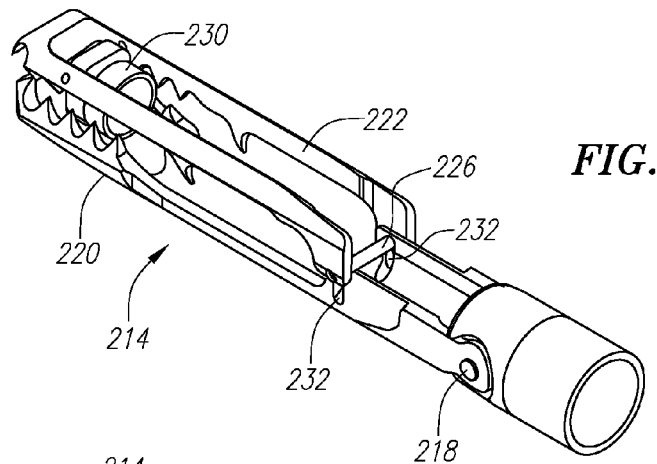
FIGS. 42A-D are a perspective view and three side views, respectively, of another embodiment of an end effector of the tissue anchor delivery device shown in FIG. 3.
Figure 42B:
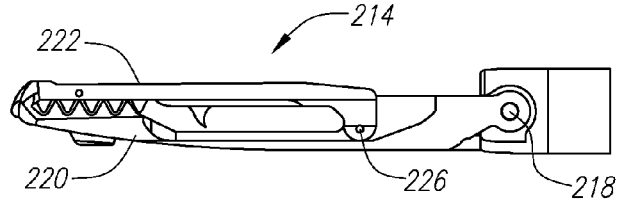
Figure 42C:
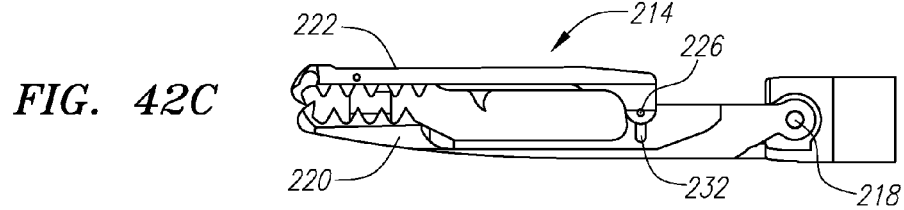
Figure 42D:
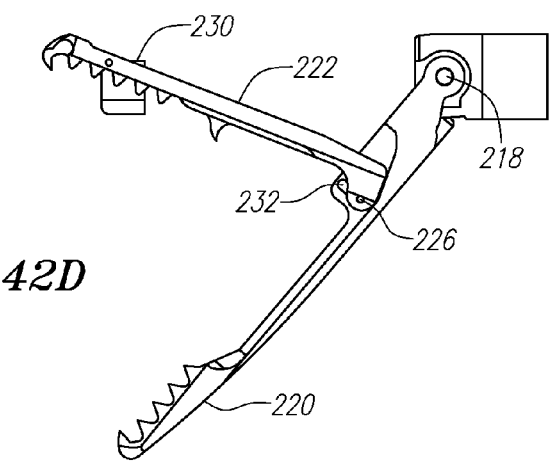

Finally, turning to FIGS. 40A-B, the launch tube distal region 238 shown there includes a first region 238a also having the identical circumferential slot pattern described above in relation to the first region 238a of the launch tube embodiments shown in FIGS. 38A-C and 39A-C, including central slots 244 and outer slots 246. The second region 238b also includes alternating central slots 244 and outer slots 246, but the alternating pattern includes slots that are spaced further apart longitudinally as the pattern progresses toward the proximal end. A representative example of the pattern spacing is shown in FIG. 40B, in which the relationships between the illustrated dimensions are a<b<c<d<e.

In the embodiments described above, a distal end of the launch tube 228 is pivotally connected to the upper jaw member 222 at a launch tube pivot 230. The launch tube pivot 230 is pivotable around an axis defined by a pin that is attached to the upper jaw member 222 and that extends through a hole in the pivot 230. In several other embodiments, shown in FIGS. 45A-B through 48A-B, an alternative pivot 630 is provided that is capable of ranges of motion in addition to pivoting relative to the upper jaw member 222. For example, FIGS. 45A-B through 48A-B show alternative embodiments of an end effector 614 that includes a lower bail 620 having a distal slot 621 and an upper bail 622 having a distal slot 623. The lower bail 620 and upper bail 622 are maintained in a fixed spatial relationship relative to one another and are connected to the tubular body 212 by a pivotable coupling 618. A helical grasper 640 having a tissue piercing tip is movably retained within a slider 642 that slides in a slot 644 formed in the lower fixed bail 620. The helical grasper 640 includes a shaft 641 that extends proximally to the handle 216 of the anchor delivery device 208, where it is actuable by the user. (See also FIGS. 50A-B). The helical grasper 640 is able to be moved proximally and distally under the control of the user, as guided by the slider 642. In this way, the helical grasper 640 may be used to grasp tissue and retract the tissue into the space defined between the lower fixed bail 620 and the upper fixed bail 622.

A pivot 630 is pivotably and slidably connected to the upper fixed bail 622 via a pair of pivot pins 624a, 624b that are formed on the upper fixed bail 622. The pivot pins 624a, 624b are formed on opposing sides of a slot defined by the upper fixed bail 622, and define a pivot axis about which the pivot 630 is able to rotate. In a first embodiment, shown in FIGS. 45A-B and 47A-B, the pivot 630 includes two pivot slots 632 formed on opposite sides of the external surface of the pivot. Each pivot slot 632 has an elongated shape defined by a pivot slot upper end 633 and a pivot slot lower end 634. The pivot 630 has a width that is slightly less than the width of the slot defined in the upper fixed bail 622. Accordingly, the pivot pins 624a, 624b are able to reside within the spaces defined by the pivot slots 632 formed on each side of the pivot 630. In this way, the pivot 630 is able to rotate (pivot) around the axis defined by the pivot pins 624a, 624b, and the body of the pivot 630 is also able to slide relative to the axis defined by the pivot pins 624a, 624b a distance defined by the length of the pivot slots 632. In this way, the pivot 630 may be rotated around the axis defined by the pivot pins 624a, 624b, and/or the pivot 630 may be moved into and out of the space between the lower fixed bail 620 and upper fixed bail 622 and/or proximally and distally relative to axis defined by the pivot pins 624a, 624b (depending upon the orientation of the pivot 630 relative to the upper fixed bail 622).

Figure 48A:
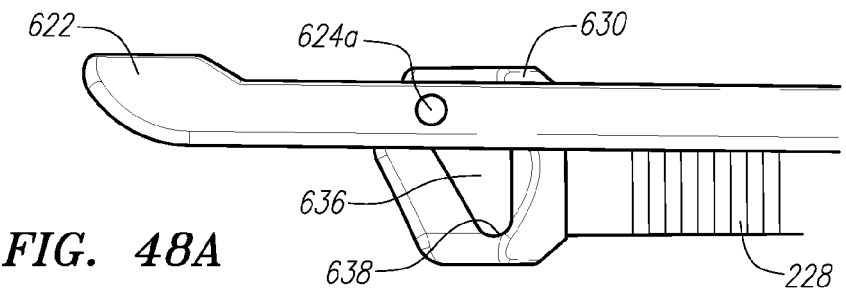
FIGS. 48A-B are side views of the upper fixed bail, launch tube, and pivot of another embodiment of the distal end effector shown in FIGS. 45A-B.
Figure 48B:
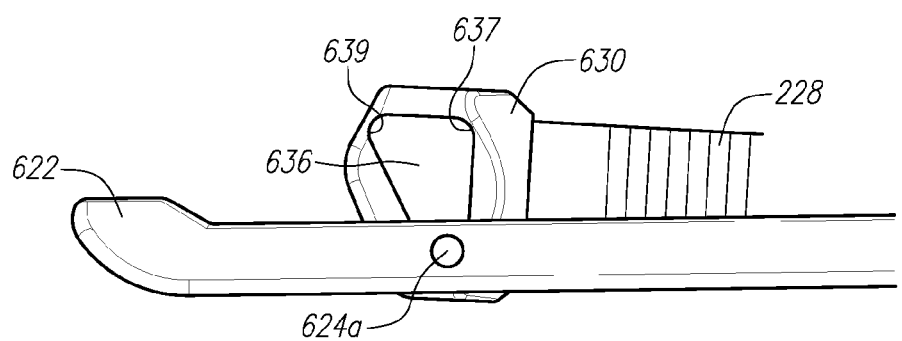

In another embodiment, shown in FIGS. 48A-B, the pivot 630 includes a pivot slot 636 having a generally triangular shape defined by a pivot slot upper corner 637, a pivot slot lower corner 638, and a pivot slot distal corner 639. The generally triangular shape of the pivot slot 636 allows additional ranges of motion enabled by the shape of the pivot slot 636. In addition, the triangular shape of the pivot slot 636 causes the pivot 630 to be biased toward or into the space defined between the lower fixed bail 620 and upper fixed bail 622 (i.e., "downward" relative to the views shown in FIGS. 48-B) when the launch tube 228 is withdrawn proximally (i.e., toward the handle 216) relative to the upper fixed bail 622. This biased motion results from the position of the distal corner 639 that is located distally of the lower corner 638— i.e., as the launch tube 228 moves proximally relative to the upper fixed bail 622, the pivot pins 624a, 624b slide along the internal surface of the slot 636 extending between the lower corner 638 and the distal corner 639 until further movement is prevented.

Returning again to FIGS. 3-7, once the tissue has been engaged between the jaw members 220, 222 (or the fixed bails 620, 622), a needle deployment assembly 260 is urged through the handle 216, though the tubular body 212, and out through the launch tube 228. The needle deployment assembly 260 may pass through the lower jaw member 220 via a needle assembly opening (not shown in the drawing) defined in the lower jaw member 220 to pierce through the grasped tissue. Once the needle deployment assembly has been passed through the engaged tissue, one or more tissue anchors of a tissue anchor assembly 48 (see FIG. 7) are deployed for securing the tissue, as described in further detail herein and in U.S. patent application Ser. No. 10/955,245, which has been incorporated by reference above.

Figure 6:
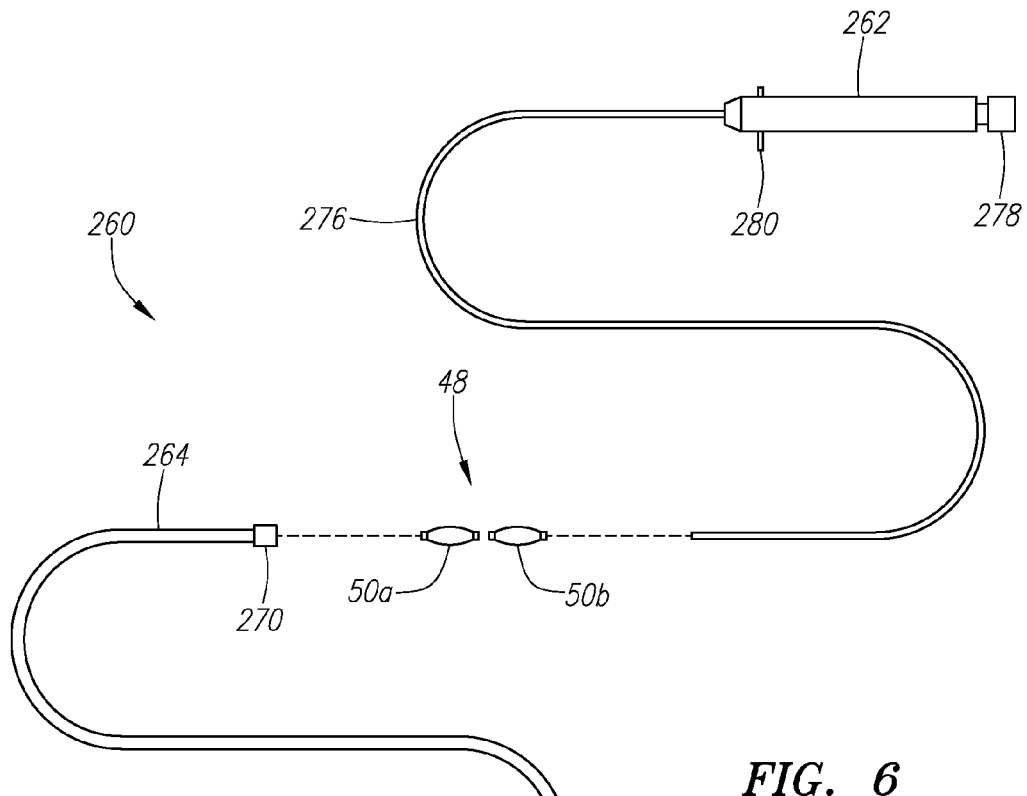
FIG. 6 is an exploded view of the needle deployment assembly of FIG. 3.

FIG. 6 shows additional details relating to the needle deployment assembly 260. As mentioned above, a needle deployment assembly 260 may be deployed through the tissue manipulation assembly 210 by introducing needle deployment assembly 260 into the handle 216 and through the tubular body 212, as shown in the assembly view of FIG. 3, such that the needle assembly 266 is advanced from the launch tube and into or through approximated tissue. Once the needle assembly 266 has been advanced through the tissue, the anchor assembly 48 may be deployed or ejected. The anchor assembly 48 is normally positioned within the distal portion of a tubular sheath 264 that extends from a needle assembly control or housing 262. Once the anchor assembly 48 has been fully deployed from the sheath 264, the spent needle deployment assembly 260 may be removed from the tissue manipulation assembly 210 and another needle deployment assembly may be introduced without having to remove the tissue manipulation assembly 210 from the patient. The length of the sheath 264 is such that it may be passed entirely through the length of the tubular body 212 to enable the deployment of the needle assembly 266 into and/or through the tissue.

The elongate and flexible sheath or catheter 264 extends removably from the needle assembly control or housing 262. The sheath or catheter 264 and the housing 262 may be interconnected via an interlock 270 which may be adapted to allow for the securement as well as the rapid release of the sheath 264 from the housing 262 through any number of fastening methods, e.g., threaded connection, press-fit, releasable pin, etc. The needle body 272, which may be configured into any one of the variations described above, extends from the distal end of the sheath 264 while maintaining communication between the lumen of the sheath 264 and the needle opening 274.

An elongate pusher 276 comprises a flexible wire or hypotube that is translationally disposed within the sheath 264 and movably connected within the housing 262. A proximally-located actuation member 278 is rotatably or otherwise connected to the housing 262 to selectively actuate the translational movement of the elongate pusher 276 relative to the sheath 264 for deploying the anchors from the needle opening 274. The tissue anchor assembly 48 is positioned distally of the elongate pusher 276 within the sheath 264 for deployment from the sheath 264. Needle assembly guides 280 protrude from the housing 262 for guidance through the locking mechanism described above.

Figure 8A:
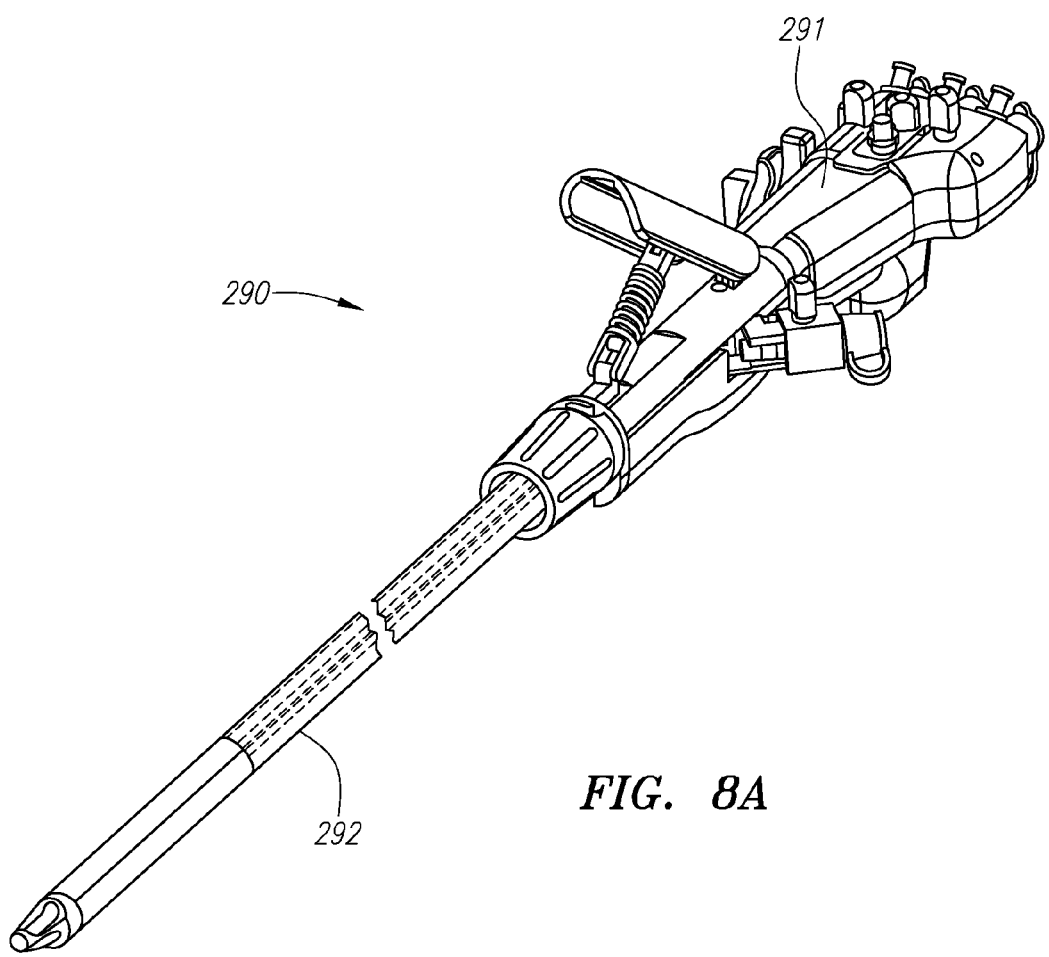
FIGS. 8A and 8B are perspective views of endoscopic access devices.
Figure 8B:
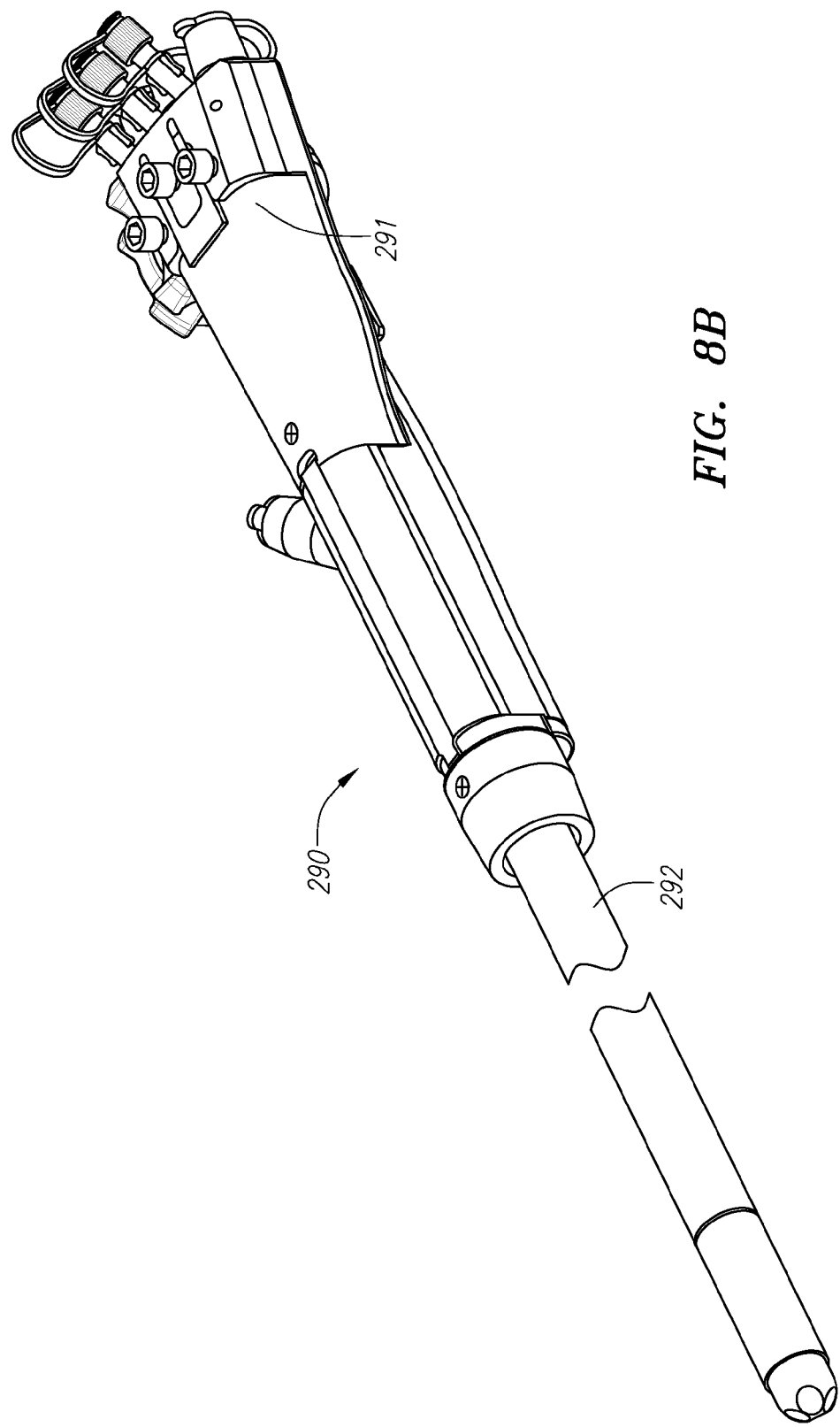

In several embodiments, the delivery device 210 and needle deployment assembly 260 are advanced into the gastrointestinal lumen using an endoscopic or endolumenal access system such as those described in the United States Patent Applications referenced above in Table 1. Examples of endoscopic and endolumenal access systems 290 are shown in FIGS. 8A and 8B. The endoscopic or endolumenal access systems 290 illustrated in FIGS. 8A and 8B each include a control mechanism 291 and a multi-lumen, steerable overtube 292 having several features that are described more fully in U.S. patent application Ser. Nos. 11/750,986 and 12/061, 591, which were incorporated by reference above.

Turning to FIGS. 9-20, an embodiment of an actuator mechanism 70 for a tissue anchor delivery device 208 is shown. The actuator mechanism 70 comprises an alternative embodiment to the handle 216 described above in relation to FIGS. 3 and 4. In the embodiment shown, the actuator mechanism 70 is configured to actuate both the tissue manipulation assembly 210 and the needle deployment assembly 260 independently of one another in order to grasp tissue and deploy a tissue anchor assembly 48 in separate steps.

Figure 9:
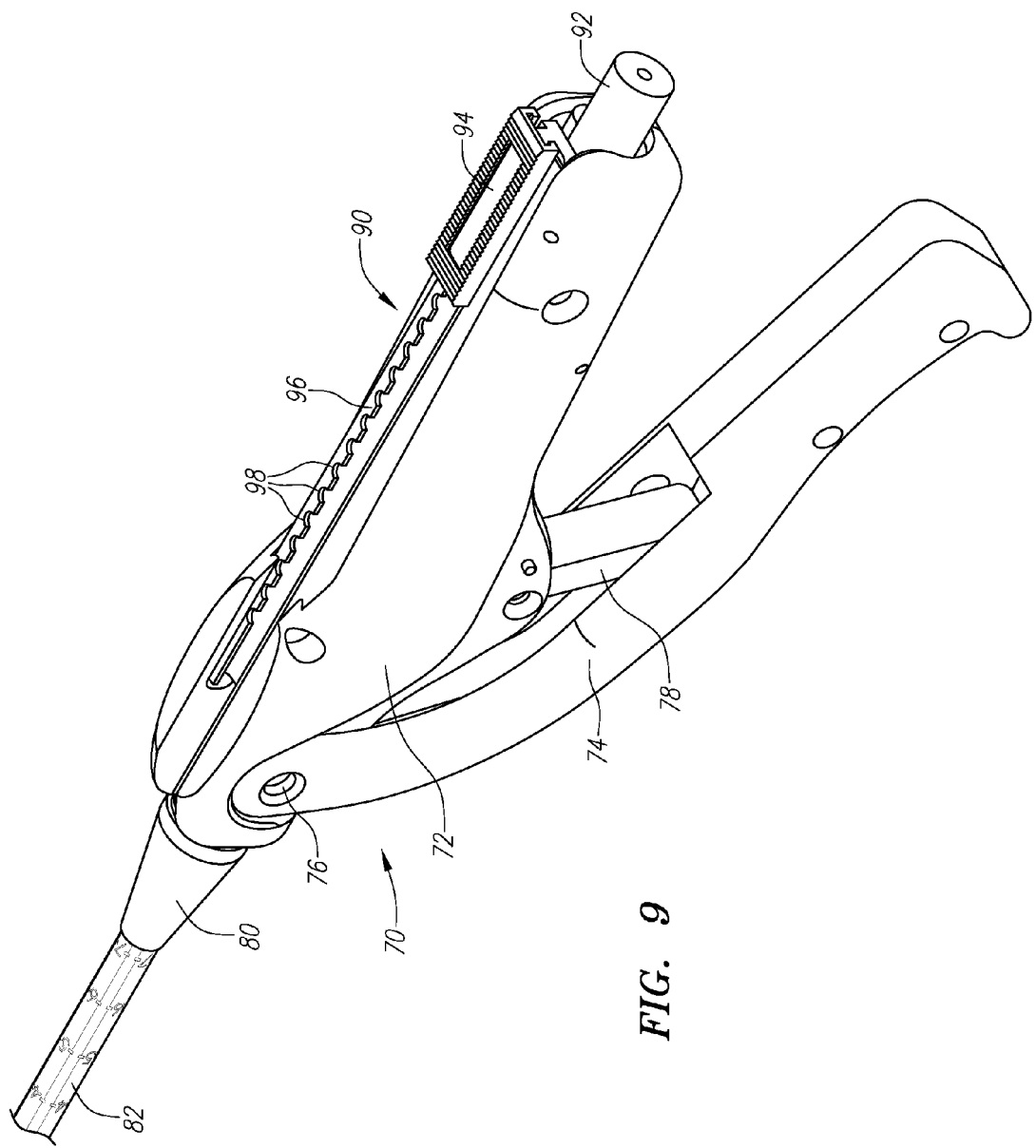
FIG. 9 is a perspective view of an actuator mechanism for a tissue anchor delivery device.

Turning first to FIG. 9, the illustrated actuator mechanism 70 includes a main housing 72 and a handle body 74 that is pivotably attached to the main housing by a hinge pin 76, such that a user is able to grasp the main housing 72 and handle body 74 in one hand and actuate the mechanism by pulling the handle body 74 toward the main housing 72. A linkage arm 78 is interposed between the main housing 72 and the handle body 74, as discussed in more detail below. A nose cone 80 is attached to the distal end of the main housing 72 and surrounds the proximal end 82 of the tubular body 212.

In the embodiment shown, the proximal end 82 of the tubular body 212 is formed of a rigid material such as a rigid polymer material or stainless steel tubing. The remainder of the tubular body 212 is flexible and is formed of materials used to form the insertion portion of endoscopes and endoscopic devices. In alternative embodiments, the tubular body portion is formed of a composite tube that includes one or more polymeric materials (e.g., Pebax) and one or more braided layers (e.g., stainless steel or polymeric braid) to provide the tubular body 212 with improved torque transmission and resistance to stretching.

A needle deployment assembly actuation mechanism 90 includes a needle launch bushing 92, a needle launch button 94, and a needle launch track 96. The needle launch track 96 includes a plurality of substantially equally spaced, scallop-shaped cutouts 98 formed along the length of the track 96. More details of the structure and function of the needle deployment assembly actuation mechanism 90 is provided below.

Figure 10:
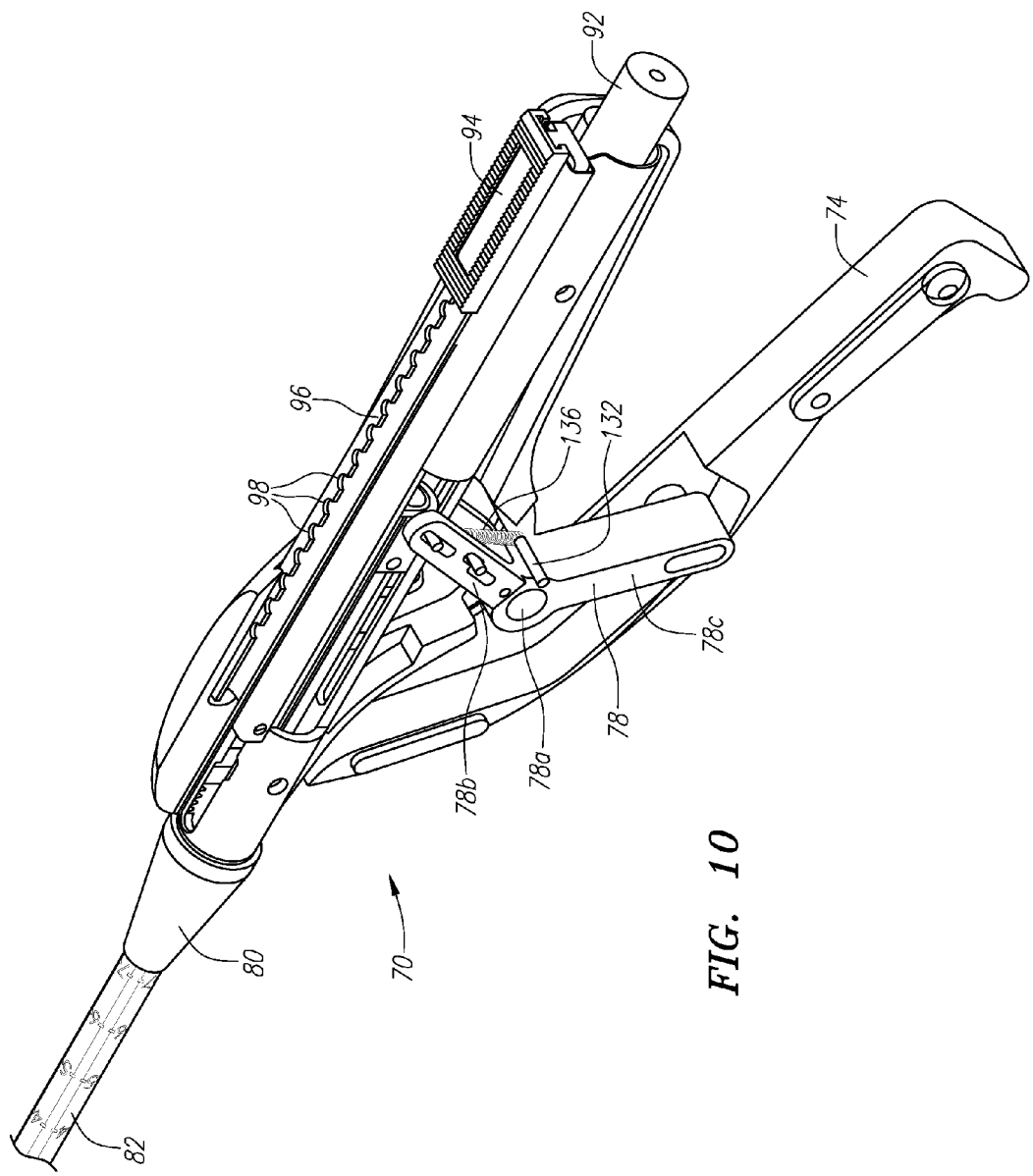
FIG. 10 is a perspective view of the actuator mechanism of FIG. 9 with portions of the handle body and main housing removed for clarification.
Figure 11:
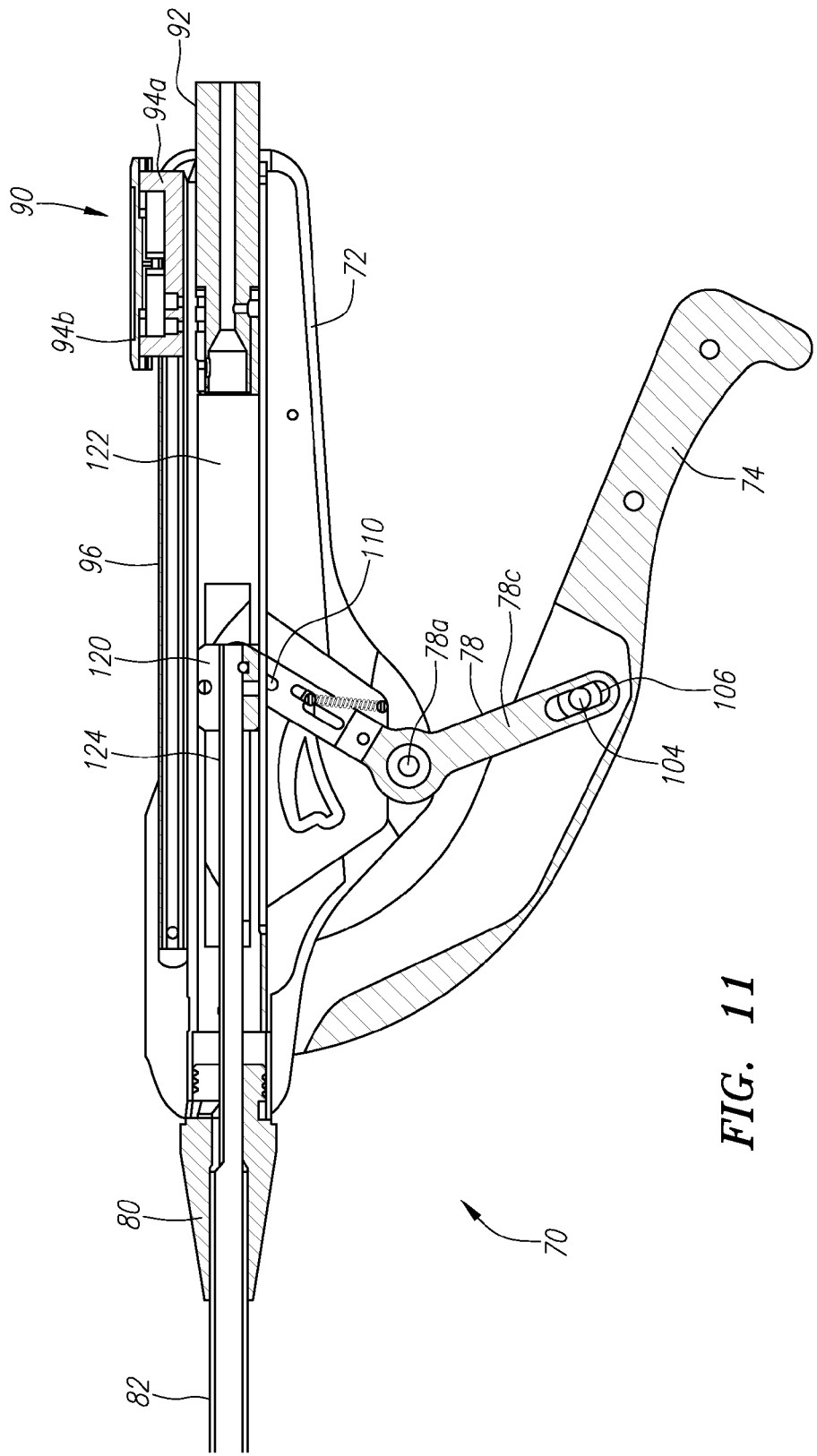
FIG. 11 is a cross-sectional view of the actuator mechanism of FIG. 9.

FIGS. 10 and 11 show additional details concerning the structure and operation of the actuator mechanism 70. The linkage arm 78 is pivotably mounted to the main housing 72 by a linkage arm pivot pin 102, about which the linkage arm 78 is able to rotate. The linkage arm 78 includes a hub portion 78a, a drive arm 78b extending from the hub 78a substantially toward the central portion of the main housing 72, and a handle arm 78c extending from the hub 78a substantially toward the handle body 74. In the embodiment shown, the drive arm 78b and the handle arm 78c connecting through the hub portion 78a define an acute included angle, i.e., a "V"-shape. A handle body pin 104 is mounted on and extends from the handle body 74 through a handle arm slot 106 formed on the handle arm 78c. A drive bushing pin 108 is mounted on a drive bushing 120 and extends from the drive bushing 120 through a drive arm slot 110 formed on the drive arm 78b.

The drive bushing 120 resides in a drive channel 122 formed in the main housing 72. More particularly, the external size and shape of the drive bushing 120 closely matches the internal size and shape of the drive channel 122 such that the drive bushing 120 is able to slide through the drive channel 122 along the longitudinal axis of the main housing 72. The drive bushing 120 is attached to (or formed integrally with) the proximal end of the launch tube 228, which extends through the drive channel 122 and the tubular body 212 to the end effector 214, as described above in relation to FIGS. 4 and 5A-B. In the embodiment shown, the drive bushing 120 and the proximal portion of the launch tube 228 (e.g., the portion of the launch tube extending through the drive channel 122 in the main housing 72) each includes an upward-facing opening defining a loading channel 124 for receiving and retaining a needle deployment catheter, as described more fully below.

During operation, as the handle body 74 is moved toward the main housing 72 (by rotating the handle body 74 around the hinge pin 76), the handle body pin 104 causes the linkage arm 78 to rotate counterclockwise (as viewed in FIG. 11), thereby driving the drive bushing 120 toward the distal end of the device (i.e., toward the left as viewed in FIG. 11). This action causes the launch tube 228 to translate distally, e.g., from the jaws open position illustrated in FIG. 5B to the jaws closed and launch tube pivoted position illustrated in FIG. 5A. In this way, the action of squeezing the handle body 74 toward the main housing 72 causes the actuation mechanism 70 to actuate the launch tube 228 which action causes the lower jaw 220 and upper jaw 222 of the end effector 214 to grasp and manipulate tissue. The squeezing action also causes the portion of the launch tube 228 that extends distally from the tubular body 212 to rotate at the hinge or pivot 230 and reconfigure itself such that the exposed portion forms a curved or arcuate shape that positions the launch tube opening substantially perpendicularly relative to the upper jaw member 222. (See, e.g., FIG. 5A). This position facilitates delivery of the anchor assembly 48, as described above and below.

The actuation mechanism 70 embodiment shown in the drawings also includes a handle lock mechanism 130 that is configured to maintain the position of the handle body 74 relative to the main housing 72 at one or more positions during operation of the actuation mechanism 70. The handle lock mechanism 130 is illustrated in FIGS. 12A-G, which represent several positions of the handle lock mechanism that occur during a single cycle of the actuation mechanism 70. The handle lock mechanism 130 includes a stationary pin 132 that is fixed to (or formed integrally with) the main housing 72, and a locking pin 134 that is neither fixed to nor formed integrally with the main housing 72. A locking pin spring 136 is connected at one end to the stationary pin 132 and at its other end to the locking pin 134, thereby providing a force biasing the locking pin 134 toward the location of the stationary pin 132. The locking pin 134 extends through a locking pin slot 112 formed through the drive arm 78b between the hub 78a and the drive arm slot 110. The locking pin slot 112 includes and outer portion 112a and an inner portion 112b, with a ledge 112c located at the transition between the outer portion 112a and the inner portion 112b.

In the embodiment shown, the handle lock mechanism 130 also includes a locking pin track 138. The locking pin track 138 comprises a set of grooves and raised surfaces formed on at least one of the inner facing surfaces of the main housing 72. The locking pin 134 extends into one or more of the grooves defined by the locking pin track 138 such that the track 138 limits the movement of the locking pin 134. In the illustrated embodiment, the track 138 includes an upper groove 140, a distal groove 142, and a lower groove 144. Together, the upper groove 140, distal groove 142, and lower groove 144 form a substantially triangular shape in which each of the grooves is connected at a point to each of the other grooves. As described below, translation of the locking pin 134 along and through the upper groove 140 corresponds with movement of the handle body 74 toward the main housing 72 and, concurrently, movement of the launch tube 228 distally toward the end effector 214. Positioning the locking pin 134 within the distal groove 142 corresponds with the jaws closed and launch tube pivoted and curved position illustrated in FIG. 5A. Finally, translation of the locking pin 134 along and through the lower groove 144 corresponds with movement of the handle body 74 away from the main housing 72 and, concurrently, movement of the launch tube 228 proximally.

Figure 12A:
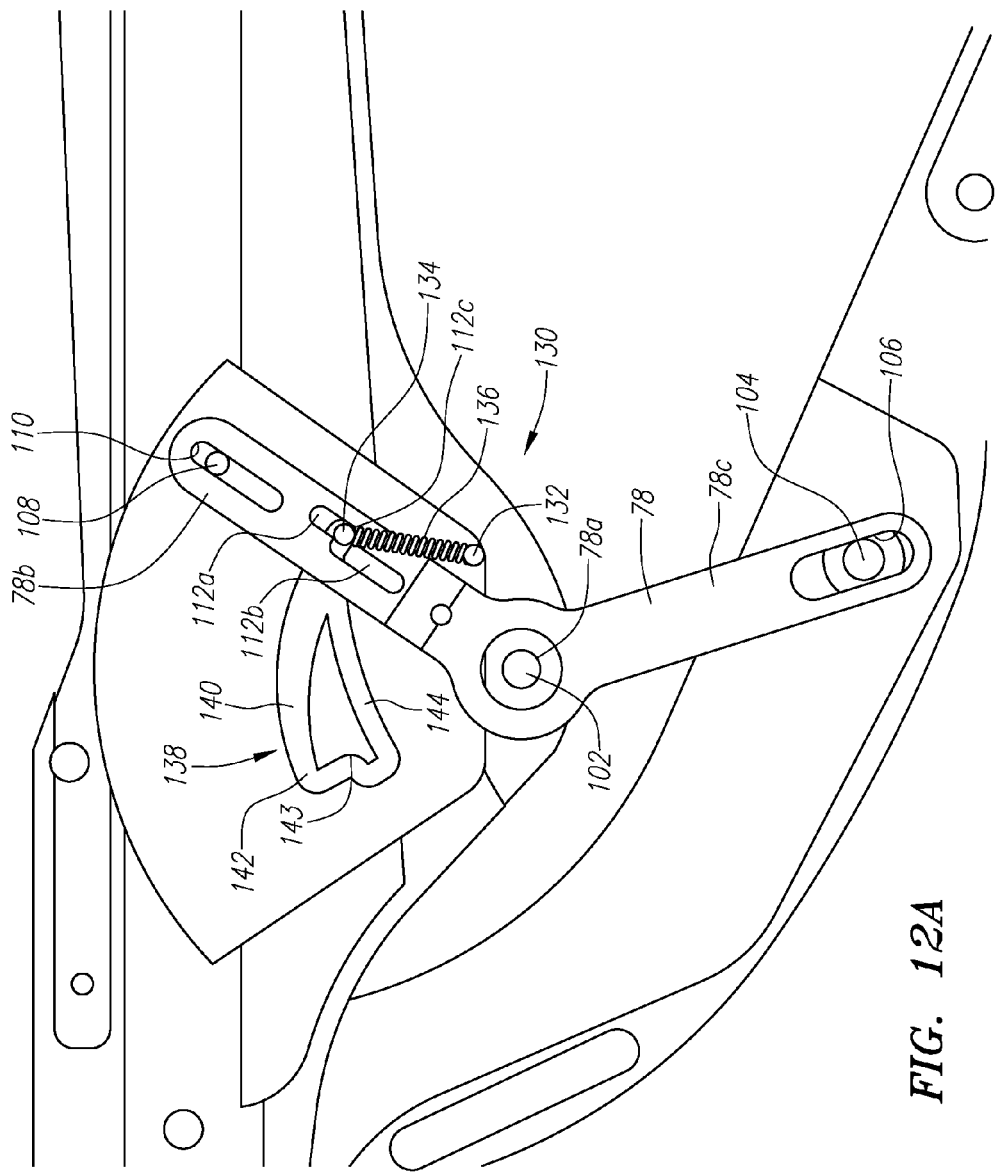
FIGS. 12A-G are side views of an embodiment of a handle lock mechanism of the actuator mechanism of FIG. 9.
Figure 12B:
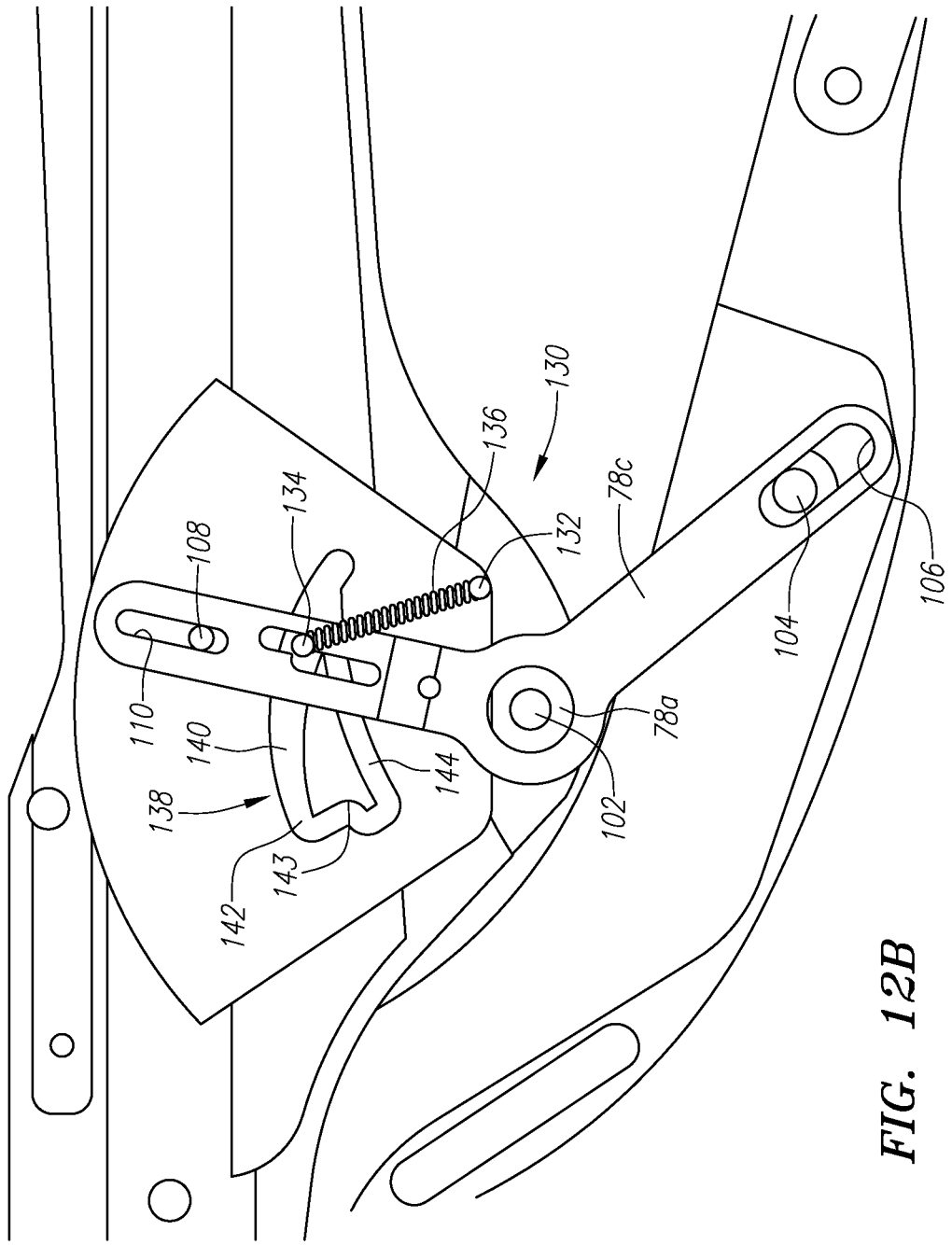
Figure 12C:
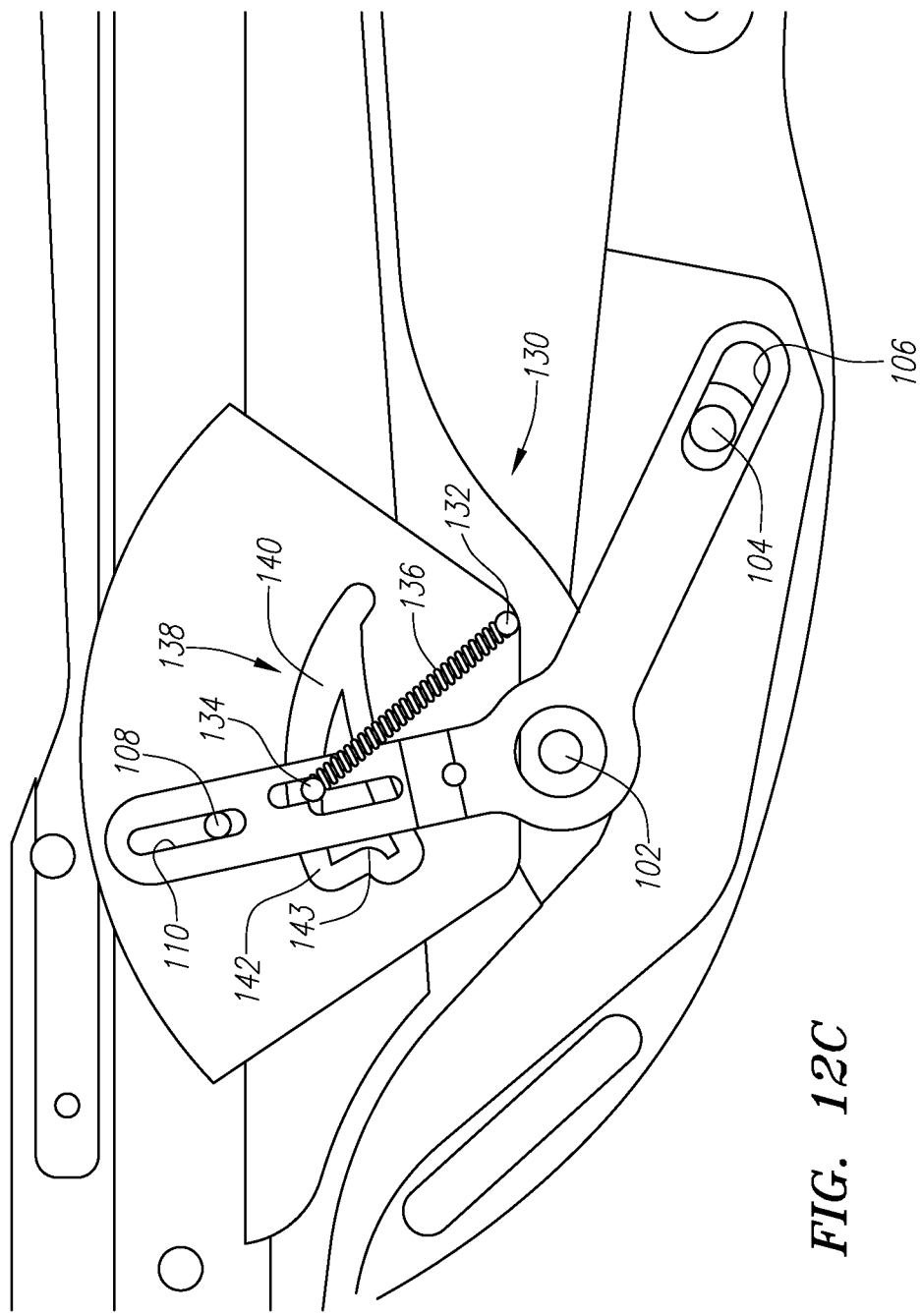
Figure 12D:
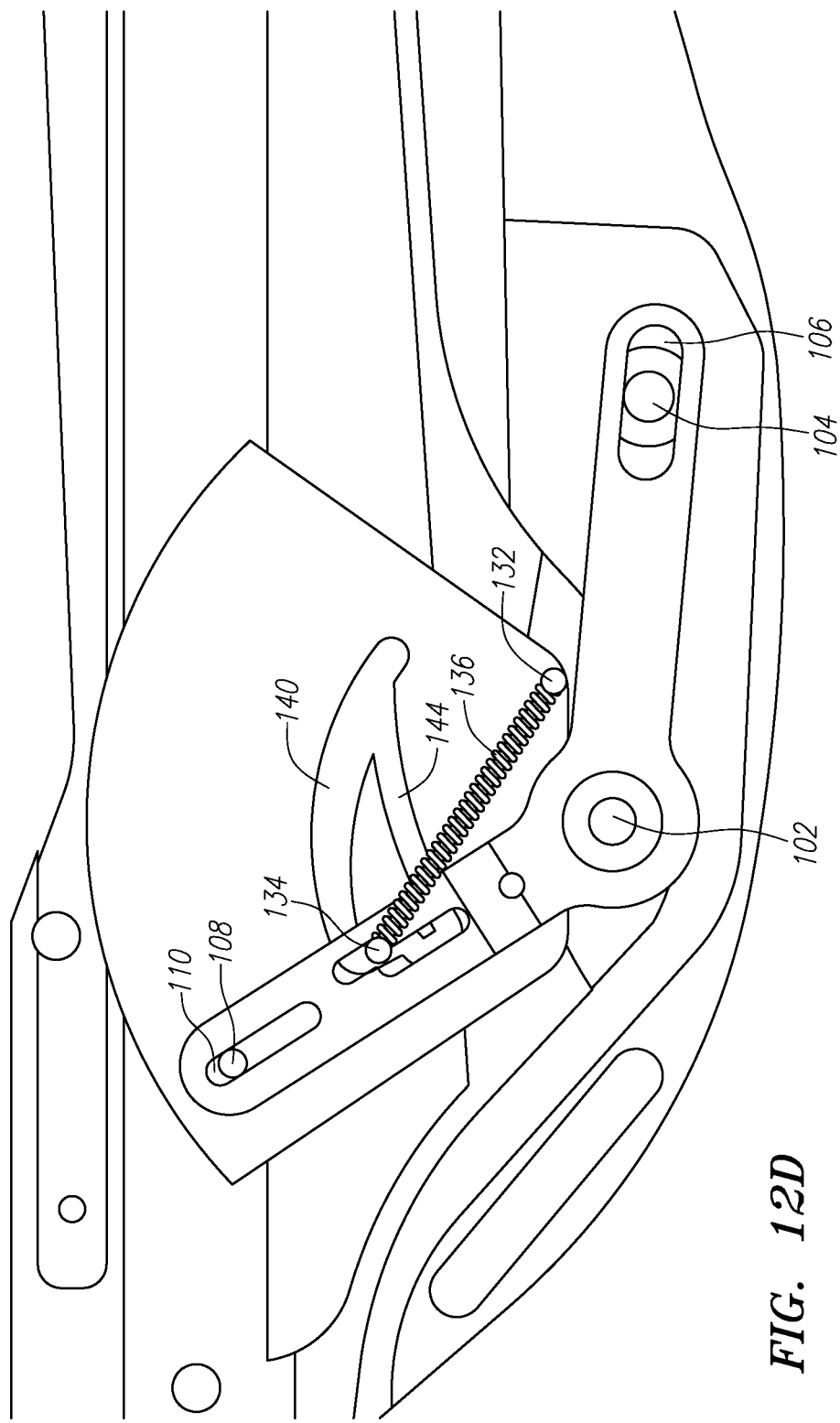
Figure 12E:
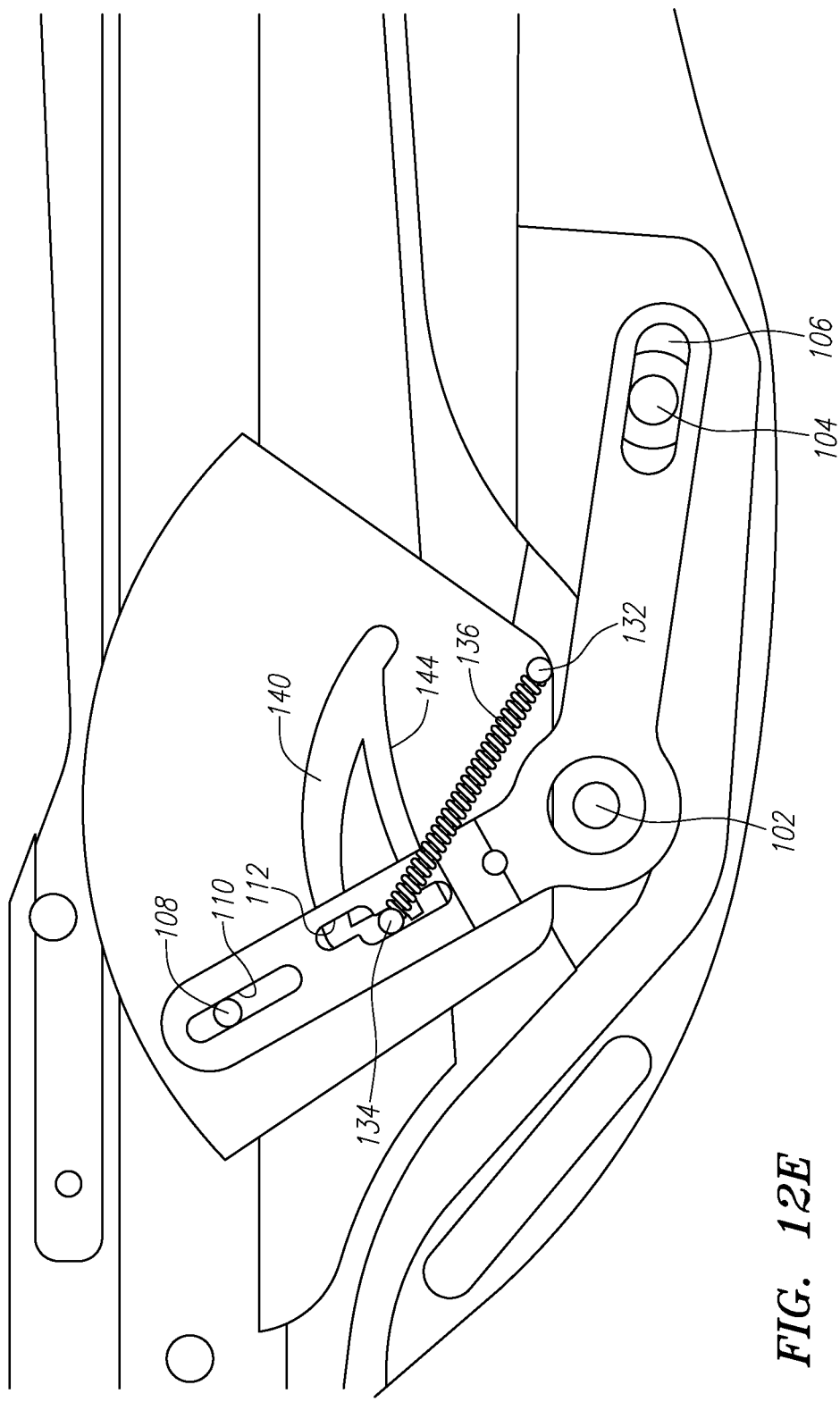

FIG. 12A shows a starting position of the locking mechanism 130 in which the drive arm 78b is at its proximal-most position. The locking pin 134 is positioned within the outer portion 112a of the locking pin slot and is at the intersection of the upper groove 140 and lower groove 144. As the handle body 74 and main housing 72 are squeezed together, the linkage arm 78 rotates counterclockwise (as shown in FIGS. 12A-G). This motion causes the drive arm 78b to move the locking pin 134 generally distally. The locking pin spring 136 provides a generally downward and proximal force (as shown in FIGS. 12A-G) on the locking pin 134, causing the locking pin 134 to rest upon the ledge 112c of the locking pin slot. The radial position of the ledge 112c on the drive arm 78b causes the locking pin 134 to translate through the upper groove 140, rather than the lower groove 144, as the locking pin 134 traverses the intersection of the two grooves (see FIG. 12B) and beyond (see FIG. 12C).

As the locking pin 134 traverses the upper groove 140, the ramped surface of the upper groove biases the locking pin 134 radially outward in the outer portion 112a of the locking pin slot, i.e., away from the ledge 112c. Further squeezing of the handle body 74 and main housing 72 causes the locking pin 134 ultimately to reach the distal slot 142, upon which the force of the locking pin spring 136 causes the locking pin 134 to slide into the distal slot 142 until the locking pin 134 again encounters the ledge 112c of the locking pin slot. (See FIG. 12D). At this point, the locking pin 134 is trapped between the edges of the locking pin slot 112 of the linkage arm 78 and the distal slot 142 of the locking pin track 138, preventing any further rotation of the handle body 74 relative to the main housing 72. As the user releases the squeezing action on the handle body 74, the linkage arm 78 will rotate slightly in the clockwise direction (as shown in FIGS. 12A-G), releasing the locking pin 134 from the ledge 112c of the locking pin slot and into a trough 143 formed in the distal groove, where it is retained under the force of the locking pin spring 136. (See FIG. 12E). Upon re-squeezing by the user of the handle body 74 relative to the main housing 72, the edge of the inner portion 112b of the locking pin slot engages the locking pin 134, forcing the locking pin 134 out of the trough 143 of the distal groove. The spring force of the locking pin spring 136 pulls the locking pin 134 downward from the distal groove 142 into the intersection of the distal groove 142 with the lower groove 144. (See FIG. 12F). As the handle body 74 is released by the user, the linkage arm 78 rotates clockwise (as shown in FIGS. 12A-G) and the locking pin 134 is allowed to traverse the lower groove 144 proximally (see FIG. 12G) until the locking pin 134 returns to the staring position.

Those skilled in the art will recognize that the handle lock mechanism 130 embodiment described herein may be modified to provide a range of movement different from that provided by the embodiment shown in order to support other and different functions or processes to be performed by the device associated with the actuator mechanism 70. For example, a single cycle may include more or fewer grooves and intersections. Variations of other parameters and components are also possible.

Figure 12F:
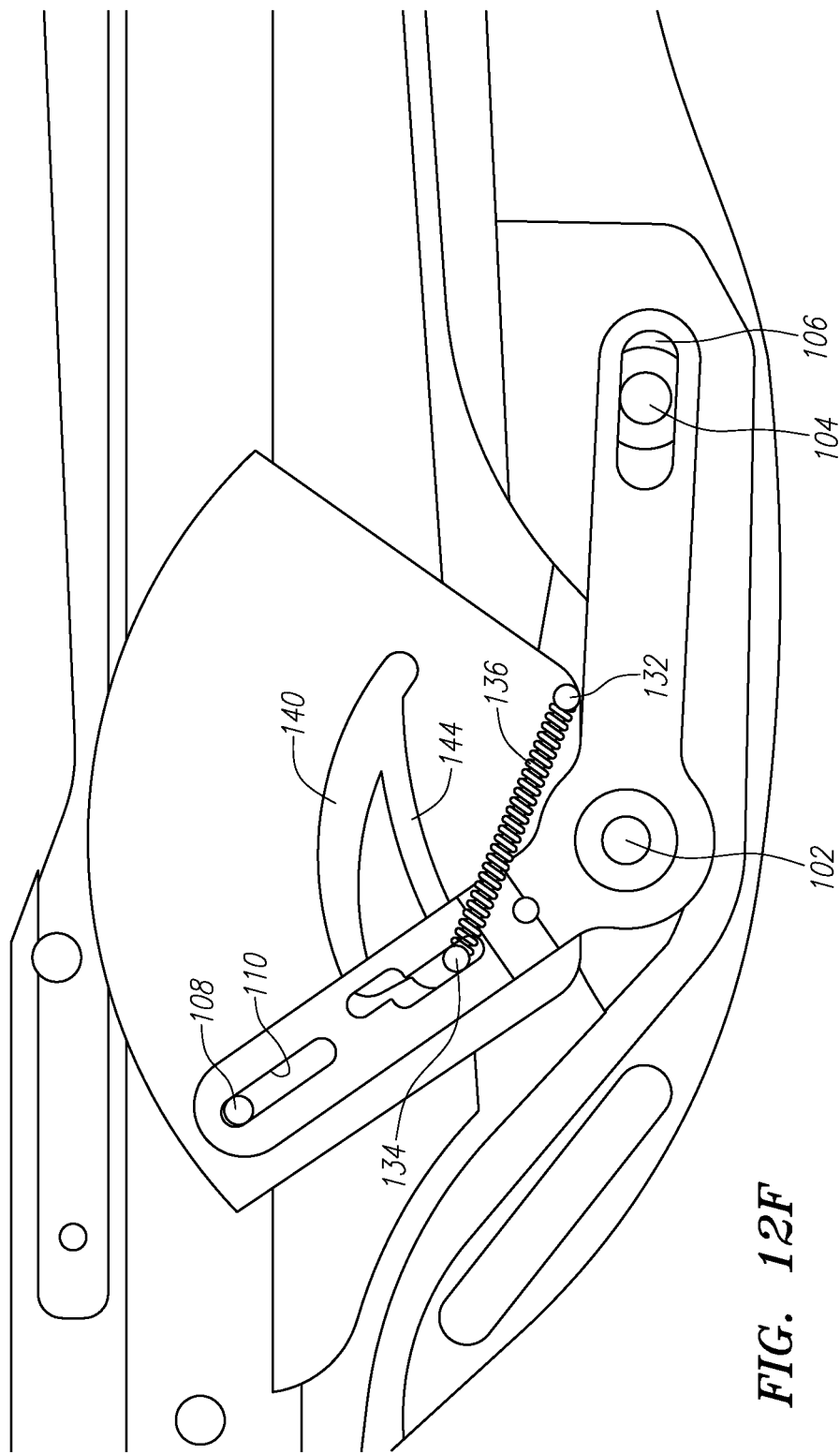
Figure 12G:
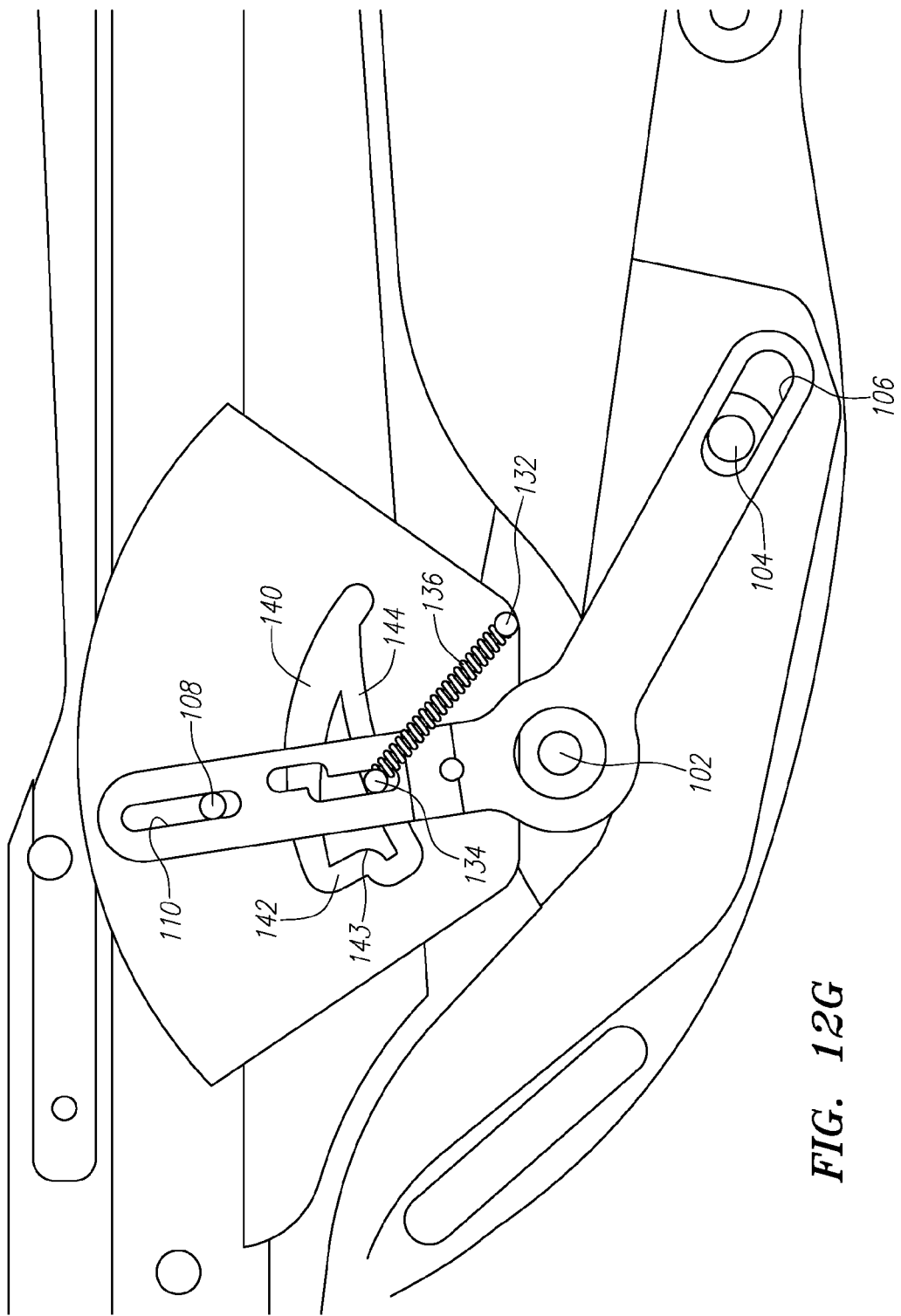
Figure 13A:
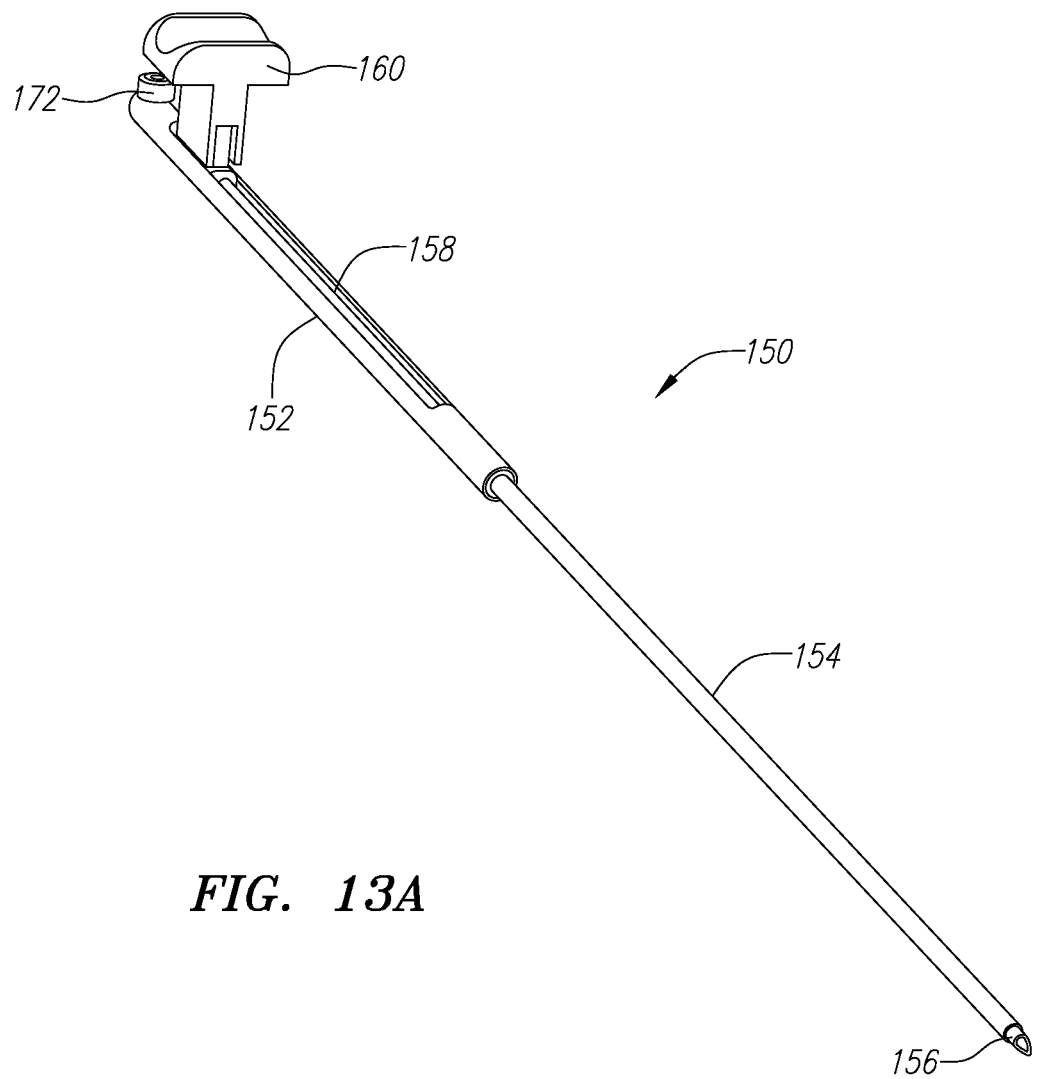
FIGS. 13A-B are perspective views of another embodiment of a needle deployment assembly.
Figure 13B:
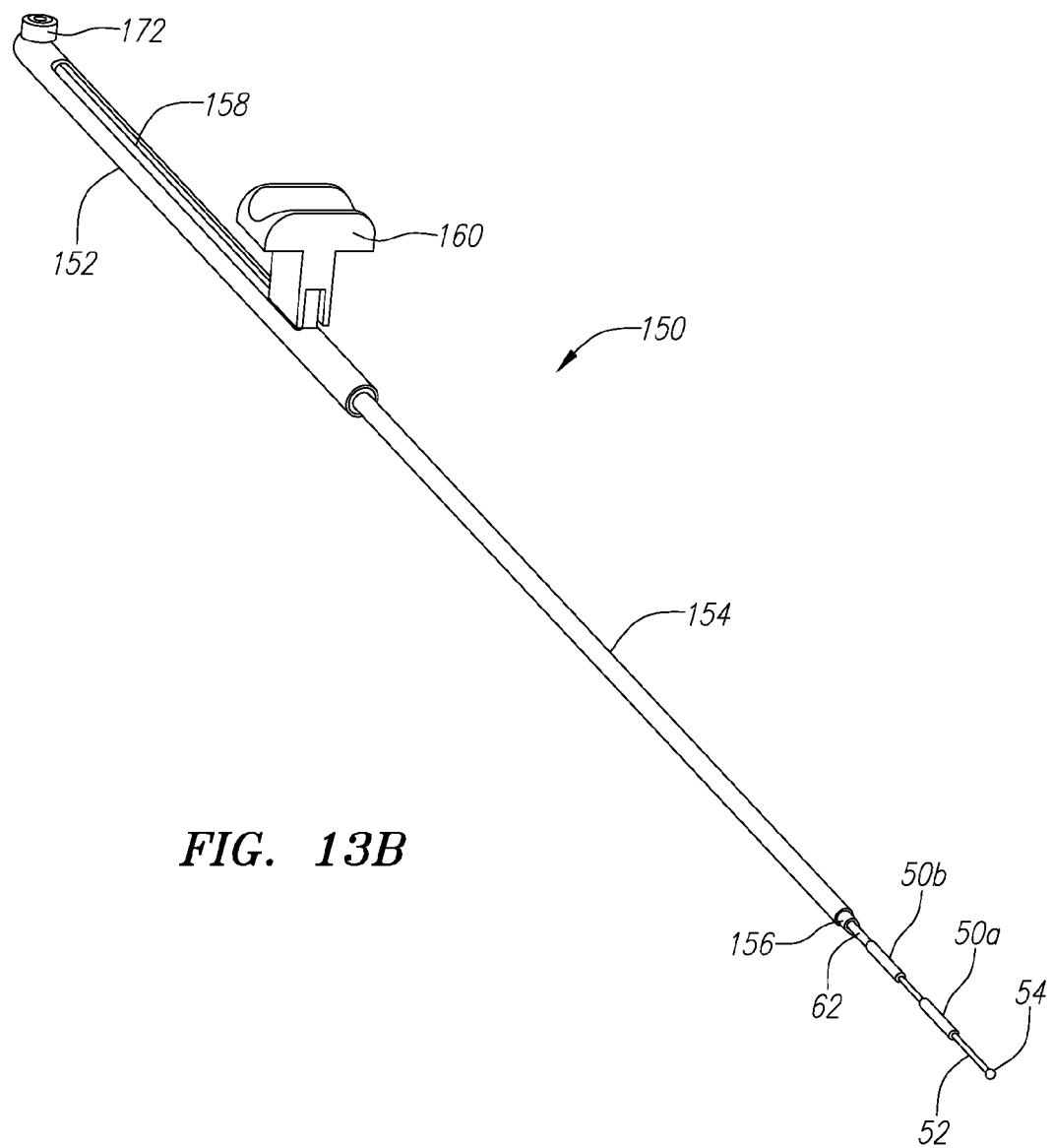

Turning next to FIGS. 13A and 13B, another embodiment of a needle deployment assembly 150 is shown. The needle deployment assembly 150 is configured for use with the actuator mechanism 70 described above in relation to FIGS. 9 through 12. The assembly 150 includes a rigid body portion 152 and a flexible catheter portion 154 extending distally from the distal end of the rigid body portion 152. A needle 156 is fixed to the distal end of the catheter portion 154. The upper surface of the rigid body portion 152 includes an elongated groove 158 that provides access into the generally tubular rigid body 152. A suture deployment button 160 extends from the interior of the rigid body portion 152 through the groove 158.

Figure 14A:
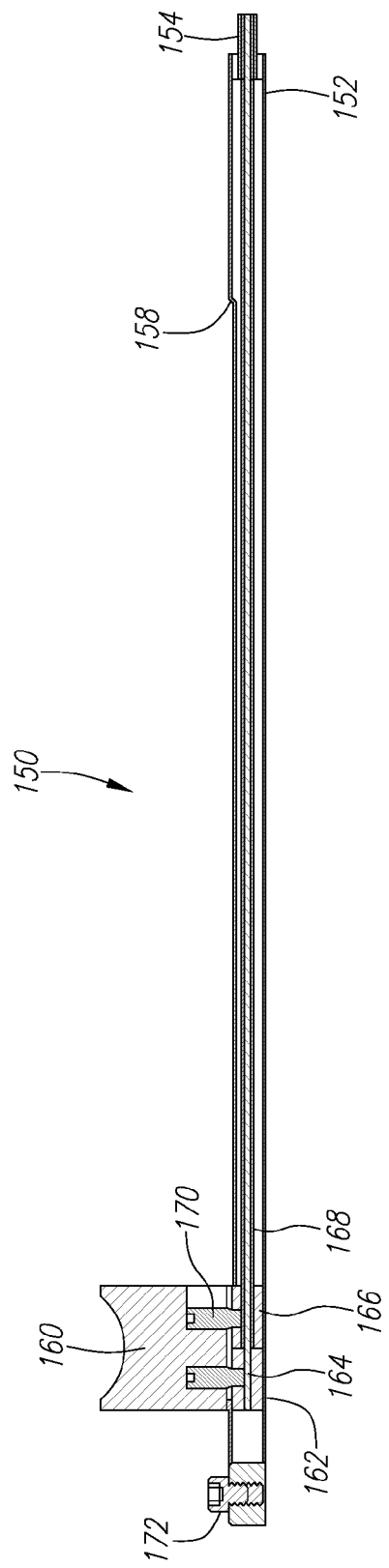
FIGS. 14A-C are cross-sectional views of a rigid body portion of the needle deployment assembly of FIGS. 13A-B.
Figure 14B:
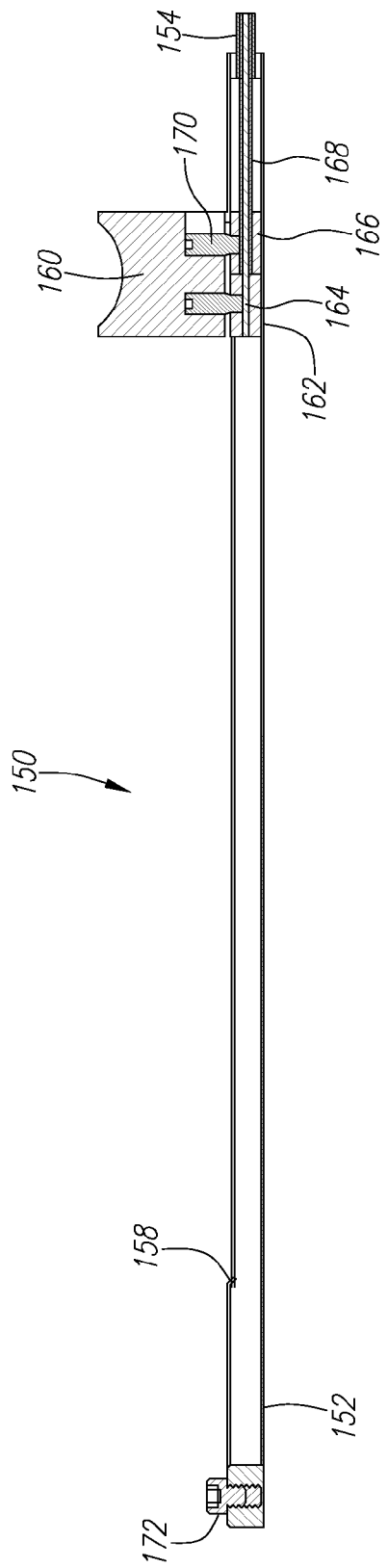
Figure 14C:
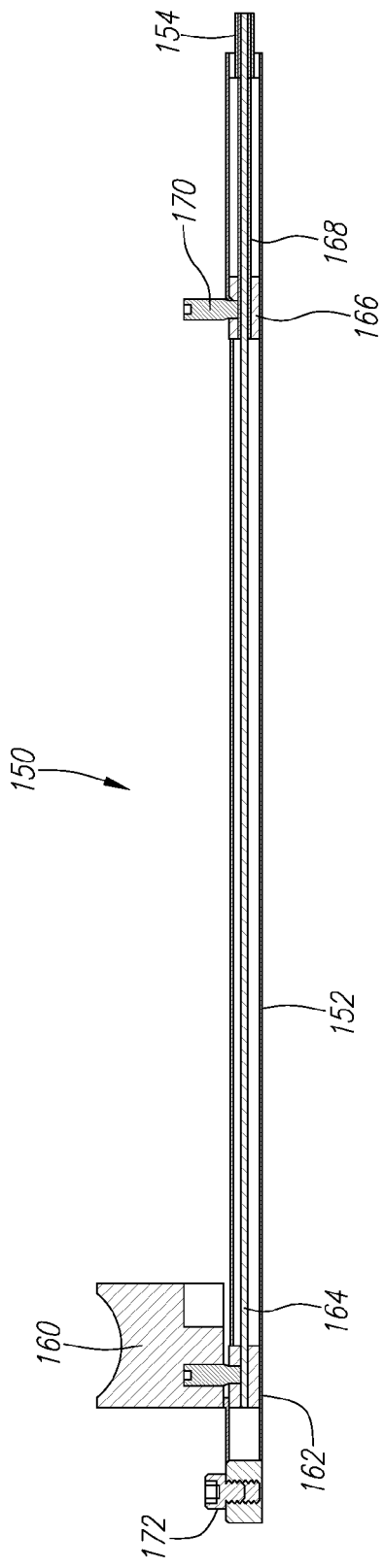

Additional details of the needle deployment assembly are shown in the cross-sectional views provided in FIGS. 14A-C. As shown there, the suture deployment button 160 is attached via a screw to a suture wire bushing 162 that is concentrically and slidably retained within the rigid body portion 152 of the assembly. The suture wire bushing 162 is attached to a suture wire 164 (e.g., nitinol, stainless steel, cable, or braid) that extends through the rigid body 152 and the flexible catheter 154. A pusher coil bushing 166 is also concentrically and slidably retained within the rigid body portion 152 just distally of and, at the position shown in FIG. 14A, abutting the suture wire bushing 162. The pusher coil bushing 166 is attached to a pusher coil 168 that extends through the rigid body 152 and the flexible catheter 154. In the embodiment shown, the pusher coil 166 is a coiled wire defining a central lumen through which the suture wire 164 extends substantially concentrically. A pusher coil bushing set screw 170 is attached to the pusher coil bushing 166 and extends upward through the groove 158 into a recess formed in the suture deployment button 160. An attachment post 172 is formed on the proximal end of the rigid body 152.

Figure 15A:
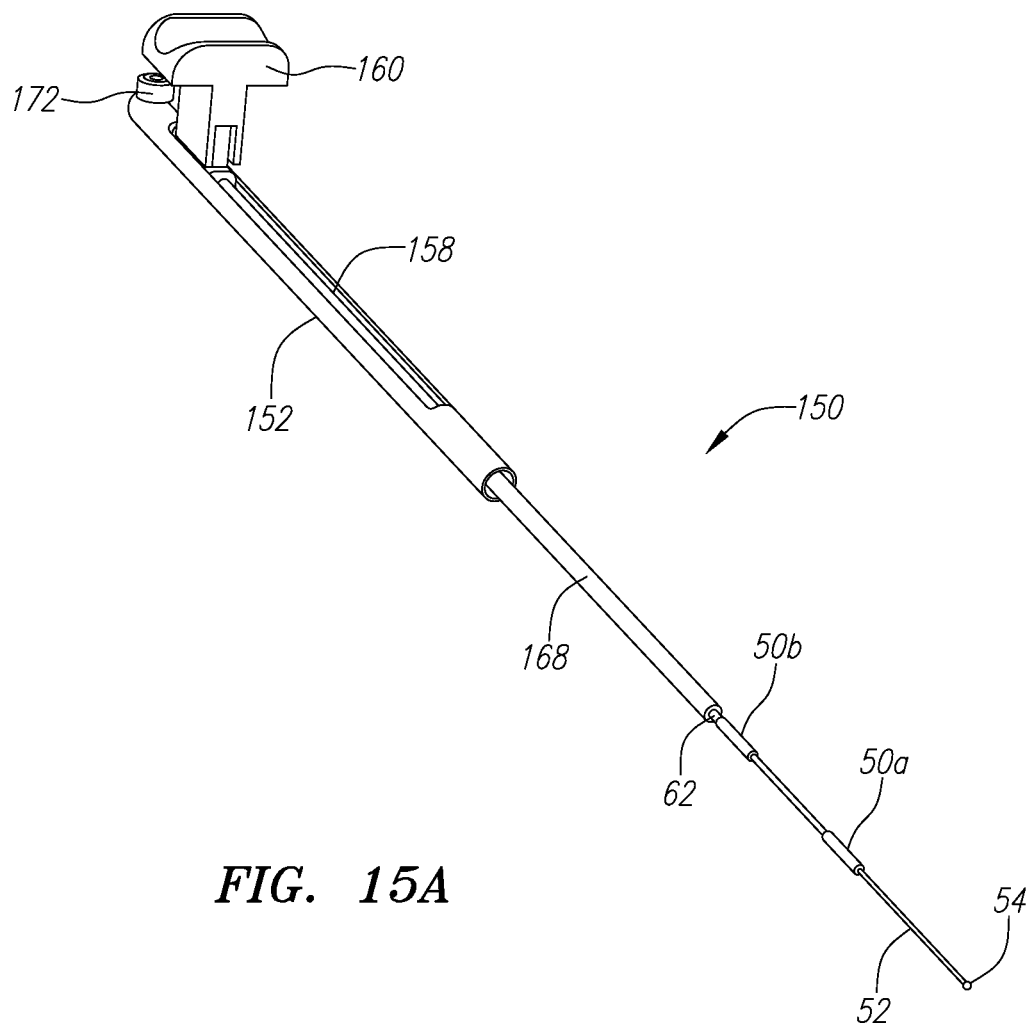
Figure 15B:
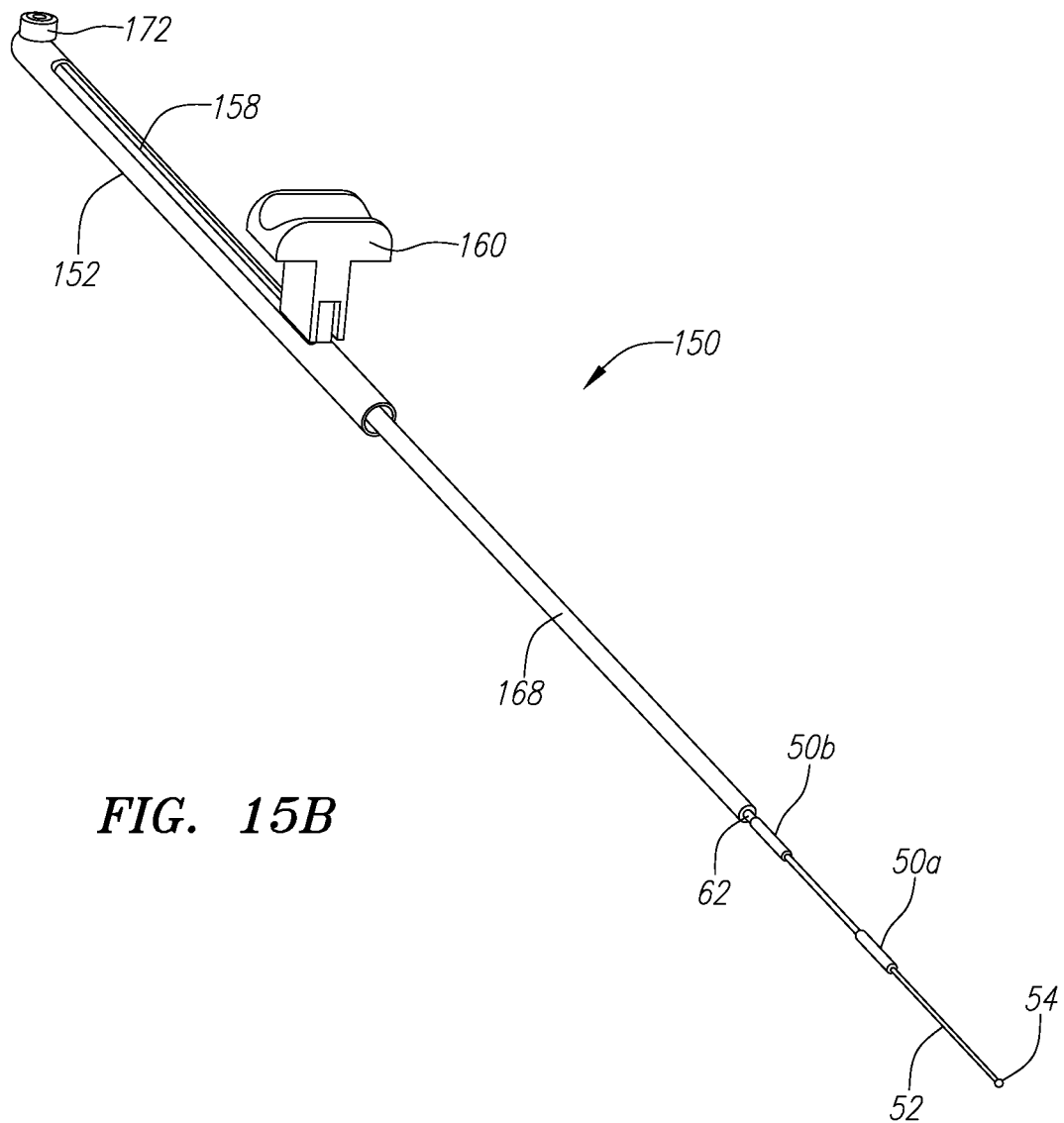

Turning next to FIGS. 15A-C, the structure of the anchor assembly 48 is shown. The anchor assembly 48 includes a distal anchor 50a, a proximal anchor 50b, a suture 52, and a cinch 62. A knot 54 is formed at the distal end of the suture 52. A proximal end of the suture 52 is attached to a distal end of the suture wire 164 in a manner described below.

The operation of the needle deployment assembly 150 will now be described. A starting point is shown in FIGS. 13A, 14A, and 15A, in which the suture deployment button is at its proximal-most extent. As the suture deployment button 160 is advanced distally, the suture wire bushing 162 and pusher coil bushing 166 are advanced distally, thereby driving the anchor assembly 48 distally until the anchor assembly 48 exits the catheter body 152 through the needle 156. (See FIGS. 13B, 14B, 15B). In an embodiment, the distal anchor 50a and proximal anchor 50b are advanced in separate steps, as described more fully below. After full advancement, the pusher coil bushing set screw 170 may be locked in place by moving the screw 170 into a detent (not shown) located at a distal end of the groove 158, thereby fixing the pusher coil 168 in place relative to the other components of the assembly. In one embodiment, the detent comprises a narrowed region of the groove 158 that provides a snug press-fit for the screw 170. Other detent mechanisms are also possible. Next, the suture deployment button 160 is retracted proximally, whereby the suture wire 164 is retracted as the pusher coil 168 is fully extended. The distal end of the pusher coil 168 has a diameter that substantially matches up with the diameter of the cinch 62, whereby the pusher coil 168 prevents proximal movement of the cinch 62 and any of the components retained on the suture 52 on the distal side of the cinch 62. As the knot 64 engages the distal portion of the distal anchor 50a, further retraction of the button 160 causes the anchors 50a, 50b to transition to their expanded deployment state. (See FIGS. 14C, 15C, and 16A-B).

Figure 16A:
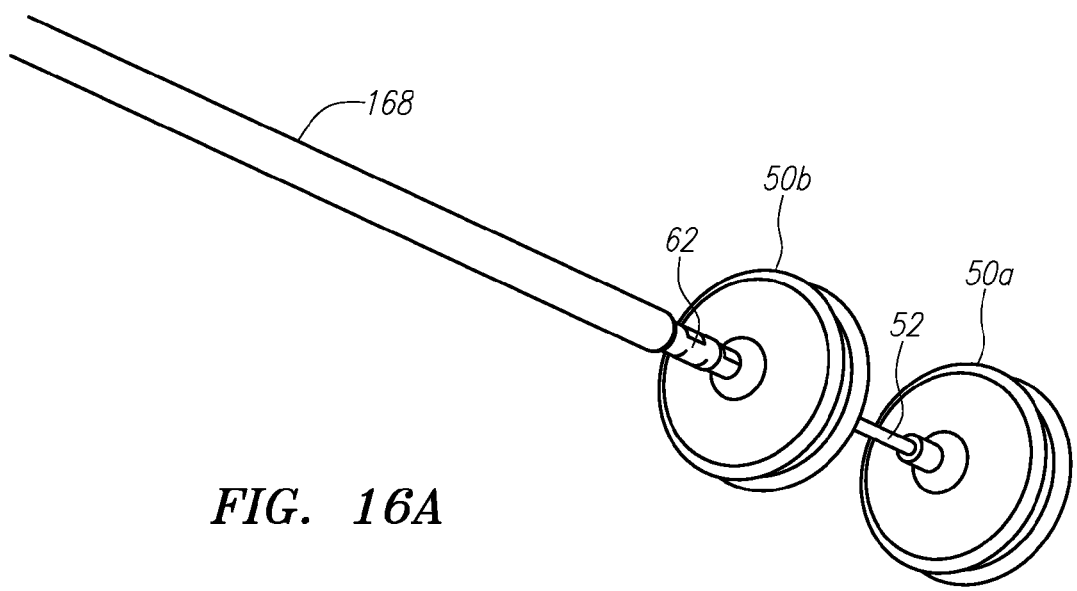
FIGS. 16A-B are perspective and cross-sectional views, respectively, of an anchor assembly in an expanded or deployed state.
Figure 16B:
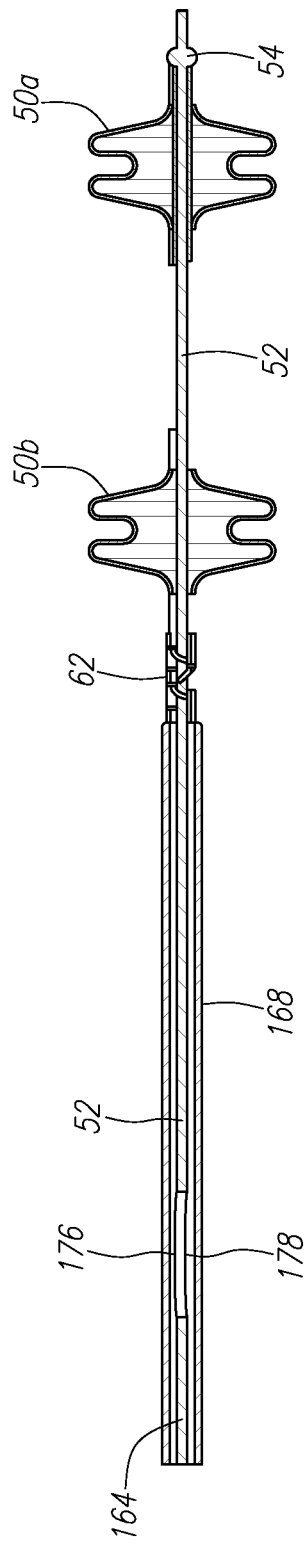
Figure 17:
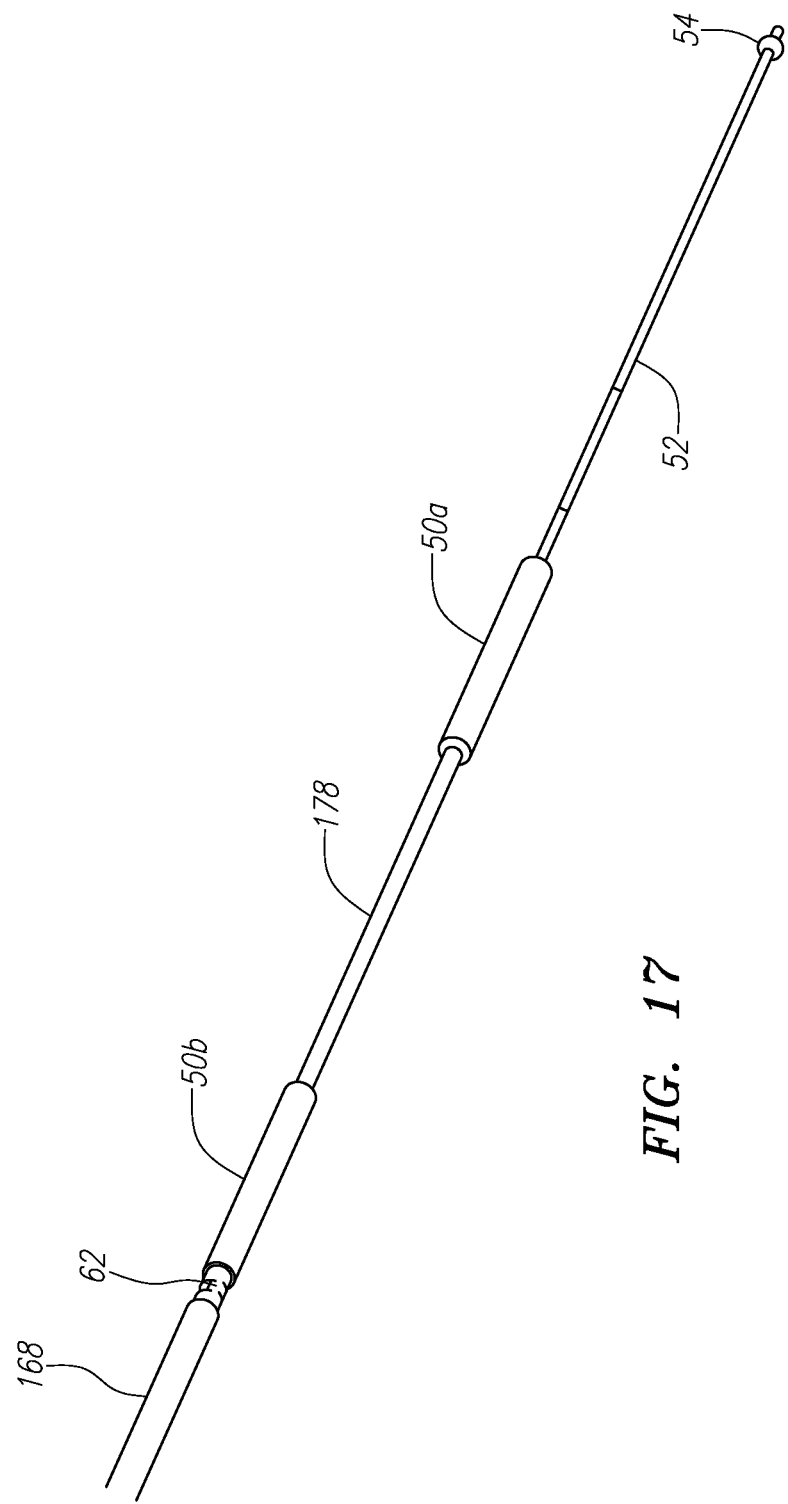
FIG. 17 is a perspective view of an anchor assembly in an unexpanded or delivery state.

In the embodiment shown, the anchor assembly 48 includes a breakaway feature that facilitates separation of the anchor assembly 48 from the suture wire 164, thereby providing the ability to deposit the anchor assembly 48 and separate it from the delivery device without the need to cut the suture 52. As shown in FIG. 16B, a junction 176 is formed between the suture wire 164 and the suture 52. In the embodiment, one or more layers of shrink wrap 178 are applied over the junction and affixed to both the suture wire 164 and the suture 52, thereby bonding the two together. The shrink wrap 178 creates a slight "bump," or an in the thicknesses of the suture 52 and the suture wire 164 where it is applied over the suture 52 and suture wire 164. In the embodiment shown, the increased thickness provided by the "bump" causes an increase in the pushing force needed to cause an anchor 50a, 50b or a cinch 62 to pass over the junction 176, but it does not prevent passage of these components. Moreover, the shrink wrap 178 has sufficient tensile strength to support the cinching procedure described above, while still providing the ability to pull the junction apart upon applying a relatively small tensile load on the suture wire 168.

As a result, in operation, the added thickness provided by the layer of shrink wrap 178 causes the distal anchor 50a to remain stationary on the suture 52 while the anchor 50a is being advanced out of the needle 156 in its low profile state during delivery, (see, e.g., FIG. 17), while still allowing the user to advance the anchor 50a over the suture 52 under the force provided by the pusher coil 168 when desired during deployment. Similarly, the proximal anchor 50b and cinch 62 are generally maintained in a fixed position on the suture wire 164 spaced apart from the distal anchor 50a during delivery. In addition, the increased rigidity and column strength of the suture wire 164 relative to the suture 52 provides the ability to advance the anchor assembly 48 out of the needle deployment assembly 150 in a controlled manner.

Figure 49:
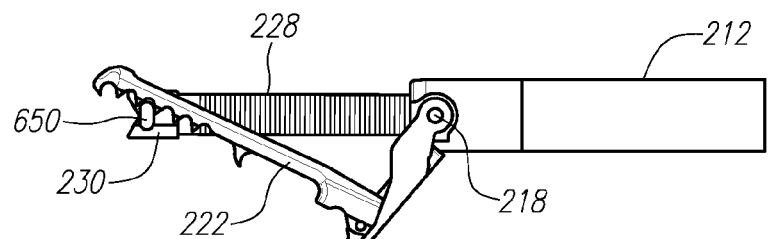
FIG. 49 is a side view of an embodiment of a distal end effector.

Those skilled in the art will appreciate that other breakaway features or suture cutting devices and methods may be suitable for separating the anchor assembly 48 from the delivery device. For example, several suture cutting devices suitable for use with the anchor delivery devices described herein are described in U.S. patent application Ser. No. 11/412,261, filed Apr. 26, 2006, which is hereby incorporated by reference in its entirety. In addition, several embodiments of a cutting device for cutting the suture of an anchor assembly 48 after deployment are shown in FIGS. 49 through 54A-B. For example, FIGS. 49 and 52A-B show an embodiment of an end effector 214 as described previously. This embodiment includes a pivot 230 within which or on which a cutting blade 650 is disposed. The cutting blade 650 is located at or near the distal end of the pivot 230 and is oriented to face generally toward the distal end of the device. In the embodiment shown, the cutting blade 650 has a generally cylindrical shape and is attached, connected to, or formed integrally with the internal surface of the generally cylindrical pivot 230. The distal end of the pivot 230 extends distally of the distal end of the cutting blade 650—i.e., the edge of the cutting blade 650 is generally shielded by the distal end of the pivot 230. The distal end of the pivot 230 includes at least one slot 652 that provides access to the cutting edge of the cutting blade 650. For example, the embodiments shown in FIGS. 49 and 52A-B include three slots 652, two of which are located on opposite sides of the pivot 230 and a third located equidistant between the first two along the upper side of the pivot 230. In the embodiments shown, each slot 652 includes a narrowed opening 654 that is wide enough to accommodate the suture 52 of the anchor assembly 48. In addition, the distal surfaces of the pivot 230 may be tapered in order to guide the suture 52 into the narrowed opening 654 and into the slot 652 where the suture may be engaged by the cutting edge of the cutting blade 650.

Figure 50A:
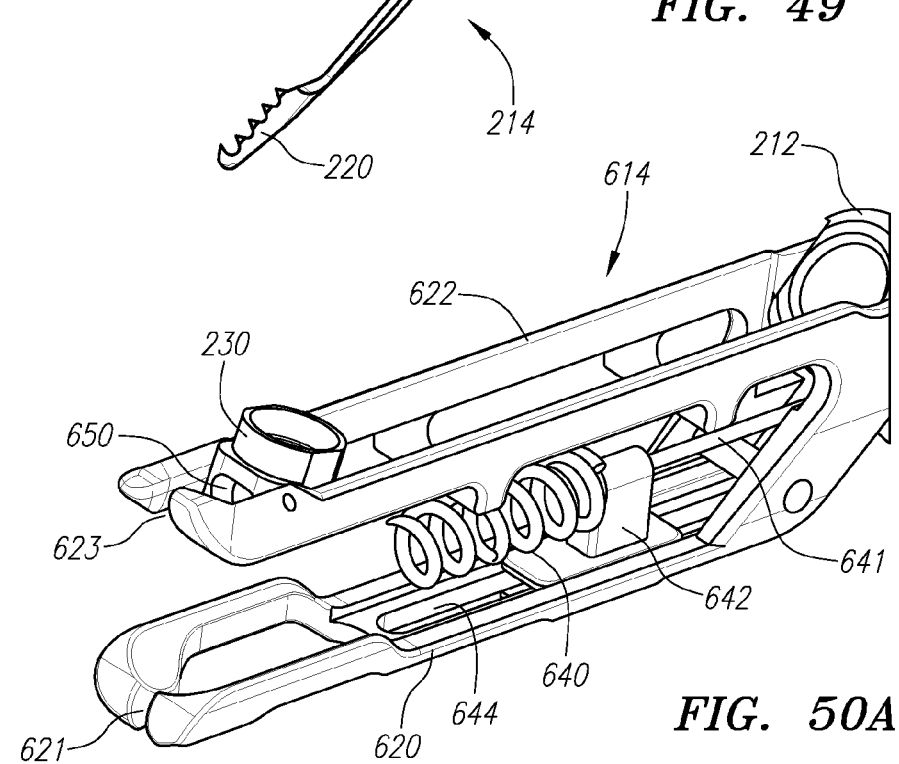
FIGS. 50A-B and 51 are perspective views an alternative embodiment of a distal end effector.
Figure 50B:
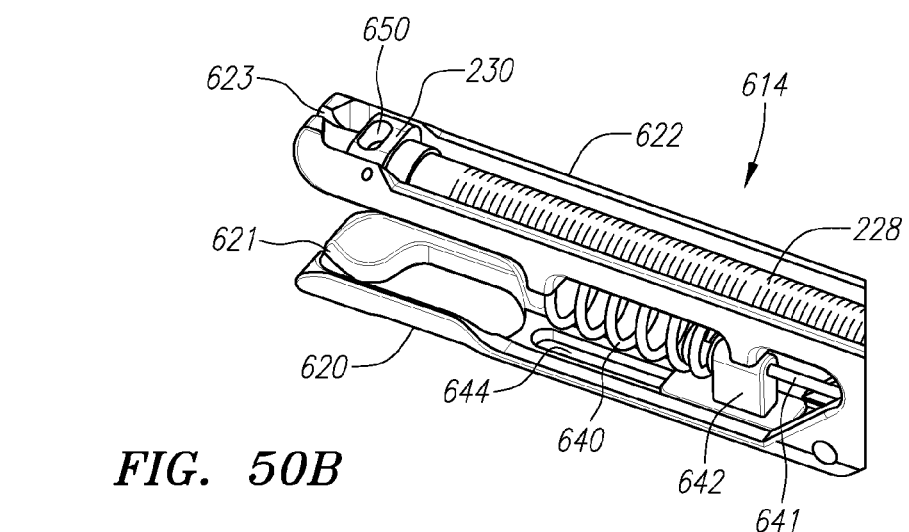
Figure 51:
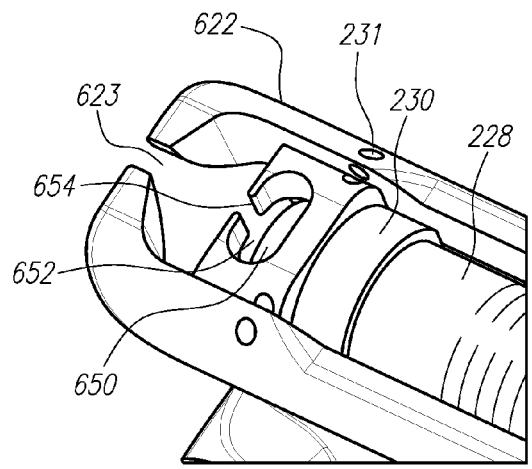
Figure 52A:
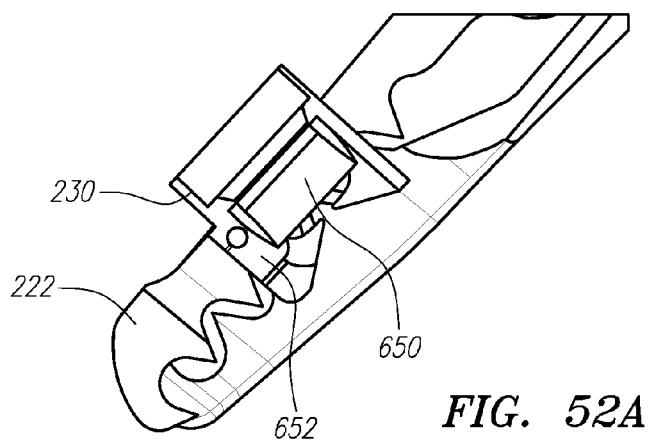
FIGS. 52A-B are a cross-sectional view and a perspective view, respectively, of a portion of the distal end effector shown in FIG. 49.
Figure 52B:
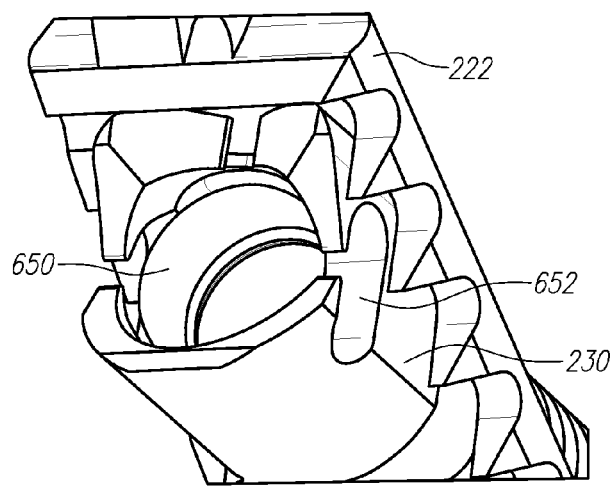
Figure 53A:
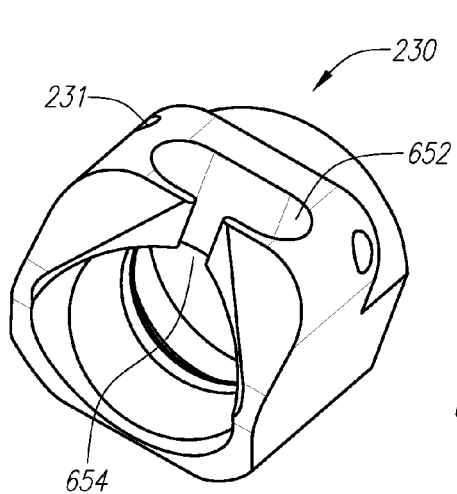
FIGS. 53A-B are a perspective view and a side view, respectively, of an embodiment of a pivot having a cutting blade.
Figure 53B:
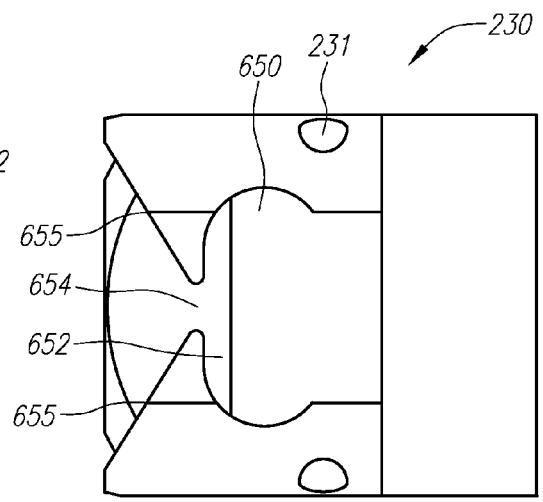
Figure 54A:
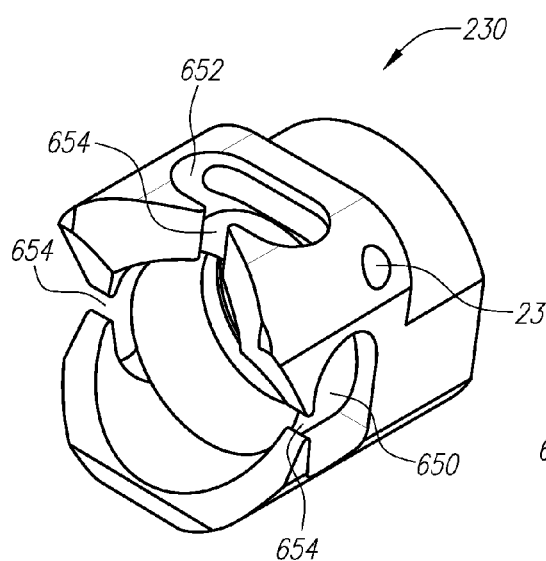
FIGS. 54A-B are a perspective view and a side view, respectively, of another embodiment of a pivot having a cutting blade.
Figure 54B:
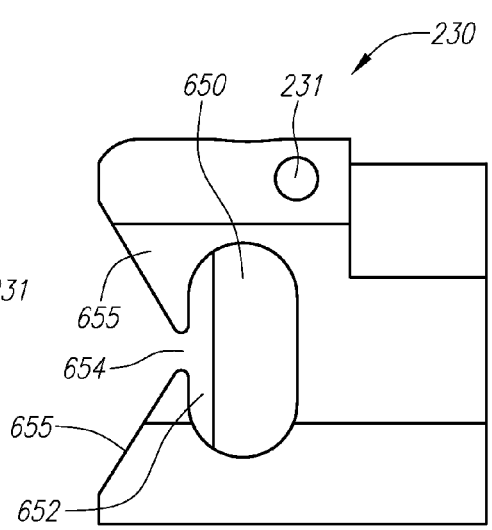

FIGS. 50A-B and 51 show the alternative embodiment of the end effector 614 described above in relation to FIGS. 45A-B through 48A-B. The end effector 614 is provided with a pivot 230 having a cutting blade 650 and one or more slots 652 and narrowed openings 654, as described herein.

Additional details of the pivot 230 and cutting blade 650 are shown in FIGS. 53A-B and 54A-B. In the embodiments shown, the pivot 230 includes a through-hole 231 through which a pin (not shown) extends. The pin, in turn, is attached to opposed sides of an upper jaw member 222 or upper fixed bail 622, and enables the pivot 230 to rotate about an axis defined by the pin. A cutting blade 650 having a distal-facing cutting edge is attached to the internal surface of the pivot 230 such that the cutting edge of the cutting blade 650 is located within the space defined by a slot 652 formed on the pivot 230. (See FIGS. 53B and 54B). A narrowed opening 654 provides access to the slot 652. The distal ends of the pivot 230 are provided with tapered surfaces 655 that lead toward the narrowed opening 654. The embodiment shown in FIGS. 53A-B includes only a single slot 652 and narrowed opening 654 providing access to the cutting blade 650. In the embodiment shown in FIGS. 54A-B, three slots 652 and narrowed openings 654 are provided. Those skilled in the art will appreciate that fewer or more slots 652 and narrowed openings 654 may be included to achieve desired results.

To operate the cutting devices shown in FIGS. 49 through 54A-B, the user deploys an anchor assembly 48 in the manner described herein. After deployment, and while the suture 52 extends from the anchor assembly 48 to the anchor deployment device 208, the user manipulates the end effector 214 to cause the suture 52 to move through a narrowed opening 654 and into one of the slots 652, where it engages the cutting edge of the cutting blade 650. The user then manipulates the tissue manipulation assembly 210 and the anchor assembly 48 so as to cause the cutting edge of the cutting blade 652 to sever the suture 52, thereby releasing the anchor assembly 48 from the device.

Figure 18:
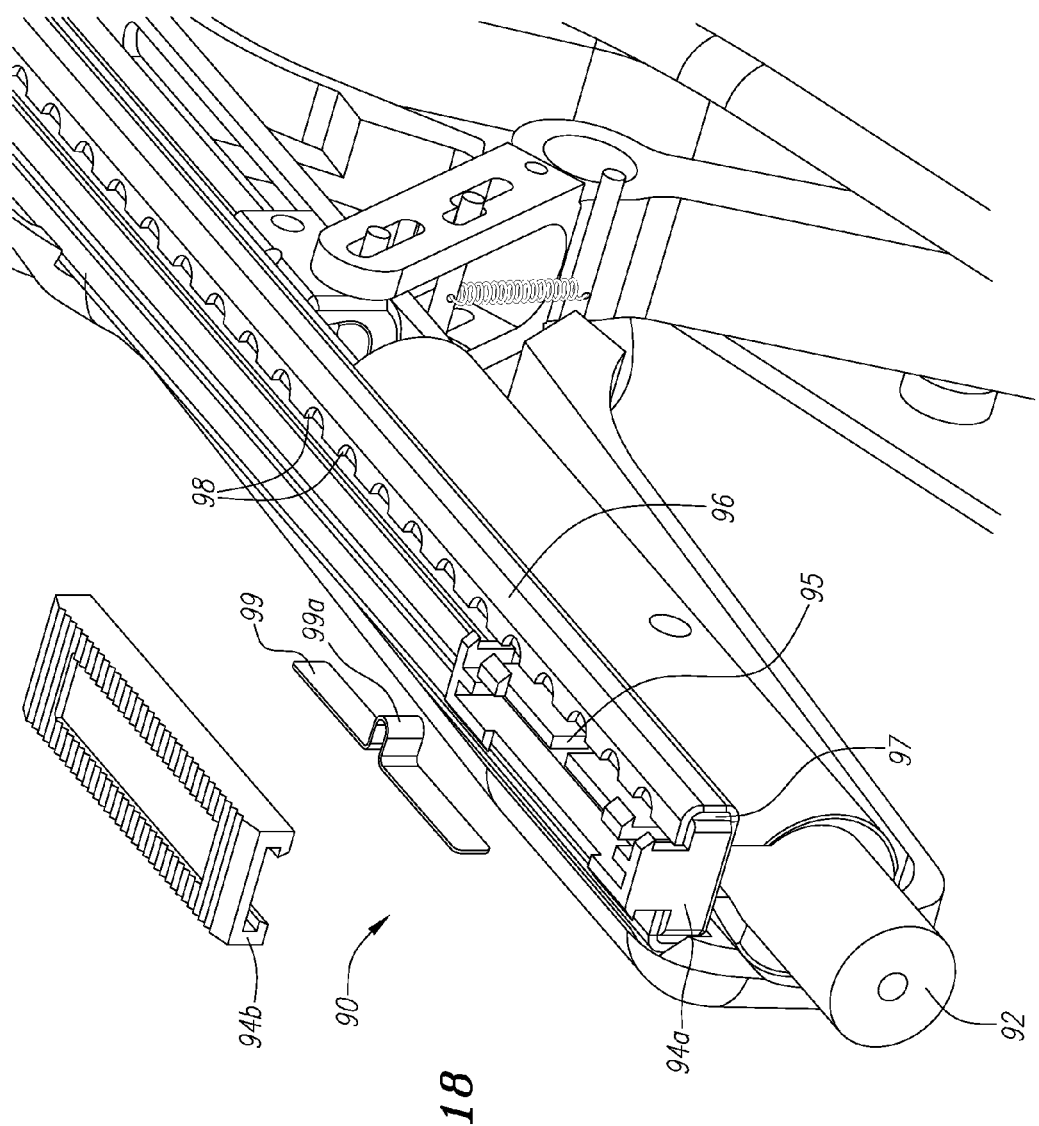
FIG. 18 is an exploded view of a needle deployment assembly actuation mechanism of the actuator mechanism of FIG. 9.

Turning next to FIG. 18, additional details of the structure and operation of the needle deployment assembly actuation mechanism 90 are shown. As described above in relation to FIGS. 9-11, the mechanism includes a needle launch bushing 92 that is slidably retained within the drive channel 122 of the main housing 72, a needle launch track 96 that is fixed to the main housing 72 above the drive channel 122, and a needle launch button 94. The launch track 96 defines a channel 97 in which the button 94 is able to slide longitudinally under control of the user. The button 94 includes a base portion 94*a* and a top portion 94*b* that are attached to each other, with the base portion 94*a* sliding within the launch track channel 97 and the top portion 94*b* extending above the launch track 96 to be accessible to the user. In the embodiment shown, the base portion 94*a* and top portion 94*b* of the button 94 are attached by a tab and slot mechanism, although other attachment mechanisms are also suitable. A needle lock leaf spring 99 is positioned within the button 94. The leaf spring 99 includes a locking tab 99*a* that extends through a leaf spring slot 95 formed in the base portion 94*a* of the button.

The locking tab 99*a* is biased outward through the leaf spring slot 95 to engage one of the cutouts 98 formed on the needle launch track 96. When the locking tab 99*a* is engaged in one of the cutouts 98, the leaf spring 99 prevents the needle launch button 94 from moving along the needle launch track 96. By applying a lateral (longitudinally-directed) force on the top portion 94*b* of the button, the user is able to bias the leaf spring locking tab 99*a* inward, away from the launch track 96, thereby disengaging the tab 99*a* from a cutout 98 and allowing the user to slide the needle launch button 94 within the launch track channel 97. As shown in FIG. 11, the needle launch button 94 is attached by a screw to the needle launch bushing 92. In this manner, movement of the needle launch button 94 causes movement of the needle launch bushing 92 within the drive channel 122. In the embodiment shown, this movement of the needle launch bushing 92 is independent of any movement of the drive bushing 120.

Figure 19:
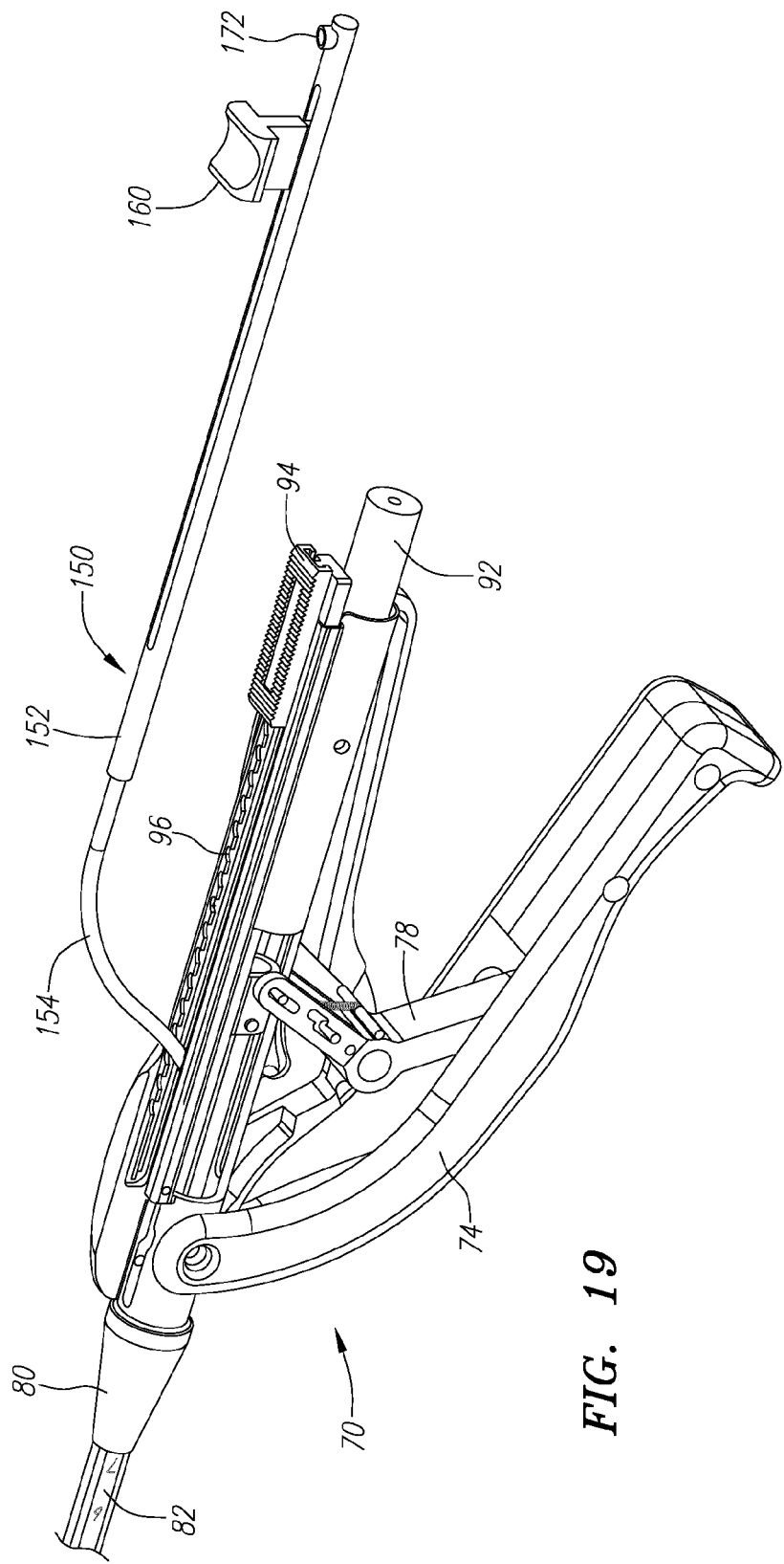
FIG. 19 is a perspective view of a needle deployment assembly being loaded into an actuator mechanism.

Turning next to FIG. 19, the needle deployment assembly 150 is shown being loaded into the actuator mechanism 70. The loading procedure includes inserting the distal end of the needle deployment assembly 150 (i.e., the needle body 156) into the loading channel 124 and directing the needle body 156 and flexible catheter body 154 distally through the lumen defined by the launch tube 228 extending through the tubular body 212. After the rigid body portion 152 is loaded into the loading channel 124, a detent mechanism on the needle launch bushing 92 is rotated to fixedly engage the attachment post 172 on the rigid body 152, thereby attaching the needle deployment assembly 150 to the needle launch bushing 92. In this manner, movement of the needle launch bushing 92 within the drive channel 122 causes movement of the needle deployment assembly 150 relative to and concentrically within the launch tube 228.

Figure 20:
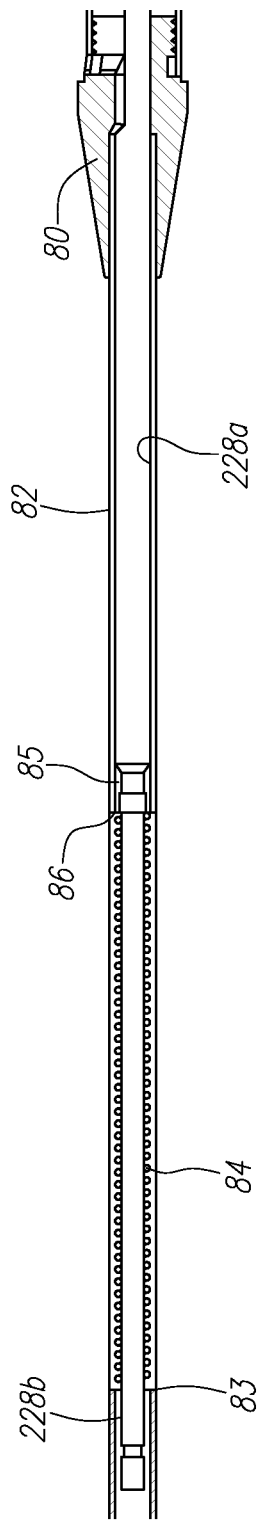
FIG. 20 is a cross-sectional view of a proximal portion of the tubular body of an anchor delivery device.
Figure 26A:
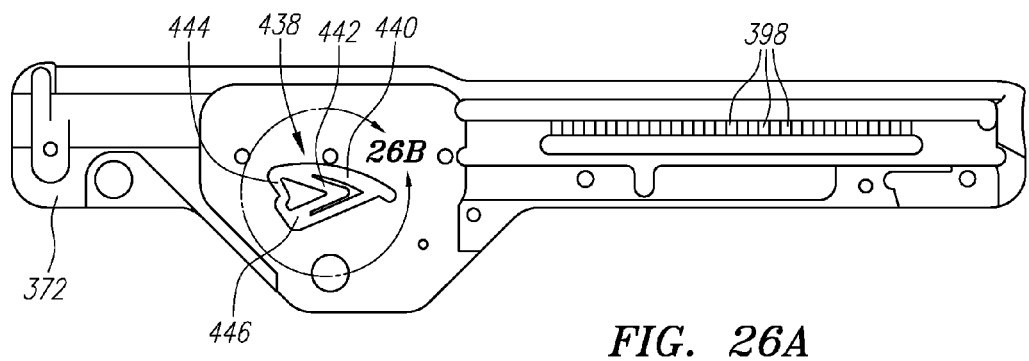
FIGS. 26A-B are side views of a portion of the interior of a main housing of the actuator mechanism of FIG. 21.
Figure 26B:
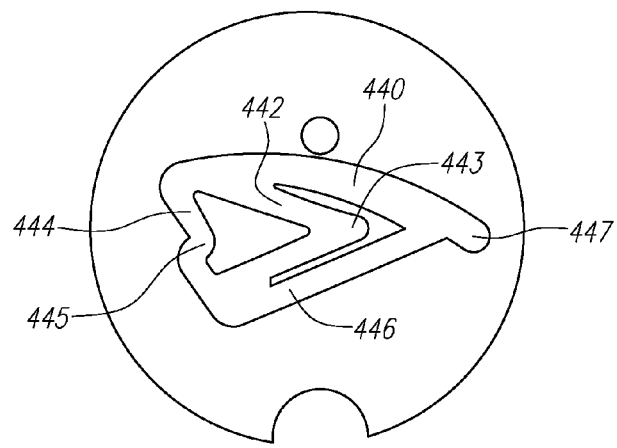

FIG. 20 shows a cross-sectional view of the rigid proximal portion 82 of the tubular body 212 extending from the distal end of the main housing 72. FIG. 20 shows the device prior to loading a needle deployment assembly 150. A distal shoulder 83 is defined on the interior of the tubular body 212 at the point of transition between the rigid proximal portion 82 and the flexible portion of the tubular body 212. The distal end of a launch tube spring 84 rests against the shoulder 83 in the annular space between the rigid proximal portion 82 of the tubular body and the launch tube 228. A needle deployment assembly loading sleeve cap 85 comprises a transition point between a larger diameter portion of the launch tube 228*a* near the proximal end of the device and a smaller diameter portion of the launch tube 228*b* extending distally through the flexible tubular body 212. The loading sleeve cap 85 defines a proximal shoulder 86 against which the proximal end of the launch tube spring 84 abuts. In this manner, when the launch tube 228 is advanced distally, the launch tube spring 84 is compressed between the distal shoulder 83 and the proximal shoulder 86. The spring force of the launch tube spring 84 thereby provides a force biasing the launch tube 228 proximally. This proximally-directed spring force provides resistance against a force squeezing the handle body 74 against the main body 72, thereby biasing the handle body 74 to the open position.

The spring force provided by the launch tube spring 84 also facilitates the operation of the handle lock mechanism 130 described above in relation to FIGS. 12A-G. In particular, the proximally-directed spring force applied to the launch tube 228 is transferred to the locking pin 134 through the drive bushing 120, drive bushing pin 108, and linkage arm 78. This force facilitates the movement of the locking pin 134 proximally through the lower groove 144 during the return portion of the cycle, as shown in FIGS. 12F and 12G. As the locking pin 134 moves proximally within the lower groove 144, the ramped lower surface of the lower groove 144 causes the locking pin 134 also to move upward in the inner portion 112*a* of the locking pin slot in order to return to the starting position in which the locking pin 134 rests on the ledge 112*c*, as shown in FIG. 12A.

The interior of the loading sleeve cap 85 defines a surface against which the distal-most portion of the rigid body portion 152 of the needle deployment assembly 152 abuts during loading of the assembly, while allowing passage of the flexible catheter portion 154 through the lumen defined by the launch tube 228.

Figure 7:
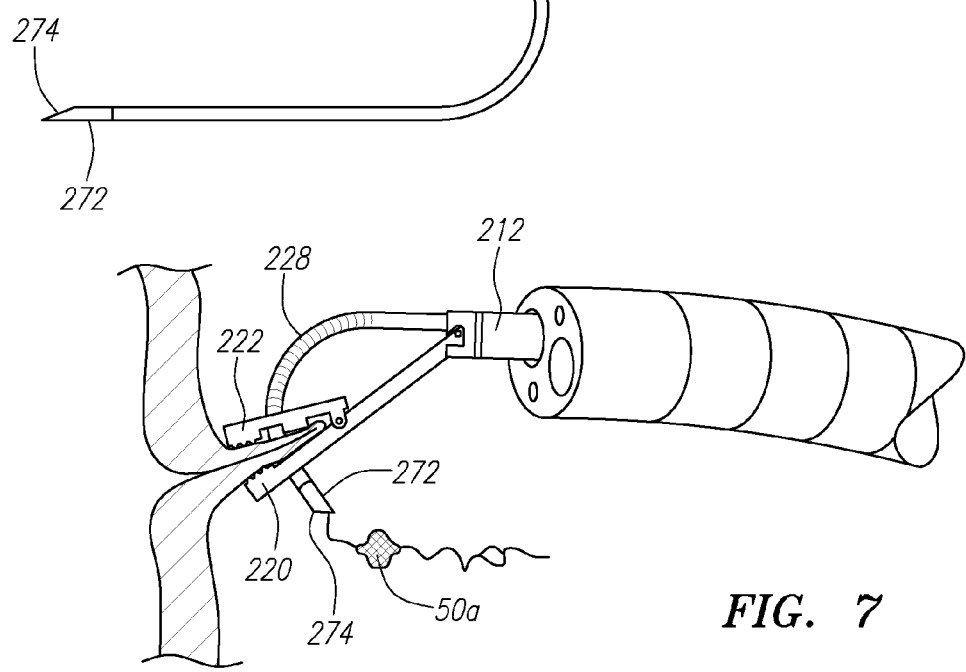
FIG. 7 is a side view of a tissue manipulation assembly extending from the distal end of a lumen of an endoscopic access device and deploying a tissue anchor assembly through a tissue fold.

The combined operation of the actuator mechanism 70 and needle deployment assembly 150 will now be described. As shown in FIG. 7, the end effector 214 is located at a point near a target region of tissue, at which point the jaws 220, 222 are opened under control of the actuator mechanism 70. After the tissue is placed between the jaws 220, 222, the handle body 74 is squeezed toward the main housing 72, which causes the launch tube 228 to advance distally, closing the jaws 220, 222 upon the tissue. The distal portion of the launch tube 228 is also transitioned to an arcuate shape in which the distal opening of the launch tube 228 is positioned substantially perpendicularly to the tissue grasped between the jaws 220, 222. At this point, the locking pin 134 is positioned in the trough 143 of the distal groove 142, thereby maintaining the actuator mechanism 70 in a "closed" position corresponding with a closed position of the jaws 220, 222.

Once the tissue has been grasped and the launch tube 228 positioned as described above, the needle launch button 94 is advanced distally within the launch track 96, thereby causing the needle deployment assembly 150 to be advanced through the launch tube 228. The needle launch button 94 is then locked in place by allowing the leaf spring 99 to engage one of the cutouts 98 of the needle launch track 96. The needle 156 pierces and extends through the tissue, as shown in FIG. 7. In an embodiment, the length of travel allowed for the needle launch button 94 within the launch track 96 is such that the needle 156 is prevented from extending past a desired distance beyond the lower jaw 220. Once the needle 156 is in its proper position, the distal anchor 50a is deployed by advancing the suture deployment button 160 a distance sufficient to extend the distal anchor 51 out of the needle 156 of the needle deployment assembly 150, as shown in FIG. 7. The distal anchor 50a is thereby deployed on the distal side of the tissue fold held by the jaws 220, 222. In the embodiment shown, the length of travel allowed for the suture deployment button within the loading channel 124 when the needle launch button 94 is fully advanced is such that only the distal anchor 50a is advanced out of the needle deployment assembly 150. After the distal anchor 50a is deployed, the needle launch button 94 is retracted, thereby retracting the needle 156 from the tissue and into the launch tube 228. Retraction of the needle launch button 94 also causes the suture deployment button 160 to be retracted within the loading channel 124. The jaws 220, 222 are disengaged from the tissue by squeezing and releasing the handle body 74 and main housing 72. As a result, the suture 52 extends through the tissue as the proximal anchor 50b remains within the needle deployment assembly 150. The proximal anchor 50b may then be deployed.

As noted above, the action of retracting the needle launch button 94 also retracts the suture deployment button 160 within the loading channel 124. Accordingly, the suture deployment button 160 is now able to be advanced distally, causing the proximal anchor 50b to be extended outside of the needle body 156 and the needle deployment assembly 150. (See, e.g., FIG. 13B). The proximal anchor 50b is located on the proximal side of the tissue fold. At this point, the pusher coil bushing set screw 170 is locked in place, thereby locking in place the pusher coil bushing 166 and pusher coil 168. The needle deployment button 160 is then withdrawn proximally, causing the suture wire 164 to be withdrawn relative to and through the pusher coil 168. This action causes the suture 52 to be retracted proximally through the distal anchor 50a, proximal anchor 50b, and the cinch 62, thereby fully deploying the anchor assembly 48. (See, e.g., FIGS. 14C, 15C, and 16A-B). The anchor assembly 48 is thereby deployed to retain a tissue fold F, as shown schematically in FIG. 1B. Further retraction of the suture deployment button 160 creates sufficient tensile stress on the suture wire 164 to break the shrink wrap 178 at the junction 176, leaving a relatively short tail of suture 52 extending proximally of the proximal anchor 50b.

Turning to FIGS. 21-36, another embodiment of an actuator mechanism 370 for a tissue anchor delivery device 208 is shown. The actuator mechanism 370 comprises another alternative embodiment to the handle 216 described above in relation to FIGS. 3 and 4 and the actuator mechanism 70 described above in relation to FIGS. 9-20. In the embodiment shown, the actuator mechanism 370 is configured to actuate both the tissue manipulation assembly 210 and the needle deployment assembly 260 independently of one another in order to grasp tissue and deploy a tissue anchor assembly 48 in separate steps. The actuator mechanism 370 also includes a number of additional features that will be described in relation to the Figures.

Turning first to FIGS. 21, 22A-B, and 44A-C, the illustrated actuator mechanism 370 includes a main housing 372 and a handle body 374 that is pivotably attached to the main housing by a hinge pin 376, such that a user is able to grasp the main housing 372 and handle body 374 in one hand and actuate the mechanism by pulling the handle body 374 toward the main housing 372. A linkage arm 378 is interposed between the main housing 372 and the handle body 374, as discussed in more detail below. A nose cone 380 is attached to the distal end of the main housing 372 and surrounds the proximal end 82 of the tubular body 212.

In the embodiment shown in FIGS. 44A-C, the actuator mechanism 370 includes several features that assist the user in gripping the device and utilizing the actuator mechanism. For example, the main housing 372 includes a distal finger rest 373 located at the distal end of the main housing 372. The distal finger rest 373 comprises a raised surface formed on the underside of the main housing (i.e., the side of the main housing to which the handle body 374 is attached). The raised surface of the distal finger rest 373 defines a small pocket 373a on the underside of the main housing 372 at the location on the actuator mechanism 370 upon which the user's index finger wraps around the main housing 372 when the user is holding the mechanism in a "palm-down" orientation (i.e., palm on topside, fingers wrapped around underside, distal end of the actuator mechanism extending through the hand beyond the thumb and index finger). In this way, the distal finger rest 373 provides the user with additional tactile information and improved control over the tissue manipulation assembly 210 when the user is holding the actuator mechanism in the "palm-down" orientation. In addition, the handle body 374 includes a proximal finger rest 375 located near a proximal end of the handle body 374. The proximal finger rest 375 comprises a raised surface formed on the underside of the handle body 374 (i.e., the side facing away from the main housing 372). The raised surface of the proximal finger rest 375 defines a small pocket 375a on the underside of the handle body 374 at the location on the actuator mechanism 370 upon which the user's index finger wraps around the handle body 374 when the user is holding the mechanism in a "palm-up" orientation (i.e., palm on underside, fingers wrapped around topside, distal end of the actuator mechanism extending through the hand beyond the little finger and the heel of the palm). In this way, the proximal finger rest 375 provides the user with additional tactile information and improved control over the tissue manipulation assembly 210 when the user is holding the actuator mechanism in the "palm-up" orientation.

During some forms of use of the tissue manipulation assembly 210, the user will hold the actuator mechanism with a single hand in the palm-down orientation in order to deploy the device to a treatment location, and to operate the handle body 374. The user is then able to reposition the actuator mechanism 370 in the same hand to the palm-up orientation in order, for example, to operate the needle launch button 394 and/or the suture deployment button 460 (as described below) with the thumb of the same hand. The distal finger rest 373 and proximal finger rest 375 facilitate these actions by providing support and tactile information during the respective procedures.

In the embodiment shown, the proximal end 82 of the tubular body 212 is formed of a rigid material such as a rigid polymer material or stainless steel tubing. The remainder of the tubular body 212 is flexible and is formed of materials used to form the insertion portion of endoscopes and endoscopic devices. In alternative embodiments, such as those described previously, the tubular body portion is formed of a composite tube that includes one or more polymeric materials (e.g., Pebax) and one or more braided layers (e.g., stainless steel or polymeric braid) to provide the tubular body 212 with improved torque transmission and resistance to stretching.

A needle deployment assembly actuation mechanism 390 includes a needle launch button 394, and a needle launch track 396. The needle launch track 396 includes a plurality of substantially equally spaced, scallop-shaped cutouts 398 formed along the length of the track 396. More details of the structure and function of the needle deployment assembly actuation mechanism 390 are provided below.

FIGS. 23, 24, and 25A-B show additional details concerning the structure and operation of the actuator mechanism 370. The linkage arm 378 is pivotably mounted to the main housing 372 by a linkage arm pivot pin 402, about which the linkage arm 378 is able to rotate. The linkage arm 378 includes a hub portion 378a, a drive arm 378b extending from the hub 378a substantially toward the central portion of the main housing 372, and a handle arm 378c extending from the hub 378a substantially toward the handle body 374. In the embodiment shown, the drive arm 378b and the handle arm 378c connecting through the hub portion 378a define an acute included angle, i.e., a "V"-shape. A handle body pin 404 is mounted on and extends from the handle body 374 through a handle arm slot 406 formed on the handle arm 378c. A drive bushing pin 408 is mounted on a drive bushing 420 and extends from the drive bushing 420 through a drive arm slot 410 formed on the drive arm 378b.

The drive bushing 420 resides in and travels through a drive channel 422 formed in the main housing 372. More particularly, the external size and shape of the drive bushing 420 closely matches the internal size and shape of the drive channel 422 such that the drive bushing 420 is able to slide through the drive channel 422 along the longitudinal axis of the main housing 372. The drive bushing 420 is attached to (or formed integrally with) the proximal end of the launch tube 228, which extends through the drive channel 422 and the tubular body 212 to the end effector 214, as described above in relation to FIGS. 4 and 5A-B. In the embodiment shown, the drive bushing 420 and the proximal portion of the launch tube 228 (e.g., the portion of the launch tube extending through the drive channel 422 in the main housing 372) each includes an upward-facing opening defining an actuation channel 424 providing a pathway for passage of an actuator button of a needle deployment catheter, as described more fully below.

During operation, as the handle body 374 is moved toward the main housing 372 (by rotating the handle body 374 around the hinge pin 376), the handle body pin 404 causes the linkage arm 378 to rotate counterclockwise (as viewed in FIG. 23), thereby driving the drive bushing 420 toward the distal end of the device (i.e., toward the left as viewed in FIG. 23). This action causes the launch tube 228 to translate distally, e.g., from the jaws open position illustrated in FIG. 5B to the jaws closed and launch tube pivoted position illustrated in FIG. 5A. In this way, the action of squeezing the handle body 374 toward the main housing 372 causes the actuation mechanism 370 to actuate the launch tube 228 which action causes the lower jaw 220 and upper jaw 222 of the end effector 214 to grasp and manipulate tissue. The squeezing action also causes the portion of the launch tube 228 that extends distally from the tubular body 212 to rotate at the hinge or pivot 230 and reconfigure itself such that the exposed portion forms a curved or arcuate shape that positions the launch tube opening substantially perpendicularly relative to the upper jaw member 222. (See, e.g., FIG. 5A). This position facilitates delivery of the anchor assembly 48, as described above and below.

The actuation mechanism 370 embodiment shown in the drawings also includes a handle lock mechanism 430 that is configured to maintain the position of the handle body 374 relative to the main housing 372 at one or more positions during operation of the actuation mechanism 370. The handle lock mechanism 430 is illustrated in FIGS. 23, 25A, and 26A-B, which illustrate several positions of the handle lock mechanism that occur during a selected cycle of the actuation mechanism 370. The handle lock mechanism 430 includes a stationary pin 432 that is fixed to (or formed integrally with) the main housing 372, and a locking pin 434 that is neither fixed to nor formed integrally with the main housing 372. A locking pin spring (not shown for clarity) is connected at one end to the stationary pin 432 and at its other end to the locking pin 434, thereby providing a force biasing the locking pin 434 toward the location of the stationary pin 432. The locking pin 434 extends through a locking pin slot 412 formed through the drive arm 378b between the hub 378a and the drive arm slot 410. The locking pin slot 412 includes and outer portion 412a and an inner portion 412b, with a ledge 412c located at the transition between the outer portion 412a and the inner portion 412b.

In the embodiment shown, the handle lock mechanism 430 also includes a locking pin track 438. The locking pin track 438 comprises a set of grooves and raised surfaces formed on at least one of the inner facing surfaces of the main housing 372. The locking pin 434 extends into one or more of the grooves defined by the locking pin track 438 such that the track 438 limits the movement of the locking pin 434. In the illustrated embodiment, the track 438 includes an upper track 440, an inner track 442, an outer track 444, and a lower track 446. Together, the upper track 440, inner track 442, outer track 444, and lower track 446 form a substantially triangular shape in which each of the inner and outer tracks is operatively connected at an intersection to each of the upper and lower tracks. As described below, positioning the locking pin 434 at the proximal end 447 of the upper track 440 corresponds with the "fully open position" in which the jaws of the end effector are open. (See FIG. 5B). From there, translation of the locking pin 434 along and through the upper track 440 corresponds with movement of the handle body 374 toward the main housing 372 and, concurrently, movement of the launch tube 228 distally toward the end effector 214. Positioning the locking pin 434 within the inner track 442 corresponds with placing the handle in a "parked" or "neutral" position in which the jaws of the end effector are closed, but the launch tube is not pivoted. (See, e.g., FIG. 4). Positioning the locking pin 434 within the outer track 444 corresponds with the fully closed position in which the jaws are closed and the launch tube pivoted and curved into the position illustrated in FIG. 5A. Finally, translation of the locking pin 434 along and through the lower track 446 corresponds with movement of the handle body 374 away from the main housing 372 and, concurrently, movement of the launch tube 228 proximally.

FIG. 23 shows a starting position of the locking mechanism 430 in which the drive arm 378b is at its proximal-most position. The locking pin 434 is positioned within the outer portion 412a of the locking pin slot and is at the fully open position 447 near the intersection of the upper track 440 and lower track 446. As the handle body 374 and main housing 372 are squeezed together, the linkage arm 378 rotates counterclockwise (as shown in FIG. 23). This motion causes the drive arm 378b to move the locking pin 434 generally distally. The locking pin spring provides a generally downward and proximally-directed force (as shown in FIG. 23) on the locking pin 434, causing the locking pin 434 to rest upon the ledge 412c of the locking pin slot. The radial position of the ledge 412c on the drive arm 378b causes the locking pin 434 to translate through the upper track 440, rather than the lower track 446, as the locking pin 434 traverses the intersection of the two tracks and beyond.

As the locking pin 434 traverses the upper track 440, the ramped surface of the upper track biases the locking pin 434 radially outward in the outer portion 412a of the locking pin slot, i.e., away from the ledge 412c. Further squeezing of the handle body 374 and main housing 372 causes the locking pin 434 ultimately to reach the inner track 442, upon which the force of the locking pin spring 436 causes the locking pin 434 to slide into the inner track 442 until the locking pin 434 again encounters the ledge 412c of the locking pin slot. At this point, if the handle body 374 is released, the locking pin 434 will settle into the inner track trough 443, corresponding with the "neutral position." The end effector 214 will remain in the neutral position upon release of the handle 374. An additional activation of the handle 374 will drive the locking pin 434 distally through the lower portion of the inner track 442 until the locking pin 434 slides into the lower track 446, at which point the handle body 374 may be released and the actuator mechanism 370 returned to the "fully open position." The foregoing cycle corresponds with a transition from the "fully open position" to the "neutral position" and returning again to the "fully open position."

In an alternative cycle, the locking pin 434 starts at the fully open position 447 and is advanced by the linkage arm 378 so that the locking pin 434 traverses the upper track 440. The ramped surface of the upper track biases the locking pin 434 radially outward in the outer portion 412a of the locking pin slot, i.e., away from the ledge 412c. Further squeezing of the handle body 374 and main housing 372 causes the locking pin 434 ultimately to reach the outer track 444 of the locking pin track 438, preventing any further rotation of the handle body 374 relative to the main housing 372. As the user releases the squeezing action on the handle body 374, the linkage arm 378 will rotate slightly in the clockwise direction (as shown in FIG. 23), releasing the locking pin 434 from the ledge 412c of the locking pin slot and into the trough 445 formed in the outer track 444, corresponding with the "fully closed position," where it is retained under the force of the locking pin spring 436. Upon re-squeezing by the user of the handle body 374 relative to the main housing 372, the edge of the inner portion 412b of the locking pin slot engages the locking pin 434, forcing the locking pin 434 out of the trough 445 of the outer track. The spring force of the locking pin spring 436 pulls the locking pin 434 downward from the outer track 444 into the intersection of the outer track 444 with the lower track 446. As the handle body 374 is released by the user, the linkage arm 378 rotates clockwise (as shown in FIG. 23) and the locking pin 434 is allowed to traverse the lower track 446 proximally until the locking pin 434 returns to the starting position. The foregoing cycle corresponds with a transition from the "fully open position" to the "fully closed position" and returning again to the "fully open position."

Those skilled in the art will recognize that the handle lock mechanism 430 embodiment described herein may be modified to provide a range of movement different from that provided by the embodiment shown in order to support other and different functions or processes to be performed by the device associated with the actuator mechanism 370. For example, a single cycle may include more or fewer grooves and intersections. Variations of other parameters and components are also possible.

As shown in FIGS. 21 and 22A, the exterior surface of the main housing 372 includes a plurality of handle position indicator windows, including a "fully open window" 373a, a "neutral position window" 373b, and a "fully closed window" 373c. Each of the windows comprises an opening into the interior of the main housing 372 that is located within the travel path of the drive arm 378b of the linkage arm. Accordingly, as the actuator mechanism 370 is transitioned between the fully open, neutral, and fully closed positions, the drive arm 378b is located within the corresponding window, thereby providing a visual indicator on the main housing 372 of the position of the actuator mechanism 370. The position indicator may be highlighted by providing a lighted, brightly colored, or otherwise visually observable member on the drive arm 378b in a position observable through the windows 373a, 373b, 373c.

Turning to FIGS. 23 through 27A-D, the structure and function of a needle stop assembly and a handle stop assembly of the actuator mechanism 370 will be described. The needle stop assembly operates to prevent translation of the needle launch button 394 when the actuator mechanism 370 is not in the "fully closed position." This prevents unintended advancement of the needle deployment assembly 450 prior to tissue engagement. The handle stop assembly operates to prevent the handle body 374 from being transitioned out of the fully closed position when the needle deployment assembly 450 is in anything other than the fully retracted position.

Figure 27A:
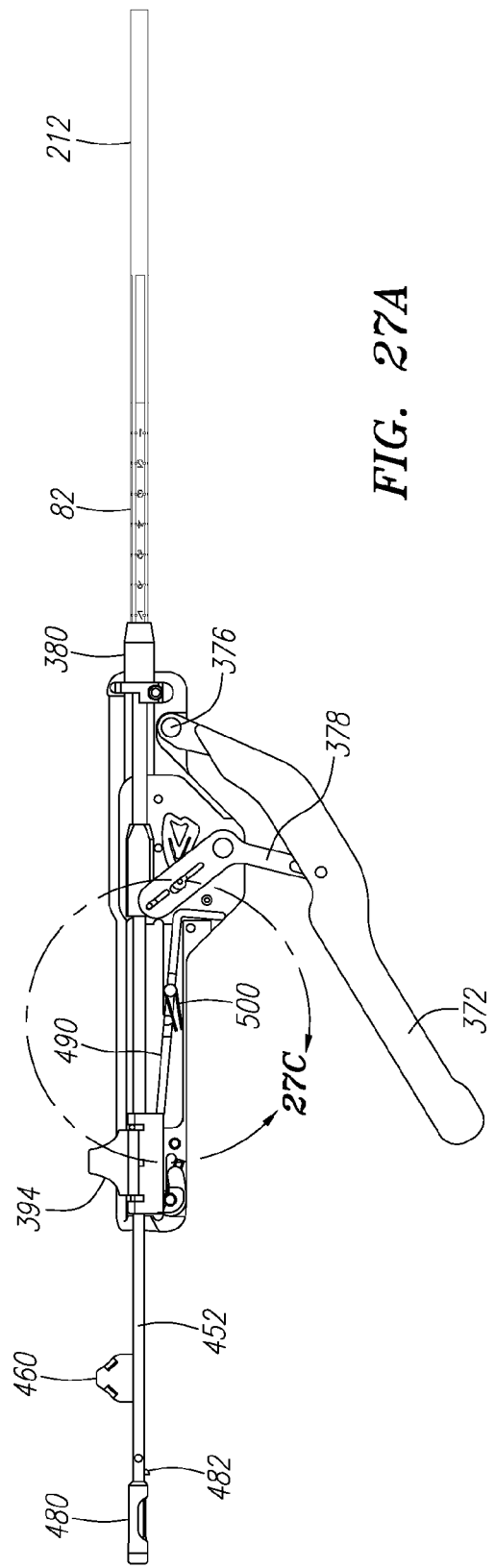
FIGS. 27A-C are side views of the actuator mechanism of FIG. 21 (with portions of the main housing removed for clarification) including a needle deployment assembly being loaded into the proximal end of the device.
Figure 27B:
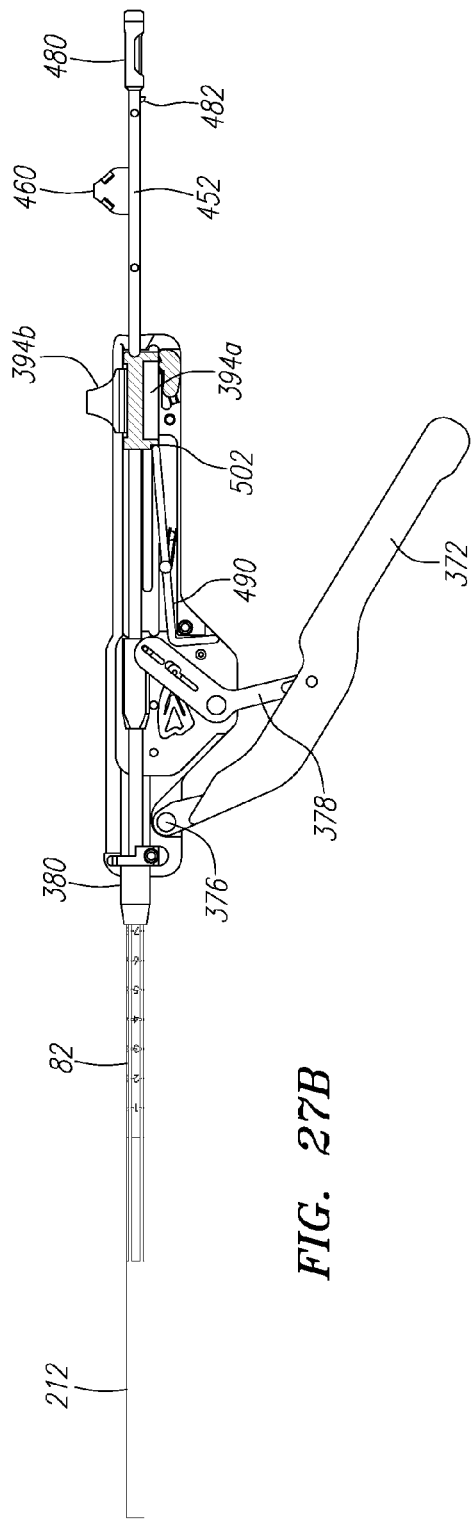
Figure 27D:
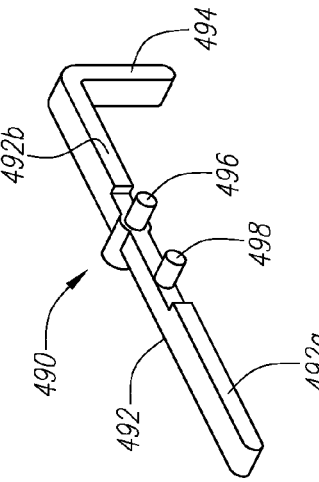
FIG. 27D is a perspective view of an embodiment of a needle stop arm.
Figure 27C:
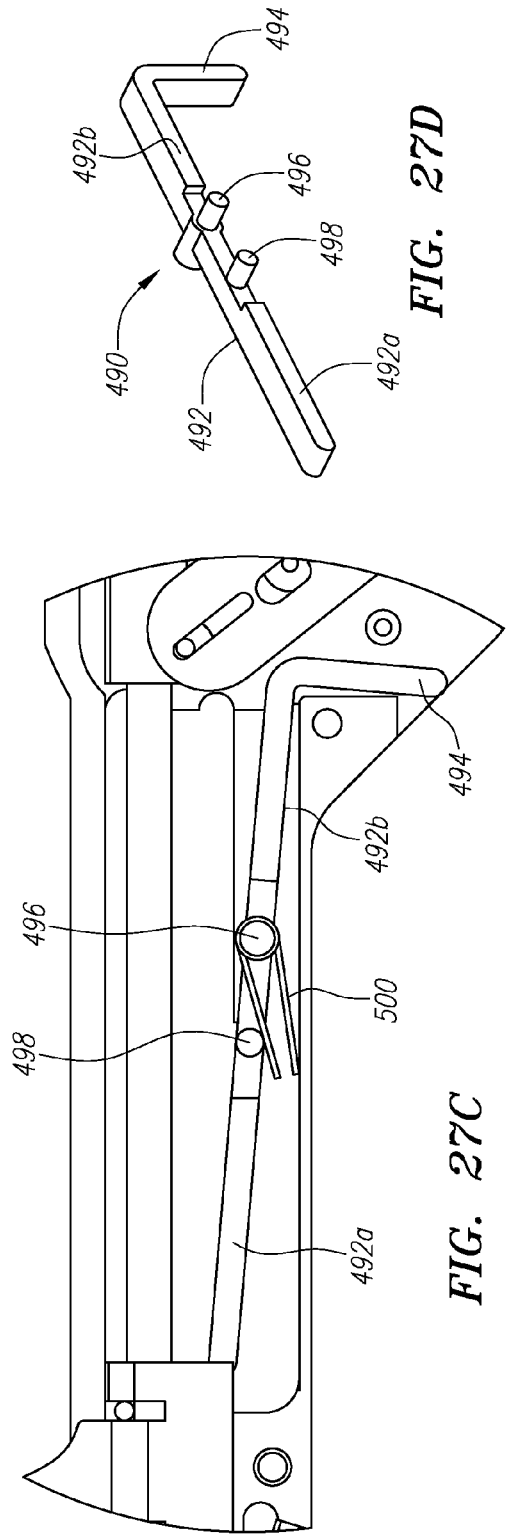
Figure 29A:
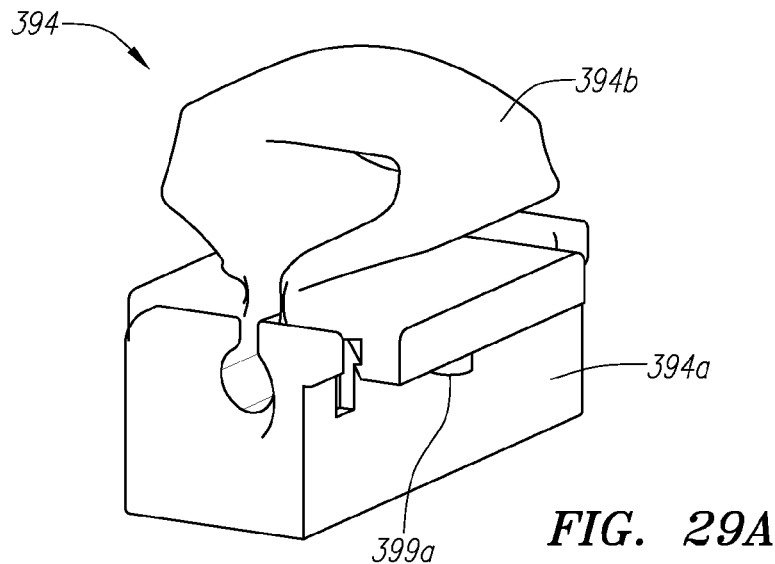
FIGS. 29A-C are a perspective view and two bottom views of an embodiment of a needle launch button.
Figure 29B:
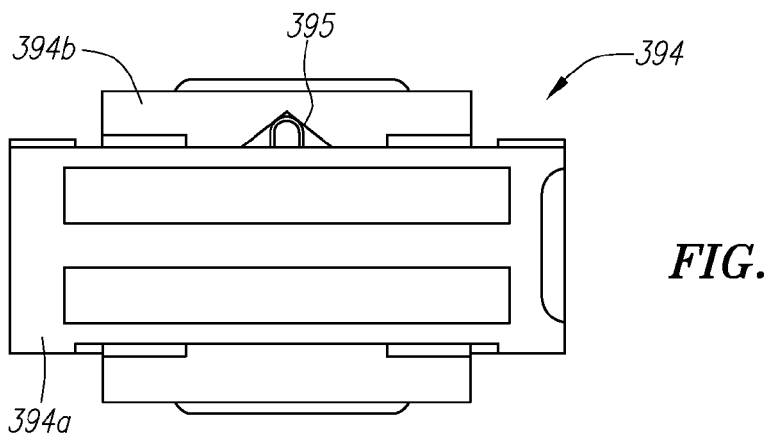
Figure 29C:
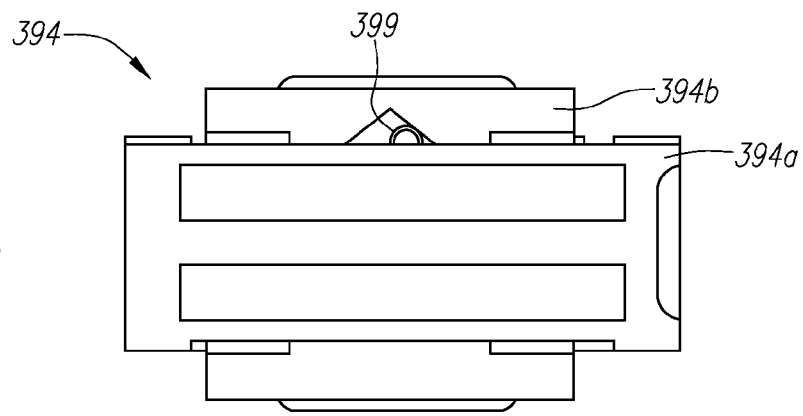

First, the needle stop assembly includes a needle stop arm 490 that is pivotably attached to or mounted within the main housing 372. The needle stop arm 490 is a substantially "L"-shaped member having a longitudinal leg 492 and a transverse leg 494. A pivot pin 496 or other suitable member extends transversely from at least one side of the longitudinal leg 492 to provide a pivot axis about which the needle stop arm 490 is able to pivot upon attachment or mounting within the main housing 372. The pivot pin 496 also bisects the longitudinal leg 492 into a proximal section 492a and a distal section 492b. A spring pin 498 or other suitable member also extends transversely from at least one side of the longitudinal leg 492 to provide an abutment surface for a stop member torsion spring 500 that is mounted on the pivot pin 496, as shown in FIGS. 27A and 27C. In the embodiment shown, the spring pin 498 is located on the proximal section 492a of the longitudinal leg 492. The torsion spring 500 also abuts an inner surface of the main housing 372 to thereby provide a stop member torsion spring force that tends to rotate the needle stop arm 490 in the clockwise direction (from the perspective of FIGS. 27A and 27C) around the axis of the pivot pin 496.

During operation, the needle stop arm 490 is in the engaged position illustrated in FIGS. 23 and 27A when the handle body 374 is in the open position relative to the main housing 372. In the engaged position, the proximal tip of the proximal section 492a engages a distal pocket 502 or the distal-facing portion of the base portion 394a of the needle launch button, thereby preventing distal movement of the needle launch button 394 relative to the main housing 372. The needle stop arm 490 remains in the engaged position, under the biasing force of the needle stop torsion spring 500, until it is acted upon by the linkage arm 378. This occurs when the handle body 374 is moved to the closed position relative to the main housing 372 as shown, for example, in FIG. 24. At that point, the handle body arm 378c engages the downward facing transverse leg 494 of the needle stop arm, driving the transverse leg 494 upward (from the perspective of FIG. 24) and rotating the needle stop arm 490 in the clockwise direction (from the perspective of FIG. 24). This rotation causes the proximal tip of the proximal section 492a to disengage from the distal pocket 502 (or other engagement surface) of the base portion 394a of the needle launch button, thereby allowing the needle launch button 394 to be translated in the distal direction. The needle launch button 394 remains free to translate within the housing 372 until the needle launch button 394 is moved to the proximal starting position (shown, for example, in FIGS. 23 and 27A-B) and the handle body 374 is moved from the closed position.

Turning next to the handle stop assembly, the assembly includes a handle stop arm 510 that is rotatably attached to or mounted within the main housing 372 near its proximal end. The handle stop arm 510 is located beneath the needle launch button 394 when the needle launch button 394 is in its proximal-most location, corresponding with the needle deployment assembly 450 being fully retained within the actuator mechanism 370. The handle stop arm 510 is rotatably supported by and rotates around an axis defined by a pivot pin 512. A handle stop torsion spring 514 is mounted over the pivot pin 512 and has a first leg that is fixed within or abutting against a portion of the interior of the main housing 372 and a second leg that abuts a portion of the handle stop arm 510 to provide a spring biasing force tending to cause the handle stop arm 510 to rotate counterclockwise (from the perspective of FIGS. 23 and 24) around the axis defined by the pivot pin 512.

During operation, the handle stop arm 510 is in the retracted position illustrated in FIGS. 23 and 24 when the needle launch button 394 is in the proximally-retracted position relative to the main housing 372. In the retracted position, the handle stop arm 510 is disposed fully within a recess 516 formed in the underside of the main housing 372 and is retained there against the spring force of the torsion spring 514 by the underside of the base portion 394a of the needle launch button 394. Once the needle launch button 394 is advanced distally, the handle stop arm 510 is free to rotate counterclockwise (from the perspective of FIGS. 23 and 24) under the biasing force of the torsion spring 514 until the handle stop arm 510 projects downward from the underside of the main housing 372, as shown in FIG. 24. Rotation of the handle stop member 510 is limited by an engagement of the distal surface 511 of the handle stop arm against a proximal stop surface 518 defined by the main housing 372. When the needle launch button 394 is returned to the proximal position, the underside of the base portion 394a once again engages the handle stop arm 510 and causes the handle stop arm 510 to rotate clockwise (from the perspective of FIGS. 23 and 24) to return to the retracted position. In this way, the handle stop arm 510 is able to prevent the handle body 374 from being activated from the fully closed position (shown in FIG. 24) unless the needle actuator button 394 is in the fully retracted position, corresponding with full retraction of the needle deployment assembly 450 within the actuator mechanism 370.

Turning next to FIGS. 30-36, another embodiment of a needle deployment assembly 450 is shown. The needle deployment assembly 450 is configured for use with the actuator mechanism 370 described above in relation to FIGS. 21 through 29. The assembly 450 includes a rigid body portion 452 and a flexible catheter portion 454 extending distally from the distal end of the rigid body portion 452. A needle 456 is fixed to the distal end of the catheter portion 454. The upper surface of the rigid body portion 452 includes an elongated groove 458 that provides access into the generally tubular rigid body 452. A suture deployment button 460 extends from the interior of the rigid body portion 452 through the groove 458.

In the embodiments shown, the suture deployment button 460 is attached to or formed integrally with a cable bushing 462 that is concentrically and slidably retained within an internal lumen defined by the rigid body portion 452 of the assembly. The cable bushing 462 is attached by a snap connect 463 to a cinch bushing 466, which is attached to a section of hypo tube 467 having an elongated pusher coil 466 attached at its opposite end. The combined assembly of the cable bushing 462, hypo tube 467, and pusher coil 466 is aligned and has a shape and size adapted to slide coaxially within the rigid body portion 452 and flexible catheter portion 454, as explained more fully below. The cable bushing 462 includes an internal counterbore 470 and a cable lumen 472 extending through the proximal end of the bushing 462. A looped cable 464 (e.g., nitinol, stainless steel, cable, or braid) extends concentrically through the pusher coil 466, hypo tube 467, and through the cable lumen 472 and into the void formed by the counterbore 470 of the cable bushing 462. A crimp tube 465 or other suitable retaining member is formed on the proximal end of the looped cable 464 and has a size and shape that prevents the crimp tube 465 from passing distally through the cable lumen 472. In the embodiment shown, the pusher coil 466 is a coiled wire defining a central lumen through which the looped cable 464 extends substantially concentrically.

Turning next to FIGS. 36A-C, the structure of the anchor assembly 48 is shown. The anchor assembly 48 includes a distal anchor 50a, a proximal anchor 50b, a suture 52, and a cinch 62. A knot 54 is formed at the distal end of the suture 52. A proximal end of the suture 52 is releasably attached to a distal end of the looped cable 464 in a manner described below.

Figure 30A:
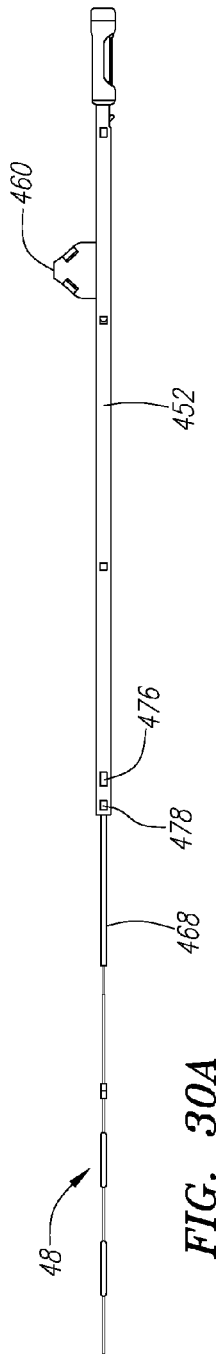
FIGS. 30A-C are two side views and a top view, respectively, of an embodiment of a needle deployment assembly, with the outer sheath removed for clarification.
Figure 30B:
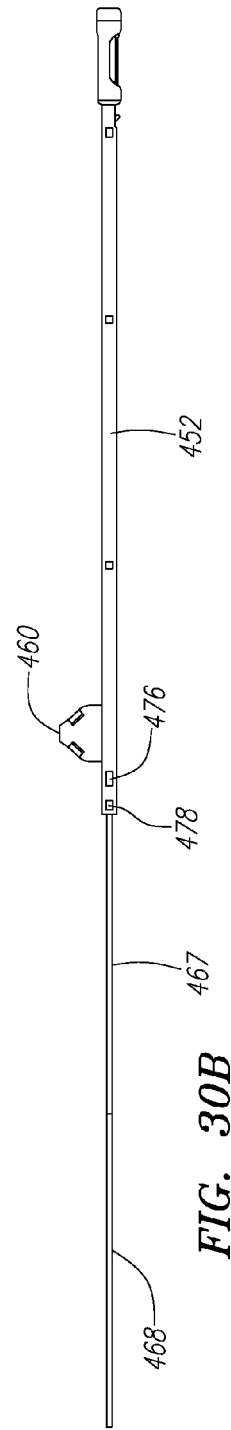
Figure 30C:
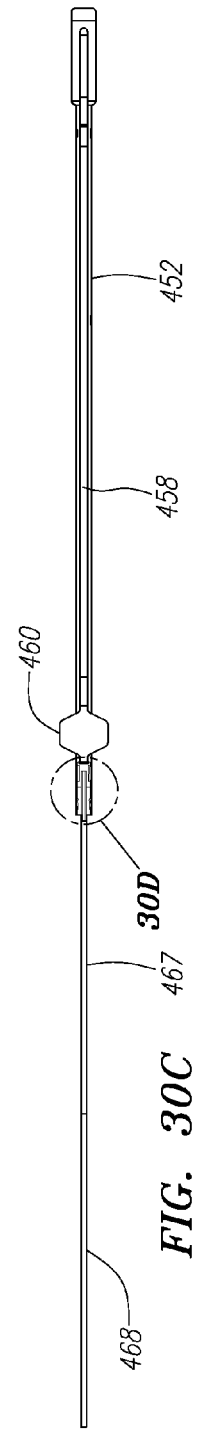
Figure 30D:
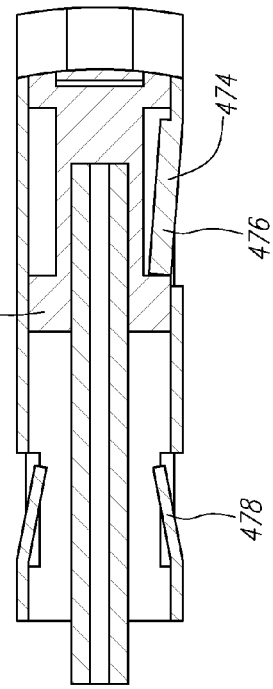
FIG. 30D is a cross-sectional view of an embodiment of a one way snap feature of the needle deployment assembly of FIGS. 30A-C.
Figure 31A:
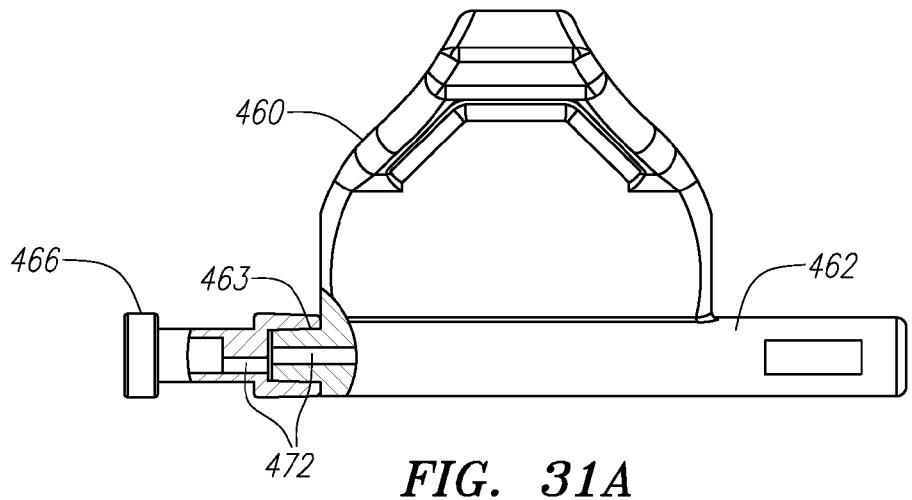
FIGS. 31A-C are side, top, and perspective views, respectively, of an embodiment of a suture deployment button of the needle deployment assembly of FIGS. 30A-C.
Figure 31B:
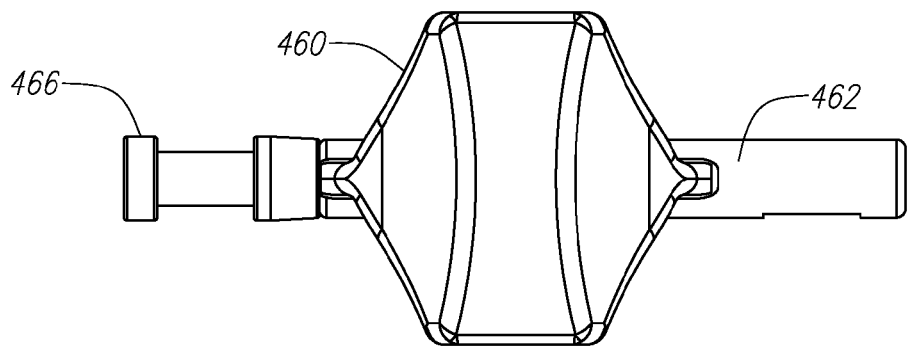
Figure 31C:
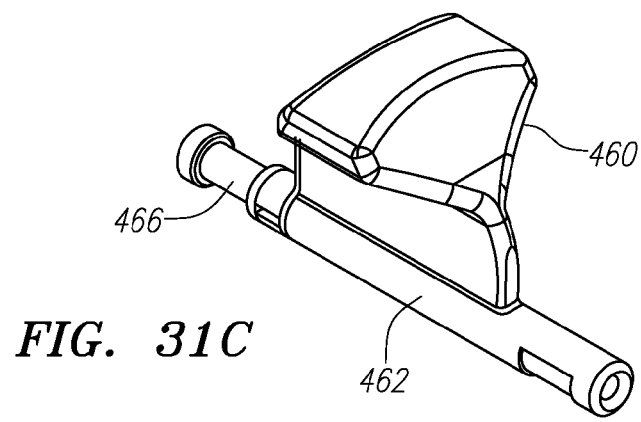
Figure 33:
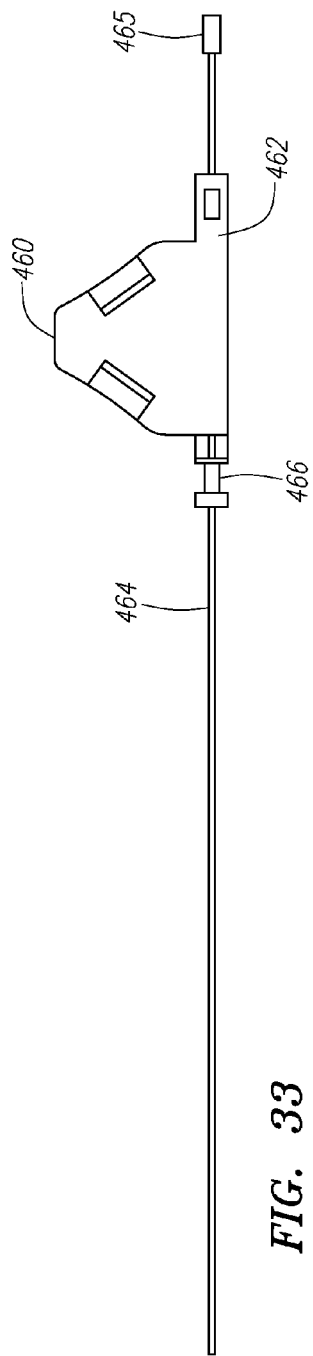
FIG. 33 is a side view of a suture deployment button, cinch bushing, and looped cable of the needle deployment assembly of FIGS. 30A-C.
Figure 34A:
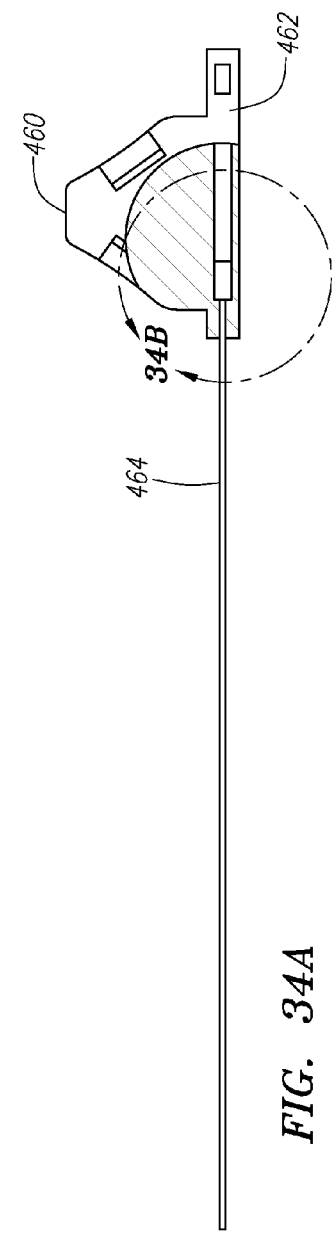
FIGS. 34A-B are partial cross-sectional views of the suture deployment button and looped cable shown in FIG. 33.
Figure 34B:
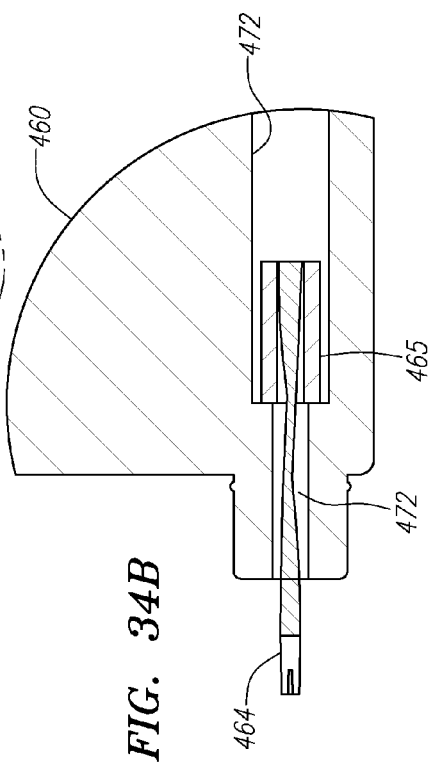

The operation of the needle deployment assembly 450 will now be described. A starting point is shown in FIGS. 30A, 32A, and 36A, in which the suture deployment button 460 is at its proximal-most extent. As the suture deployment button 460 is advanced distally, the cable bushing 462, cinch bushing 466, hypo tube 467, and pusher coil 468 are advanced distally, thereby driving the anchor assembly 48 distally until the anchor assembly 48 exits the catheter body 452 through the needle 456. (See FIG. 36B). In an embodiment, the distal anchor 50a and proximal anchor 50b are advanced in separate steps, as described more fully below. After full advancement, the distal face of the cinch bushing 466 engages a one way snap feature 474 located near the distal end of the rigid body portion 452 of the needle deployment assembly 450. (See FIG. 30D). In the embodiment shown, the one way snap feature 474 includes an inward facing tab 476 that is oriented to be resiliently biased outward as the distal face of the cinch bushing 466 engages the tab 476, and then to snap inward after the cinch bushing 466 passes distally. This action traps the cinch bushing 466 at a location distal of the inward facing tab 476, which prevents proximal movement of the cinch bushing 466 past the tab 476. A distal inward facing tab 478 prevents over-translation of the cinch bushing 466.

Once the one way snap feature 474 has engaged the cinch bushing 466, retraction of the suture deployment button 460 causes the cable bushing 462 to separate from the cinch bushing 466 at the location of the snap connect 463. (See FIGS. 34A-B). The snap connect 463 mates the cinch bushing 466 to the cable bushing 462 until a predetermined load is placed upon the snap connect 463, at which point the snap connect 463 fails and the cinch bushing 466 will separate from the cable bushing 462. As the suture deployment button 460 is then retracted proximally, the crimp tube 465 will seat within the counterbore 470 of the cable bushing 462 and the cable 464 is retracted as the pusher coil 468 remains fully extended. The distal end of the pusher coil 468 has a diameter that substantially matches up with the diameter of the cinch 62, whereby the pusher coil 468 prevents proximal movement of the cinch 62 and any of the components retained on the suture 52 on the distal side of the cinch 62. As the knot 64 engages the distal portion of the distal anchor 50a, further retraction of the button 460 causes the anchors 50a, 50b to transition to their expanded deployment state. (See FIG. 36C).

In the embodiment shown, the anchor assembly 48 includes a separation feature that facilitates separation of the anchor assembly 48 from the looped cable 464, thereby providing the ability to deposit the anchor assembly 48 and separate it from the delivery device without the need to cut the suture 52. As shown in FIG. 35C, a proximal end 53 of the suture 52 is folded over to releasably engage the distal end of the looped cable 464. In operation, after the anchor assembly 48 has been deployed, the needle deployment assembly 450 is disengaged from the actuator mechanism 370 and is retracted out of the proximal end of the main housing 372. During this withdrawal, the anchor assembly 48, which is fixed to the tissue, prevents the suture 52 from being withdrawn, which drags the looped cable 464 out of the distal end of the pusher coil 468. The crimp tube 465 seats in the counter bore 470 of the cable bushing 42 and drags the suture deployment button 460 distally for a distance sufficient to release the suture 52. Once the looped cable 464 is dragged out of the distal end of the pusher coil 468, the proximal end 53 of the suture 52 that is folded over the distal end of the looped cable 464 will release from the cable 464, thereby freeing the anchor assembly 48 from the needle deployment assembly 450.

Those skilled in the art will appreciate that other anchor assembly release features or suture cutting devices and methods may be suitable for separating the anchor assembly 48 from the delivery device.

Turning next to FIGS. 28A-C and 29A-C, additional details of the structure and operation of the needle deployment assembly actuation mechanism 390 are shown. As described above, the mechanism includes a needle launch track 396 that is fixed to the main housing 372 above the drive channel 422, and a needle launch button 394. The launch track 396 defines a channel 397 in which the button 394 is able to slide longitudinally under control of the user. The button 394 includes a base portion 394a and a top portion 394b that are attached to each other, with the base portion 394a sliding within the launch track channel 397 and the top portion 394b extending above the launch track 396 to be accessible to the user. In the embodiment shown, the base portion 394a and top portion 394b of the button 394 are attached by a tab and slot mechanism, although other attachment mechanisms are also suitable. A needle lock leaf spring 399 is positioned within the button 394. The leaf spring 399 includes a locking tab 399a that extends through a leaf spring slot 395 formed in the base portion 394a of the button.

The locking tab 399a is biased outward through the leaf spring slot 395 to engage one of the cutouts 398 formed on the needle launch track 396. When the locking tab 399a is engaged in one of the cutouts 398, the leaf spring 399 prevents the needle launch button 394 from moving along the needle launch track 396. By applying a lateral (longitudinally-directed) force on the top portion 394b of the button, the user is able to bias the leaf spring locking tab 399a inward, away from the launch track 396, thereby disengaging the tab 399a from a cutout 398 and allowing the user to slide the needle launch button 394 within the launch track channel 397.

As shown in FIGS. 25A-B, the proximal end of the needle deployment assembly includes a cap 480 having a resilient arm 481 terminating in an outwardly directed hook 482. The hook 482 has a size and shape adapted to engage and be releasably retained within a pocket 484 defined by the base portion 394a of the needle launch button 394. In alternative embodiments, the cap 480 includes a plurality of resilient arms each having a hook, and the base portion 394a includes a plurality of pockets configured to engage the plurality of hooks. The needle deployment assembly 450 is loaded into the actuator mechanism 370 by inserting the distal end of the needle deployment assembly 450 (i.e., the needle body 456) into the proximal end of the main housing 372 and directing the needle body 456 and flexible catheter body 454 distally through the lumen defined by the launch tube 228 extending through the tubular body 212. After the rigid body portion 452 is loaded into the actuation channel 424, the hook 482 engages the needle launch button 394 and the resilient arm 481 is biased inwardly until the hook 482 encounters the pocket 484 of the needle launch button 394, at which point the hook 482 will snap into the pocket 484 to thereby releasably mate the needle deployment assembly 450 to the actuator, mechanism 370. In this manner, movement of the needle launch button 394 within the drive channel 422 causes movement of the needle deployment assembly 450 relative to and concentrically within the launch tube 228. The needle deployment assembly 450 may be disengaged from the actuator mechanism 370 by the user by forcing the resilient arm 481 inward to disengage the hook 482 from the pocket 484.

FIGS. 24 and 25A show the rigid proximal portion 82 of the tubular body 212 extending from the distal end of the main housing 372. A distal shoulder 383 is defined on the interior of the tubular body 212 at the point of transition between the rigid proximal portion 82 and the flexible portion of the tubular body 212. The distal end of a launch tube spring 384 rests against the shoulder 383 in the annular space between the rigid proximal portion 82 of the tubular body and the launch tube 228. A needle deployment assembly loading sleeve cap 385 comprises a transition point between a larger diameter portion of the launch tube 228a near the proximal end of the device and a smaller diameter portion of the launch tube 228b extending distally through the flexible tubular body 212. The loading sleeve cap 385 defines a proximal shoulder 386 against which the proximal end of the launch tube spring 384 abuts. In this manner, when the launch tube 228 is advanced distally, the launch tube spring 384 is compressed between the distal shoulder 383 and the proximal shoulder 386. The spring force of the launch tube spring 384 thereby provides a force biasing the launch tube 228 proximally. This proximally-directed spring force provides resistance against a force squeezing the handle body 374 against the main body 372, thereby biasing the handle body 374 to the open position.

The spring force provided by the launch tube spring 384 also facilitates the operation of the handle lock mechanism 430 described above in relation to FIGS. 26A-B. In particular, the proximally-directed spring force applied to the launch tube 228 is transferred to the locking pin 434 through the drive bushing 420, drive bushing pin 408, and linkage arm 378. This force facilitates the movement of the locking pin 434 proximally through the lower track 446 during the return portion of the cycle. As the locking pin 434 moves proximally within the lower track 446, the ramped lower surface of the lower track 446 causes the locking pin 434 also to move upward in the inner portion 412a of the locking pin slot in order to return to the starting position 447 in which the locking pin 434 rests on the ledge 412c.

The interior of the loading sleeve cap 385 defines a surface against which the distal-most portion of the rigid body portion 452 of the needle deployment assembly 452 abuts during loading of the assembly, while allowing passage of the flexible catheter portion 454 through the lumen defined by the launch tube 228.

The combined operation of the actuator mechanism 370 and needle deployment assembly 450 will now be described. As shown in FIG. 7, the end effector 214 is located at a point near a target region of tissue, at which point the jaws 220, 222 are opened under control of the actuator mechanism 370. After the tissue is placed between the jaws 220, 222, the handle body 374 is squeezed toward the main housing 372, which causes the launch tube 228 to advance distally, closing the jaws 220, 222 upon the tissue. The distal portion of the launch tube 228 is also transitioned to an arcuate shape in which the distal opening of the launch tube 228 is positioned substantially perpendicularly to the tissue grasped between the jaws 220, 222. At this point, the locking pin 434 is positioned in the trough 445 of the outer track 444, thereby maintaining the actuator mechanism 370 in a "closed" position corresponding with a closed position of the jaws 220, 222.

Once the tissue has been grasped and the launch tube 228 positioned as described above, the needle launch button 394 is advanced distally within the launch track 396, thereby causing the needle deployment assembly 450 to be advanced through the launch tube 228. The needle launch button 394 is then locked in place by allowing the leaf spring 399 to engage one of the cutouts 398 of the needle launch track 396. The needle 456 pierces and extends through the tissue, as shown in FIG. 7. In an embodiment, the length of travel allowed for the needle launch button 394 within the launch track 396 is such that the needle 456 is prevented from extending past a desired distance beyond the lower jaw 220. Once the needle 456 is in its proper position, the distal anchor 50a is deployed by advancing the suture deployment button 460 a distance sufficient to extend the distal anchor 50a out of the needle 456 of the needle deployment assembly 450, as shown in FIG. 7. The distal anchor 50a is thereby deployed on the distal side of the tissue fold held by the jaws 220, 222. After the distal anchor 50a is deployed, the needle launch button 394 is retracted, thereby retracting the needle 456 from the tissue and into the launch tube 228. The jaws 220, 222 are disengaged from the tissue by squeezing and releasing the handle body 374 and main housing 372. As a result, the suture 52 extends through the tissue as the proximal anchor 50b remains within the needle deployment assembly 450. The proximal anchor 50b may then be deployed.

The suture deployment button 460 is then advanced distally, causing the proximal anchor 50b to be extended outside of the needle body 456 and the needle deployment assembly 450. (See, e.g., FIGS. 36B-C). The proximal anchor 50b is located on the proximal side of the tissue fold. At this point, the cinch bushing 466 engages the one way snap feature 474 to lock the cinch bushing 466 in place, thereby locking in place the hypo tube 467 and pusher coil 468. The suture deployment button 460 is then withdrawn proximally, releasing the snap connect 463 attaching the cinch bushing 466 to the cable bushing 462 and causing the looped cable 464 to be withdrawn relative to and through the pusher coil 468. This action causes the suture 52 to be retracted proximally through the distal anchor 50a, proximal anchor 50b, and the cinch 62, thereby fully deploying the anchor assembly 48. (See, e.g., FIG. 36C). The anchor assembly 48 is thereby deployed to retain a tissue fold F, as shown schematically in FIG. 1B.

The resilient arm 481 of the needle deployment assembly cap 480 is then biased inward to release the hook 482 from the needle launch button pocket 484, thereby releasing the needle deployment assembly 450 from the actuator mechanism 370. As the needle deployment assembly 450 is withdrawn, the looped cable 464 is dragged out of the distal end of the pusher coil 468, thereby releasing the folded proximal portion of the suture 53 from the looped cable 464.

The devices described herein are suitable for use in many diagnostic and therapeutic procedures in which tissue manipulation and securement is performed endoscopically or endolumenally. Examples of such procedures include endolumenal treatment of obesity (see, e.g., U.S. Provisional Patent Application Ser. No. 61/038,487, filed Mar. 21, 2008, hereby incorporated by reference), revision of obesity procedures (see, e.g., U.S. patent application Ser. No. 11/342,288, filed Jan. 27, 2006, hereby incorporated by reference), treatment of gastroesophageal reflux disease (GERD) (see, e.g., U.S. patent application Ser. No. 11/290,304, filed Nov. 29, 2005, hereby incorporated by reference), gastrotomy closure procedures (see, e.g., U.S. patent application Ser. No. 11/238,279, filed Sep. 28, 2005, hereby incorporated by reference), wound closure, fistula repair, and other procedures in which two or more portions of tissue are grasped, manipulated, approximated, or secured. Additional examples of procedures are described in the other patent applications incorporated by reference herein.

Although various illustrative embodiments are described above, it will be evident to one skilled in the art that various changes and modifications are within the scope of the invention. It is intended in the appended claims to cover all such changes and modifications that fall within the true spirit and scope of the invention.

The invention claimed is:

1. A surgical instrument comprising:
   a tubular body;
   a launch tube extending through the tubular body;
   a needle assembly movable within the launch tube;
   an end effector attached to a distal end of the tubular body by a pivotable coupling, with the end effector having a first bail and a second bail;
   with a distal end of the launch tube attached to the first bail via a fitting allowing the distal end of the launch tube to pivot relative to the first bail and also to slide linearly from a first position where the distal end of the launch tube is substantially on a first side of the first bail, to a second position where the distal end of the launch tube is substantially on a second side of the first bail, opposite from the first side.

2. The surgical instrument of claim 1 with the first bail fixed in position relative to the second bail and substantially parallel to the second bail.

3. The surgical instrument of claim 1 further comprising an end slot in a distal end of the first bail, and a suture cutter blade on the first bail, between the slot and the fitting.

4. The surgical instrument of claim 3 further comprising an end slot in a distal end of the second bail.

5. The surgical instrument of claim 3 with the end slot substantially laterally centered on the first bail.

6. A surgical instrument comprising:
   a tubular body;
   a launch tube extending through the tubular body;
   a needle assembly movable within the launch tube;

an end effector attached to a distal end of the tubular body by a pivotable coupling, with the end effector having a first bail and a second bail;

with a distal end of the launch tube attached to the first bail via a fitting allowing the distal end of the launch tube to pivot relative to the first bail, the fitting including left and right side pivot slots, and with left and right side pivot pins on the first bail engaged into the left and right side pivot slots, respectively, and with the launch tube linearly slidable between upper and lower ends of the pivot slots.

7. The surgical instrument of claim 1 further comprising a grasper supported on a slider slidable along a slide slot in the second bail.

8. The surgical instrument of claim 1 wherein the launch tube is substantially parallel to the first bail when the launch tube is in the first position.

9. The surgical instrument of claim 8 wherein the launch tube is at an acute angle to the first bail when the launch tube is in the second position.

10. The surgical instrument of claim 1 with a centerline between the first and second bails offset from a center line of the tubular body.

11. The surgical instrument of claim 1 wherein the fitting comprises a pivot/slide fitting permanently positioning a front end of the launch tube between a front end of the first jaw and a front end of the tubular body.

12. The surgical instrument of claim 1 with the launch tube having a linearly slidable range of movement limited by the fitting.

13. A surgical instrument comprising:
a tubular body;
a launch tube extending through the tubular body;
a needle assembly in the launch tube;
an end effector attached to a distal end of the tubular body by a pivotable coupling, with the end effector having a first bail and a second bail;
with a distal end of the launch tube attached to the first bail via a fitting allowing the distal end of the launch tube to pivot relative to the first bail and also allowing the distal end of the launch tube to slide from a first position where the distal end of the launch tube is substantially on a first side of the first bail, to a second position where the distal end of the launch tube is substantially on a second side of the first bail, opposite from the first side; and
a suture cutter blade adjacent to a distal end of the first bail.

14. A surgical instrument comprising:
a tubular body;
an end effector attached to the front end of the tubular body, with the end effector having a first jaw and a second jaw pivotally attached to the first jaw; and
a launch tube extending out of a front end of the tubular body, with a front end of the launch tube attached to the first jaw via a pivot/slide fitting allowing the front end of the launch tube to pivot relative to the first jaw and to also shift linearly relative to the first jaw; and
a needle assembly in the launch tube, with a needle of the needle assembly linearly slidable out from a distal end of the launch tube.

15. The surgical instrument of claim 14 with the second jaw longer than the first jaw, and with a back end of the second jaw pivotally attached to the tubular body, and with a back end of the first jaw pivotally attached onto the second jaw at a position between the back end and a front end of the second jaw.

16. The surgical instrument of claim 14 with the first jaw having a central longitudinal opening and with the launch tube positioned in the central longitudinal opening.

17. The surgical instrument of claim 14 with the launch tube slidable in a direction substantially perpendicular to a central longitudinal axis of the launch tube.

18. The surgical instrument of claim 14 with the launch tube having a linearly slidable range of movement limited by the pivot/slide fitting.

* * * * *